US010345098B2

(12) United States Patent
Hu et al.

(10) Patent No.: US 10,345,098 B2
(45) Date of Patent: Jul. 9, 2019

(54) MEASUREMENT METHOD AND MEASUREMENT DEVICE

(71) Applicant: FUJIFILM Corporation, Tokyo (JP)

(72) Inventors: Yi Hu, Ashigarakami-gun (JP); Takashi Murooka, Ashigarakami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 0 days.

(21) Appl. No.: 15/697,978

(22) Filed: Sep. 7, 2017

(65) Prior Publication Data

US 2018/0066938 A1 Mar. 8, 2018

Related U.S. Application Data

(63) Continuation of application No. PCT/JP2016/055379, filed on Feb. 24, 2016.

(30) Foreign Application Priority Data

Mar. 10, 2015 (JP) .................................. 2015-047619
Jan. 21, 2016 (JP) .................................. 2016-009968

(51) Int. Cl.
*A61M 5/31* (2006.01)
*B65B 3/00* (2006.01)
(Continued)

(52) U.S. Cl.
CPC .......... *G01B 11/2441* (2013.01); *G01B 11/00* (2013.01); *G01B 11/22* (2013.01);
(Continued)

(58) Field of Classification Search
CPC .............. G01F 25/0084; G01F 23/292; A61M 5/1782; G01N 2021/5969
See application file for complete search history.

(56) References Cited

U.S. PATENT DOCUMENTS 5,827,943 A * 10/1998 Schmidt ................ G01F 23/284
73/1.73
5,959,738 A 9/1999 Hafeman et al.
(Continued)

FOREIGN PATENT DOCUMENTS

EP 1534526 A1 6/2005
JP 04328449 A 11/1992
(Continued)

OTHER PUBLICATIONS

Communication dated Mar. 16, 2018 from European Patent Office in the counterpart application No. 16761483.3.
(Continued)

*Primary Examiner* — Shawn Decenzo
(74) *Attorney, Agent, or Firm* — Sughrue Mion, PLLC

(57) ABSTRACT

The present invention provides a measurement method, a measurement device, and a program capable of non-destructively measuring a volume of an aqueous solution of a drug in each needle-like recess of a mold with high accuracy. A measurement method according to a preferred embodiment of the present invention includes a measurement wave intensity acquisition step of acquiring, for each needle-like recess, an intensity of a measurement wave transmitted through a drug in a needle-like recess, absorbed by the drug by an amount according to a distance by which the measurement wave is transmitted through the drug, and emitted from the drug; and a volume acquisition step of acquiring a volume for each needle-like recess on the basis of the intensity of the measurement wave for each needle-like recess acquired in the measurement wave intensity acquisition step.

26 Claims, 37 Drawing Sheets

(51) Int. Cl.
*A61M 37/00* (2006.01)
*A61M 5/178* (2006.01)
*G01B 11/00* (2006.01)
*G01B 11/22* (2006.01)
*G01B 11/24* (2006.01)
*G01F 17/00* (2006.01)
*G01F 22/00* (2006.01)
*G01F 25/00* (2006.01)
*G01F 23/292* (2006.01)

(52) U.S. Cl.
CPC .............. *G01B 11/24* (2013.01); *G01F 17/00* (2013.01); *G01F 22/00* (2013.01); *G01F 23/292* (2013.01); *A61M 5/1782* (2013.01); *A61M 5/31* (2013.01); *A61M 2037/0053* (2013.01); *B65B 3/006* (2013.01); *G01F 25/0084* (2013.01)

(56) References Cited

U.S. PATENT DOCUMENTS

| | | | |
|---|---|---|---|
| 2002/0089561 A1* | 7/2002 | Weitzel | B41J 2/125 347/19 |
| 2003/0107738 A1* | 6/2003 | Curtis | G01F 23/292 356/436 |
| 2006/0083111 A1* | 4/2006 | Grasso | G01S 17/026 367/131 |
| 2006/0178578 A1* | 8/2006 | Tribble | B65B 3/003 600/432 |
| 2010/0053614 A1* | 3/2010 | Jeys | G01N 15/1434 356/343 |
| 2010/0192523 A1* | 8/2010 | Stoeckel | A61J 3/074 53/503 |
| 2012/0027810 A1* | 2/2012 | Chen | A61M 37/0015 424/400 |
| 2015/0092200 A1* | 4/2015 | Zahniser | G01N 15/1475 356/627 |
| 2018/0058902 A1* | 3/2018 | Murooka | A61M 37/00 |
| 2018/0058903 A1* | 3/2018 | Hu | G01B 11/24 |
| 2018/0058904 A1* | 3/2018 | Murooka | A61M 37/00 |
| 2018/0080871 A1* | 3/2018 | Imai | G01N 21/645 |
| 2018/0106659 A1* | 4/2018 | Kunbargi | G01F 25/0061 |

FOREIGN PATENT DOCUMENTS

| | | |
|---|---|---|
| JP | 0814988 A | 1/1996 |
| JP | 2005512085 A | 4/2005 |
| JP | 2008246435 A | 10/2008 |
| JP | 2010175291 A | 8/2010 |
| JP | 2011224332 A | 11/2011 |
| JP | 2012254952 A | 12/2012 |
| JP | 2013162982 A | 8/2013 |

OTHER PUBLICATIONS

Communication dated Aug. 2, 2018, issued by the Japan Patent Office in corresponding Japanese Application No. 2016-009968.

International Preliminary Report on Patentability, dated Sep. 12, 2017 from the International Bureau in counterpart International application No. PCT/JP2016/055379.

Translation of Written Opinion of the International Searching Authority dated May 24, 2016, from the International Bureau in counterpart International application No. PCT/JP2016/055379.

International Search Report dated May 24, 2016 from the International Bureau in counterpart International application No. PCT/JP2016/055379.

Notification of Reasons for Refusal dated Feb. 19, 2018 from the Japanese Patent Office in counterpart Japanese application No. 2016-009968.

* cited by examiner

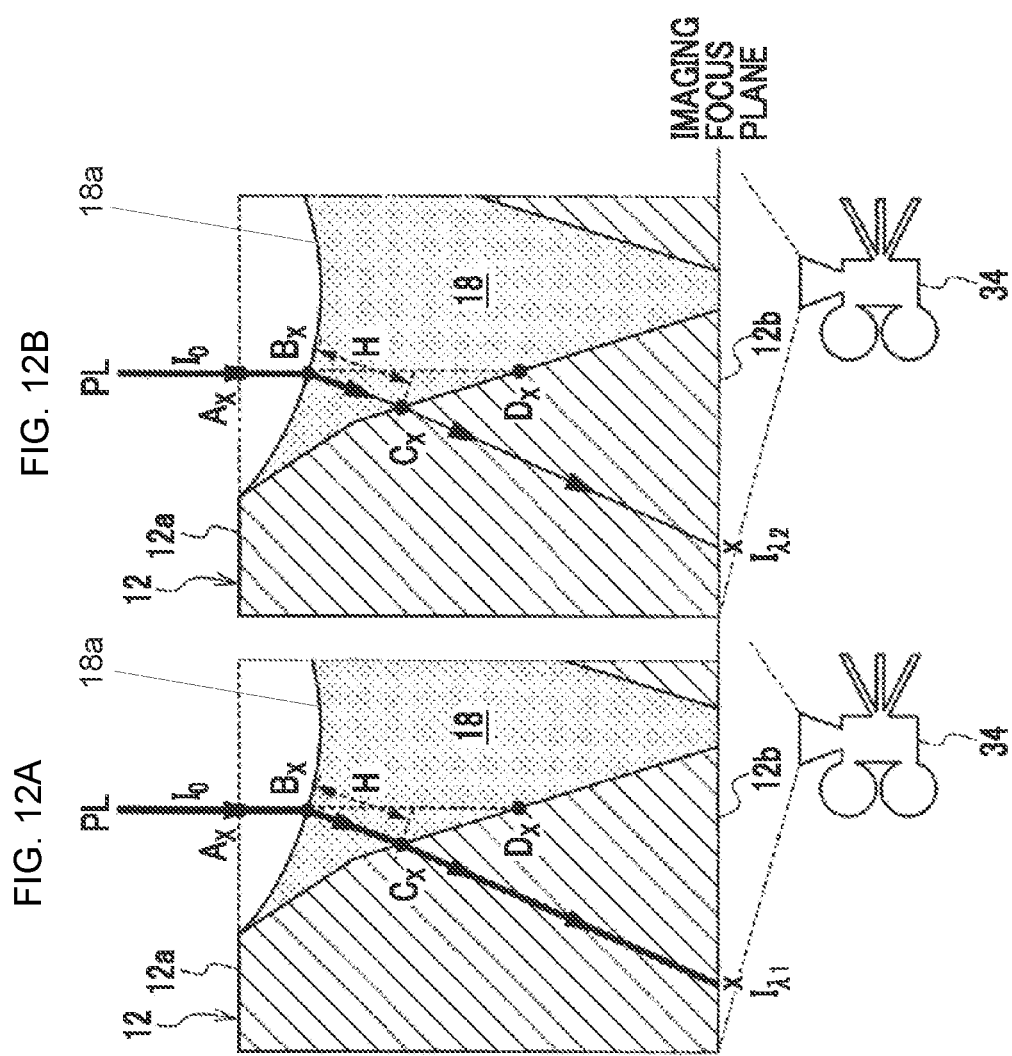

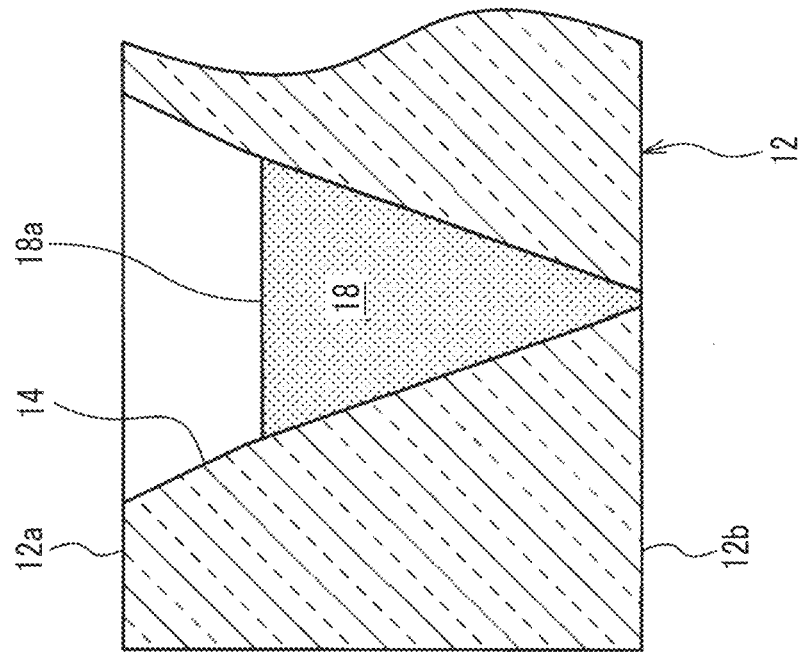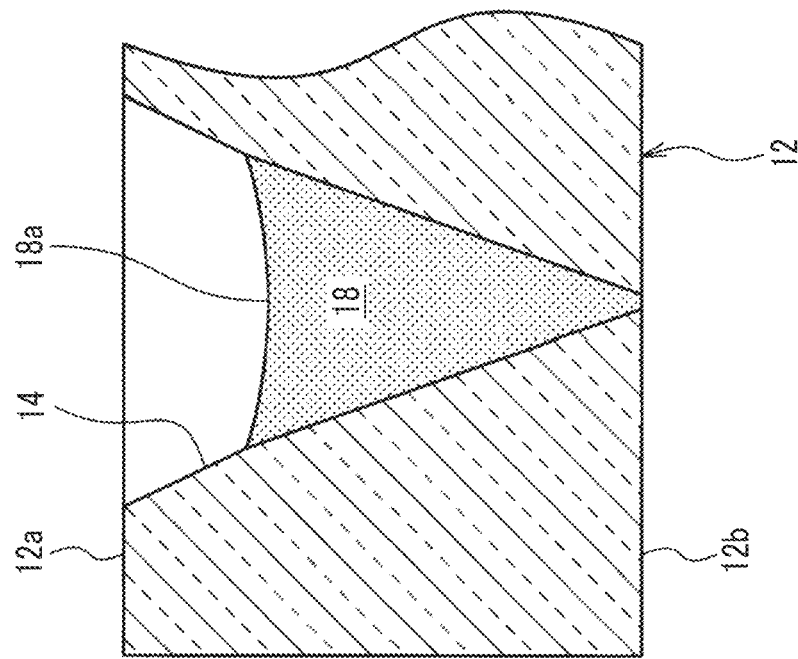

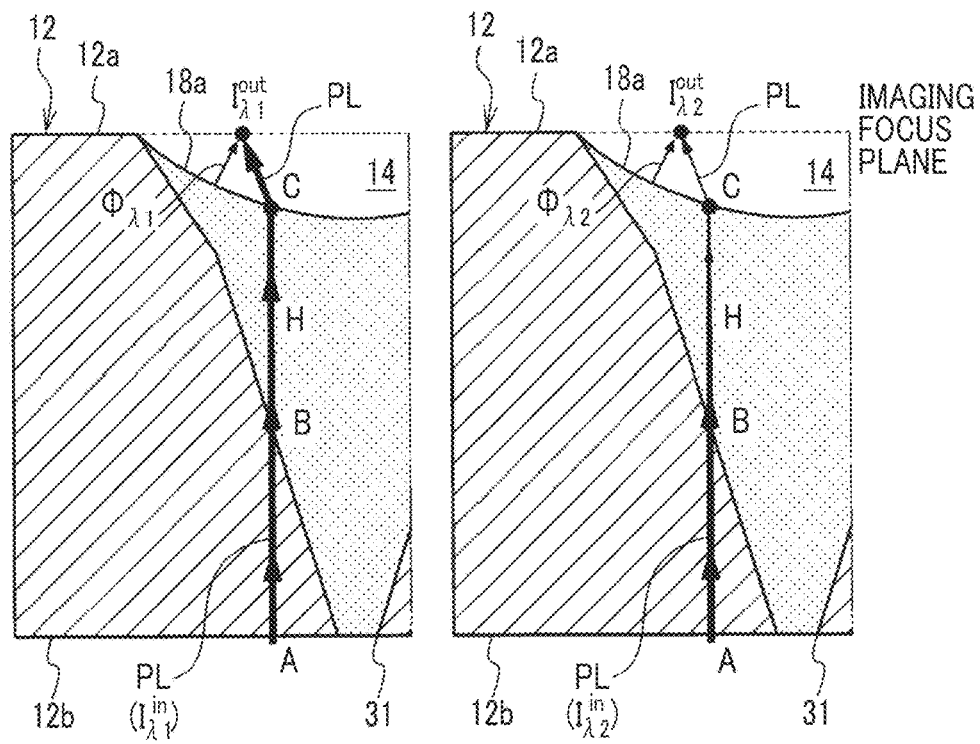

FIG. 27A

| FIRST DATA TABLE | |
|---|---|
| SUM OR REPRESENTATIVE VALUE OF $I_{\lambda 1}$ | VOLUME |
| X1 | Va |
| X2 | Vb |
| X3 | Vc |
| ⋮ | ⋮ |

| SUM OR REPRESENTATIVE VALUE OF $I_{\lambda 2}$ | VOLUME |
|---|---|
| Y1 | Vα |
| Y2 | Vβ |
| Y3 | Vγ |
| ⋮ | ⋮ |

FIG. 27B

| SECOND DATA TABLE | |
|---|---|
| $I_{\lambda 1}$ | DISTANCE H |
| Xa | Ha |
| Xb | Hb |
| Xc | Hc |
| ⋮ | ⋮ |

| $I_{\lambda 2}$ | DISTANCE H |
|---|---|
| Ya | Hα |
| Yb | Hβ |
| Yc | Hγ |
| ⋮ | ⋮ |

91

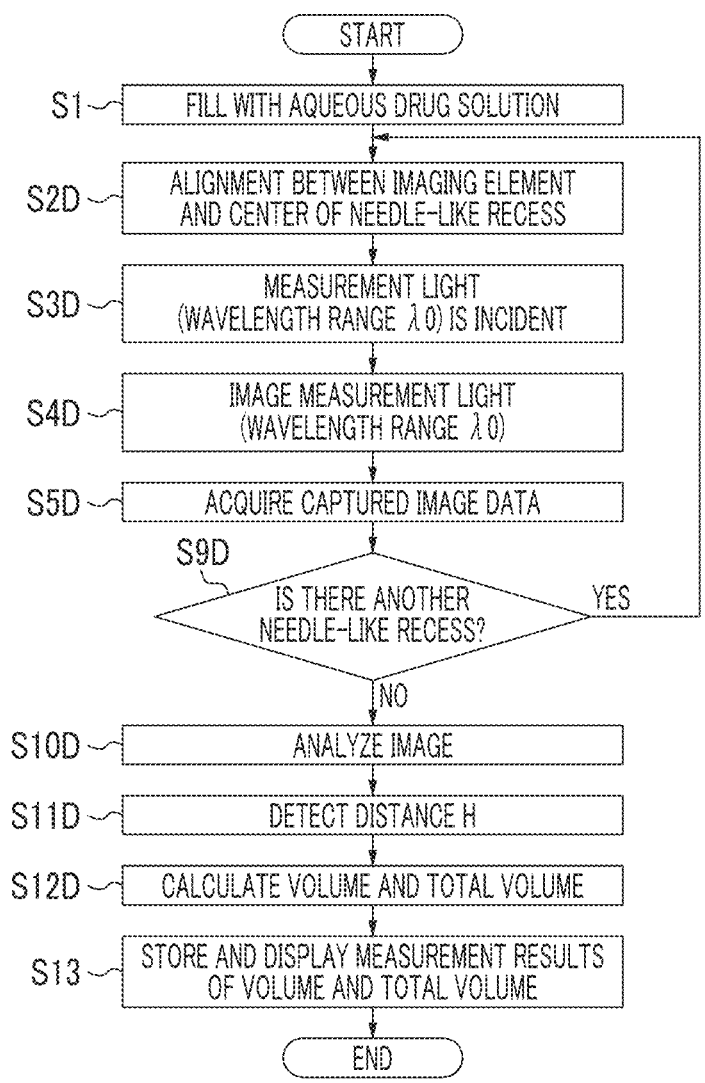

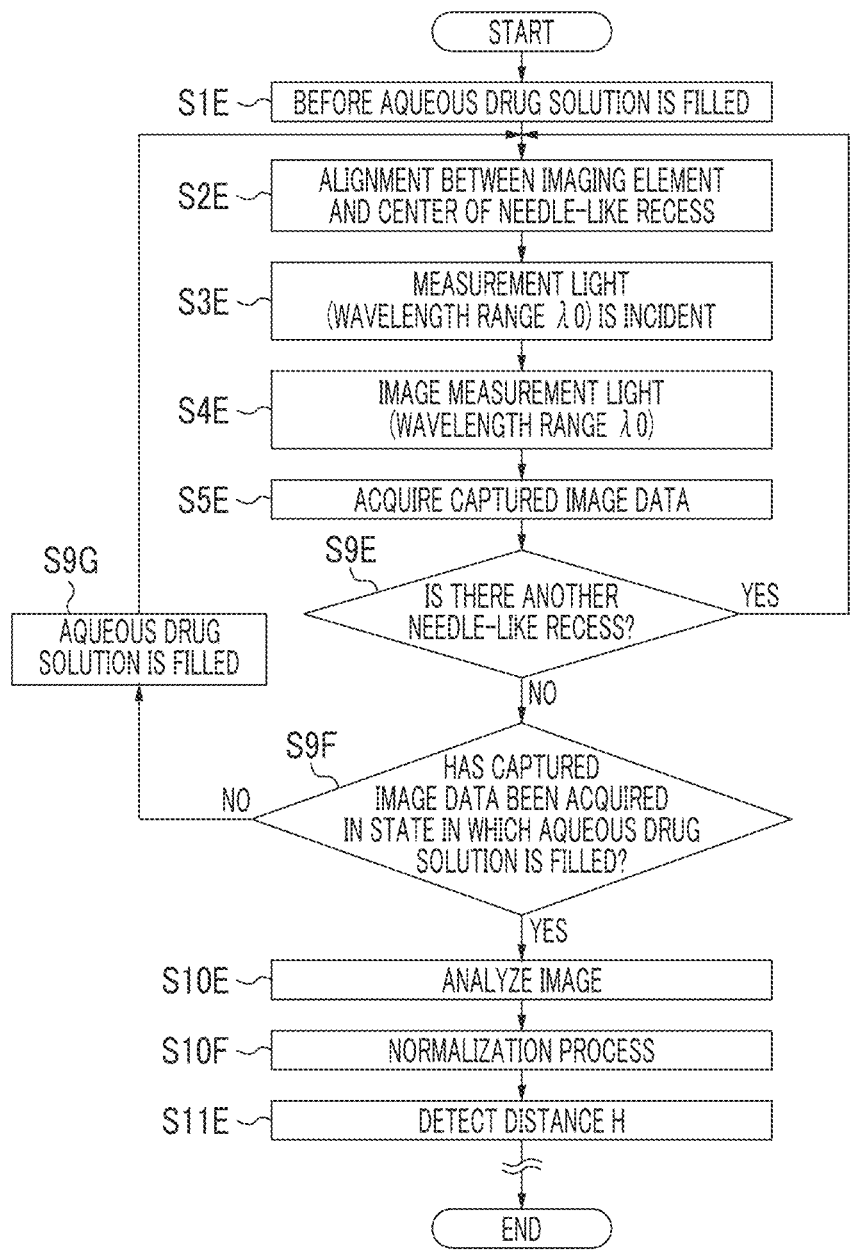

MEASUREMENT METHOD AND MEASUREMENT DEVICE

CROSS-REFERENCE TO RELATED APPLICATIONS

This application is a Continuation of PCT International Application No. PCT/JP2016/055379 filed on Feb. 24, 2016, which claims priorities under 35 U.S.C. § 119(a) to Japanese Patent Application No. 2015-047619 filed on Mar. 10, 2015 and Japanese Patent Application No. 2016-009968 filed on Jan. 21, 2016. Each of the above applications is hereby expressly incorporated by reference, in their entirety, into the present application.

BACKGROUND OF THE INVENTION

1. Field of the Invention

The present invention relates to a measurement method, a measurement device, and a program for measuring a volume (amount of filling) of a drug filled in a needle-like recess of a mold for forming a micro-needle.

2. Description of the Related Art

In recent years, a micro-needle array (hereinafter abbreviated as MNA) is known as a novel dosage form capable of administering a drug such as insulin, vaccines, and human Growth Hormone (hGH) into the skin without pain. In the MNA, biodegradable micro-needles containing a drug are arranged in an array form. By affixing this MNA to a skin, each micro-needle can pierce the skin, the micro-needle can be absorbed into the skin, and the drug contained in each micro-needle can be administered into the skin.

As a method of manufacturing such an MNA, a method of filling and drying an aqueous drug solution containing a drug or the like in each needle-like recess of a mold having a large number of needle-like recesses that are inverted types of MNA to form the MNA, and then, peeling the MNA from the mold is known (see JP2013-162982A and JP2012-254952A). When the MNA is manufactured, it is necessary to strictly manage the amount of the drug to be administered into the skin from the MNA. Therefore, in the MNA manufacturing process, quantification of the amount of the drug contained in the MNA is achieved.

In the method of manufacturing an MNA described in JP2011-224332A, the amount of a drug contained in the MNA is measured by dissolving the MNA in water. However, in the method described in JP2011-224332A, there is a problem in that a produced MNA is destructed because destructive measurement is required.

Here, the amount of the drug supplied into the skin by the MNA depends on a volume (capacity) of an aqueous drug solution filled in each needle-like recess of the mold. Therefore, quantification of the amount of the drug contained in the MNA can be achieved by measuring the volume of the aqueous drug solution filled in each needle-like recess of the mold and quantifying the volume of the aqueous drug solution in each needle-like recess.

As a method of measuring a volume of an aqueous drug solution filled in each needle-like recess of the mold, for example, a method of measuring a weight of a mold before filling with an aqueous drug solution and a weight of the mold after filling with the aqueous drug solution with a high-precision electronic balance and measuring a volume of the aqueous drug solution on the basis of a weight difference before and after filling and a density of the aqueous drug solution is known. According to the method of measuring the volume with this high-precision electronic balance, it is possible to perform non-destructive measurement of the volume of the aqueous drug solution filled in each needle-like recess of the mold.

SUMMARY OF THE INVENTION

However, even in a case where the high-precision electronic balance is used, it is difficult to measure the volume of the aqueous drug solution with high precision and high speed. The reasons for this are as follows: 1) since a measurement result of the electronic balance in a case where a very small amount is measured is greatly affected by a measurement environment (temperature, humidity, and convection) and a mold material (for example, water absorption characteristics, and it is easy for static electricity to be generated), the measurement result becomes unstable. For example, a case where a weight of the mold is 800 mg and the mold is filled with 2 mg of an aqueous drug solution will be described by way of example. In this case, if an allowable range of a variation in the volume of 2 mg is ±3% of 2 mg, this allowable range is ±0.06 mg. Thus, it is necessary for the high-precision electronic balance to have a resolution of 0.01 mg. However, a measured value (a weight value) is not stable when an empty mold before filling is weighed even when a balance has a resolution of 0.01 mg due to an influence of a measurement environment (temperature, humidity, and convection) and characteristics of a mold material (silicon rubber itself has water absorption characteristics and it is easy for static electricity to be accumulated). Further, even in measurements under a controlled environment (constant temperature and humidity, no wind flow, and removal of static electricity), a variation in measured values is several times to tens of times the resolution. Therefore, it is difficult to acquire measurement results with high accuracy (for example, 1% or less) even when the high-precision electronic balance is used.

2) Further, there is a problem in that a measurement time of an electronic balance including the high-precision electronic balance is long. A measurement time until measurement is stabilized after the mold is set on the electronic balance is several seconds (3 to 8 seconds), particularly, in the case of a high-precision electronic balance. 3) In a case where measurement is performed in a high-precision electronic balance, it is necessary to perform measurement on a mold-by-mold basis. For example, in a case where tens of MNAs (also called mold patches) are formed on one sheet, it is necessary to separate each MNA (mold patch) from the sheet in order to perform the measurement, but this work is not allowed in an actual production process. That is, a weight measurement method using a high-precision electronic balance is not suitable for a roll-to-roll production method.

Further, in the measurement using the high-precision electronic balance as described above, the volume of the aqueous drug solution of each needle-like recess of the mold cannot be individually measured. As a result, a variation in the volume of the aqueous drug solution of each needle-like recess cannot be measured. Therefore, development of a technology capable of nondestructively measuring the volume of an aqueous drug solution of each needle-like recess of the mold at high speed and with high precision is desired. Further, in this case, since MNAs of a plurality of kinds of drugs such as insulin and vaccines are generally manufactured while switching the MNAs in an MNA manufacturing process, development of a measurement technology that does not depend on a kind of drug is desired.

JP2012-254952A described above discloses a method of coloring each micro-needle of the MNA with blue, observing the blue micro-needle peeled from the mold with a video microscope, and measuring a length of a colored part. Since a shape of each needle-like recess of the mold is known, an individual capacity (volume) of the micro-needle in each needle-like recess is obtained on the basis of a measurement result of the length of the micro-needle in each needle-like recess. However, in this method, the micro-needle after drying is a measurement target. Accordingly, the method can be carried out irrespective of a kind of drug, but the method is a destructive inspection (reason: each micro-needle of MNA is colored with blue), and speed and accuracy are low (reason: the blue micro-needle peeled from the mold is observed with a video microscope). Thus, the method is not suitable for nondestructive, high-precision, and high-speed inspection which is required for mass production. There is also a scheme for estimating the volume on the basis of a concentration obtained by measuring the blue aqueous solution prepared by adding water to the micro-needle with a spectrophotometer instead of observing the peeled blue micro-needle with the video microscope. This method is not suitable for inspection required for mass production due to the same reason as described above (the method is a destructive inspection, a measurement time is one to two days, and measurement accuracy is lower than in the gravimetric measurement with a high-precision balance).

The present invention has been made in view of the above circumstances, and an object of the present invention is to provide a measurement method, a measurement device, and a program capable of non-destructively measuring a volume of an aqueous solution of a drug in each needle-like recess of a mold with high accuracy.

A measurement method for achieving the object of the present invention is a measurement method of measuring a volume of a drug filled in a needle-like recess of a mold in which a plurality of needle-like recesses that are inverted types of a micro-needle are formed, the measurement method comprising: a measurement wave intensity acquisition step of acquiring, for each needle-like recess, an intensity of a measurement wave transmitted through the drug in the needle-like recess, absorbed by the drug by an amount according to a distance by which the measurement wave is transmitted through the drug, and emitted from the drug; and a volume acquisition step of acquiring the volume for each needle-like recess on the basis of the intensity of the measurement wave for each needle-like recess acquired in the measurement wave intensity acquisition step.

According to this measurement method, it is possible to non-destructively measure the volume of the drug in each needle-like recess on the basis of the intensity of the measurement light transmitted through the drug in each needle-like recess of the mold with high accuracy. Further, it is possible to perform high-speed measurement in comparison with a method using a high-precision electronic balance of the related art.

In the measurement method according to another aspect of the present invention, the measurement wave intensity acquisition step includes acquiring the intensity of the measurement wave in a wavelength range absorbed by the water, for each of the needle-like recesses, in a case where the drug contains water. Accordingly, it is possible to non-destructively measure the volume of the aqueous drug solution in each needle-like recess with high accuracy.

In the measurement method according to still another aspect of the present invention, the volume acquisition step includes acquiring a total volume of the volume of the drug filled in the mold from the volume of the drug of each needle-like recess. Accordingly, it is possible to non-destructively measure the total volume of the drug with high accuracy.

In the measurement method according to still another aspect of the present invention, the volume of the drug decreases over time due to evaporation of the water contained in the drug, the measurement method further comprises an elapsed time acquisition step of acquiring an elapsed time until the measurement wave intensity acquisition step starts after the drug is filled in the needle-like recess, and the volume acquisition step includes correcting a decrease over time of the volume of the drug of each needle-like recess on the basis of the elapsed time acquired in the elapsed time acquisition step, and acquiring the amount of filling of the drug filled in the needle-like recess for each needle-like recess. Accordingly, since the amount of filling of the drug in each needle-like recess (the volume of the drug immediately after filling) can be acquired, it is possible to feed back this acquisition result to the filling device that fills the drug in each needle-like recess. As a result, it is possible to appropriately adjust the amount of filling of the drug for each of the needle-like recesses by the filling device.

The measurement method according to still another aspect of the present invention further comprises a correction value acquisition step of acquiring a correction value for correcting a decrease over time of the volume of the drug in the needle-like recess, wherein the volume acquisition step includes correcting the volume of the drug of each needle-like recess using the correction value acquired in the correction value acquisition step on the basis of the elapsed time acquired in the elapsed time acquisition step, and acquiring the amount of filling of the drug of each needle-like recess. Thus, it is possible to appropriately adjust the amount of filling of the drug for each of the needle-like recesses by the filling device.

The measurement method according to still another aspect of the present invention further comprises an acquisition result processing step of executing at least one of a display of the acquisition result acquired in the volume acquisition step and storage of the acquisition result in a storage unit. Thus, a user can confirm the acquisition result by displaying the acquisition result, and the user can confirm the acquisition result at any time by storing the acquisition result in the storage unit.

In the measurement method according to still another aspect of the present invention, the measurement wave intensity acquisition step includes: a first acquisition process of acquiring, for each needle-like recess, an intensity of the measurement wave transmitted through the drug in the needle-like recess and emitted from the drug; a second acquisition process of acquiring an intensity of the measurement wave transmitted through a region different from the drug; and a normalization process of normalizing the intensity of the measurement wave for each needle-like recess acquired in the first acquisition process, using the intensity of the measurement wave acquired in the second acquisition process, and the volume acquisition step includes acquiring the volume for each needle-like recess on the basis of the intensity of the measurement wave for each needle-like recess subjected to the normalization process. By performing the normalization process, it is possible to measure the volume of the drug in each needle-like recess more accurately.

In the measurement method according to still another aspect of the present invention, the volume acquisition step includes acquiring, for each needle-like recess, a distance by which the measurement wave is transmitted through the drug in the needle-like recess on the basis of the intensity of the measurement wave of each needle-like recess acquired in the measurement wave intensity acquisition step, and acquiring the volume of the drug for each of the needle-like recesses on the basis of the acquired distance of each needle-like recess and a known shape of the needle-like recesses. It is possible to easily measure the volume of the drug in each needle-like recess.

In the measurement method according to still another aspect of the present invention, the volume acquisition step includes acquiring the volume of the drug of each needle-like recess by referring to a correspondence relationship between an intensity of the measurement wave that is acquired in advance and the volume on the basis of the intensity of the measurement wave of each needle-like recess acquired in the measurement wave intensity acquisition step. Accordingly, since the volume of the drug in each needle-like recess can be directly acquired from the correspondence relationship, a calculation process can be reduced.

In the measurement method according to still another aspect of the present invention, the measurement wave intensity acquisition step includes repeatedly performing a process of acquiring, for each needle-like recess, the intensity of the measurement wave incident on the mold from a second surface opposite to a first surface on which the drug of the mold is filled, and emitted from the drug surface of the drug, while changing the wavelength range of the measurement wave, and the volume acquisition step includes a distance detection step of detecting, for each needle-like recess, a distance by which the measurement wave in the plurality of wavelength ranges emitted from each position of the drug surface is transmitted through the drug from the acquisition result acquired for each wavelength range in the measurement wave intensity acquisition step; and a volume calculation step of calculating the volume for each needle-like recess on the basis of the result of the detection of the distance detection step. Accordingly, it is possible to measure the volume of the drug in each needle-like recess with higher accuracy.

In the measurement method according to still another aspect of the present invention, the measurement wave intensity acquisition step includes: an incidence step of causing the measurement wave to be incident on the second surface in a case where the measurement wave is light; an arrangement step of alternately inserting and arranging a plurality of filters that limit a wavelength range of the measurement wave into and in an optical path of the measurement wave, the wavelength range limited by the plurality of filters being different; a captured image acquisition step of acquiring, for every plurality of filters, a captured image obtained by imaging the measurement wave transmitted through any one of the plurality of filters and the drug; and an image analysis step of analyzing the captured image for every plurality of filters acquired in the captured image acquisition step and detecting an intensity of the measurement wave for each needle-like recess for every plurality of wavelength ranges corresponding to the plurality of filters. Accordingly, it is possible to acquire the intensity of the measurement wave for each needle-like recess for every plurality of wavelength ranges.

In the measurement method according to still another aspect of the present invention, in a case where the measurement wave is a first measurement wave and a second measurement wave in different wavelength ranges, and in a case where the intensity of the first measurement wave at each position is $I_{\lambda,1}$, the intensity of the second measurement wave at each position is $I_{\lambda,2}$, and a parameter affecting the intensity of the first measurement wave and the intensity of the second measurement wave is P, the distance detection step includes obtaining the distance H at each position using the following formula: $H=f[(I_{\lambda,1}), (I_{\lambda,2}), P]$. Accordingly, it is possible to obtain the distance H at each position from the intensities of the first measurement wave and the second measurement wave and the parameter using a calculation formula.

In the measurement method according to still another aspect of the present invention, in a case where the drug contains water and the first measurement wave and the second measurement wave are light, the parameter P includes an optical absorption coefficient $\alpha_{\lambda,1}$ of the water corresponding to the first measurement wave and an optical absorption coefficient $\alpha_{\lambda,2}$ of the water corresponding to the second measurement wave, and the distance detection step includes obtaining the distance H at each position using the following formula: $H=f[(I_{\lambda,1}), (I_{\lambda,2}), \alpha_{\lambda,1}, \alpha_{\lambda,2}]$. Accordingly, it is possible to obtain the distance H at each position from the intensities of the first measurement wave and the second measurement wave and the optical absorption coefficient using a calculation formula.

In the measurement method according to still another aspect of the present invention, the distance detection step includes obtaining the distance H at each position using the following formula:

$$H = \frac{\log_{10} I_{\lambda_1} - \log_{10} I_{\lambda_2}}{\alpha_{\lambda_2} - \alpha_{\lambda_1}}.$$

Accordingly, it is possible to obtain the distance H at each position from the intensities of the first measurement wave and the second measurement wave and the optical absorption coefficient using a calculation formula.

In the measurement method according to still another aspect of the present invention, in a case where the measurement wave is a first measurement wave and a second measurement wave in different wavelength ranges, the measurement wave intensity acquisition step includes acquiring an incidence intensity of each of the first measurement wave and the second measurement wave incident on the second surface, and an emission intensity of each of the first measurement wave and the second measurement wave emitted from each position of the drug surface for each needle-like recess, and the distance detection step includes obtaining the distance H at each position using the following formula on the basis of the acquisition result of the measurement wave intensity acquisition step, an optical absorption coefficient $\alpha_{\lambda,1}$ of the water corresponding to the first measurement wave, and an optical absorption coefficient $\alpha_{\lambda,2}$ of the water corresponding to the second measurement wave.

$$H = -\frac{\log_{10} I_{\lambda_2}^{out} - \log_{10} I_{\lambda_1}^{out} - (\log_{10} I_{\lambda_2}^{in} - \log_{10} I_{\lambda_1}^{in})}{\alpha_{\lambda_2} - \alpha_{\lambda_1}}$$

$I_{\lambda_1}^{in}$: Incidence intensity of first measurement wave
$I_{\lambda_1}^{out}$: Emission intensity of first measurement wave
$I_{\lambda_2}^{in}$: Incidence intensity of second measurement wave
$I_{\lambda_2}^{out}$: Emission intensity of second measurement wave
$\alpha_{\lambda_1}$: Optical absorption coefficient of water corresponding to first measurement wave
$\alpha_{\lambda_2}$: Optical absorption coefficient of water corresponding to second measurement wave Thus, even in a case where the incidence intensity of the measurement wave for each wavelength range is different, it is possible to measure the volume of the drug in each needle-like recess with high accuracy.

In the measurement method according to still another aspect of the present invention, in a case where the measurement wave is a first measurement wave and a second measurement wave in different wavelength ranges, and the distance detection step includes detecting the distance at each position on the basis of a difference between the intensity of the first measurement wave at each position and the intensity of the second measurement wave at each position. Accordingly, by detecting the distance from the difference, it is possible to cancel an influence of stray light included in the first measurement wave and the second measurement wave and to detect the distance at each position more accurately. As a result, it is possible to measure the volume of the drug in each needle-like recess with high accuracy.

In the measurement method according to still another aspect of the present invention, the volume acquisition step includes acquiring the volume of the drug of each needle-like recess by referring to a correspondence relationship between at least one of intensities of the measurement wave in the respective wavelength ranges acquired in advance and the volume on the basis of the intensity of the measurement wave of each needle-like recess acquired for each wavelength range in the measurement wave intensity acquisition step. Accordingly, since the volume of the drug in each needle-like recess can be directly acquired from the correspondence relationship, a calculation process can be reduced.

In the measurement method according to still another aspect of the present invention, in a case where the measurement wave is a first measurement wave, a second measurement wave, and a third measurement wave in different wavelength ranges, the measurement wave intensity acquisition step includes acquiring an incidence intensity of each of the first measurement wave, the second measurement wave, and the third measurement wave incident on the second surface, and an emission intensity of each of the first measurement wave, the second measurement wave, and the third measurement wave emitted from each position of the drug surface for each needle-like recess, and the distance detection step includes obtaining the distance H at each position using the following formula on the basis of the acquisition result of the measurement wave intensity acquisition step, an optical absorption coefficient $\alpha_{\lambda,1}$ of the water corresponding to the first measurement wave, an optical absorption coefficient $\alpha_{\lambda,2}$ of the water corresponding to the second measurement wave, and an optical absorption coefficient $\alpha_{\lambda,3}$ of the water corresponding to the third measurement wave.

$$H = \underset{H=0 \sim H_{max}}{\operatorname{argmin}} \{\Delta D = |(I_{\lambda_1}^{out} - I_{\lambda_2}^{out}) \cdot (I_{\lambda_3}^{in} \cdot 10^{-\alpha_{\lambda_3} \cdot H} - I_{\lambda_1}^{in} \cdot 10^{-\alpha_{\lambda_2} \cdot H}) - (I_{\lambda_3}^{out} - I_{\lambda_2}^{out}) \cdot (I_{\lambda_1}^{in} \cdot 10^{-\alpha_{\lambda_1} \cdot H} - I_{\lambda_2}^{in} \cdot 10^{-\alpha_{\lambda_2} \cdot H})|\}$$

$I_{\lambda_1}^{in}$: Incidence intensity of first measurement wave
$I_{\lambda_1}^{out}$: Emission intensity of first measurement wave
$I_{\lambda_2}^{in}$: Incidence intensity of second measurement wave
$I_{\lambda_2}^{out}$: Emission intensity of second measurement wave
$I_{\lambda_3}^{in}$: Incidence intensity of third measurement wave
$I_{\lambda_3}^{out}$: Emission intensity of third measurement wave
$\alpha_{\lambda_1}$: Optical absorption coefficient of water corresponding to first measurement wave
$\alpha_{\lambda_2}$: Optical absorption coefficient of water corresponding to second measurement wave
$\alpha_{\lambda_3}$: Optical absorption coefficient of water corresponding to third measurement wave Accordingly, it is possible to cancel an influence of stray light and to detect the distance at each position more accurately. As a result, it is possible to measure the volume of the drug in each needle-like recess with high accuracy.

In a measurement method according to still another aspect of the present invention further comprises a shape detection step of detecting a shape of the drug surface of each needle-like recess on the basis of a detection result in the distance detection step and a known shape of the needle-like recess. Accordingly, it is possible to detect a surface shape of the drug in the needle-like recess at the same time.

In the measurement method according to still another aspect of the present invention, the measurement wave is light, and the drug absorbs light in a plurality of specific wavelength ranges and includes water having a different optical absorbance for each specific wavelength range, and the measurement wave intensity acquisition step includes determining the wavelength range of the measurement wave from among the plurality of specific wavelength ranges according to a thickness of the mold. Thus, it is possible to determine the wavelength range of the measurement wave suitable for a thickness of the mold.

In the measurement method according to still another aspect of the present invention, the measurement wave is light, and the drug absorbs light in a plurality of specific wavelength ranges and includes water having a different optical absorbance for each specific wavelength range, and the measurement wave intensity acquisition step includes determining the wavelength range of the measurement wave from among the plurality of specific wavelength ranges according to the amount of filling of the drug filled in the needle-like recess. Accordingly, it is possible to determine a wavelength range of the measurement wave suitable for the amount of filling of the drug.

A measurement device for achieving the object of the present invention is a measurement device that measures a volume of a drug filled in a needle-like recess of a mold in which a plurality of needle-like recesses that are inverted types of a micro-needle are formed, the measurement device comprising: a measurement wave intensity acquisition unit that acquires, for each needle-like recess, an intensity of a measurement wave transmitted through the drug in the needle-like recess, absorbed by the drug by an amount according to a distance by which the measurement wave is transmitted through the drug, and emitted from the drug; and a volume acquisition unit that acquires the volume for each needle-like recess on the basis of the intensity of the measurement wave for each needle-like recess acquired by the measurement wave intensity acquisition unit.

A program for achieving the object of the present invention is a program that causes a computer to function as means for measuring a volume of a drug filled in a needle-like recess of a mold in which a plurality of needle-like recesses that are inverted types of a micro-needle are formed, the program causing the computer to function as: a measurement wave intensity acquisition unit that acquires an intensity of a measurement wave for each needle-like recess from an acquisition unit that acquires an intensity of the measurement wave transmitted through the drug in the needle-like recess, absorbed by the drug by an amount according to a distance by which the measurement wave is transmitted through the drug, and emitted from the drug; and a volume acquisition unit that acquires the volume for each needle-like recess on the basis of the intensity of the measurement wave for each needle-like recess acquired by the measurement wave intensity acquisition unit. A computer-readable non-transitory tangible medium having the program recorded thereon is also included in an aspect of the present invention.

The measurement method, the measurement device, and the program of the present invention can non-destructively measure the volume of an aqueous solution of a drug in each needle-like recess of a mold with high accuracy.

BRIEF DESCRIPTION OF THE DRAWINGS

FIG. 12A is an illustrative diagram illustrating an optical path of a comparative example in which measurement light in a wavelength range $\lambda 1$ is transmitted through an aqueous drug solution in a needle-like recess in a case where a positional relationship between a light source and an imaging portion is reversed from this embodiment, and FIG. 12B is an illustrative diagram illustrating an optical path of a comparative example in which measurement light in the wavelength range $\lambda 2$ is transmitted through the aqueous drug solution in the needle-like recess.

FIG. 20A is a cross-sectional view of a mold in which a hydrophilic treatment is not performed on a first surface, and FIG. 20B is a cross-sectional view of a mold on which the hydrophilic treatment is performed on the first surface.

FIGS. 23A and 23B are illustrative diagrams illustrating a process of detecting a distance H in a measurement device of a third embodiment.

FIG. 27A is an illustrative diagram illustrating an example of a first data table, and FIG. 27B is an illustrative diagram illustrating an example of a second data table.

FIG. 33 is a flowchart illustrating a flow of a process of measuring a volume of an aqueous drug solution in each needle-like recess in the measurement device of the seventh embodiment.

FIG. 35 is a flowchart illustrating a flow of measurement of a volume of an aqueous drug solution in each needle-like recess in a measurement device of an eighth embodiment.

DESCRIPTION OF THE PREFERRED EMBODIMENTS

[Overall Configuration of Measurement Device of First Embodiment]

Figure 1:
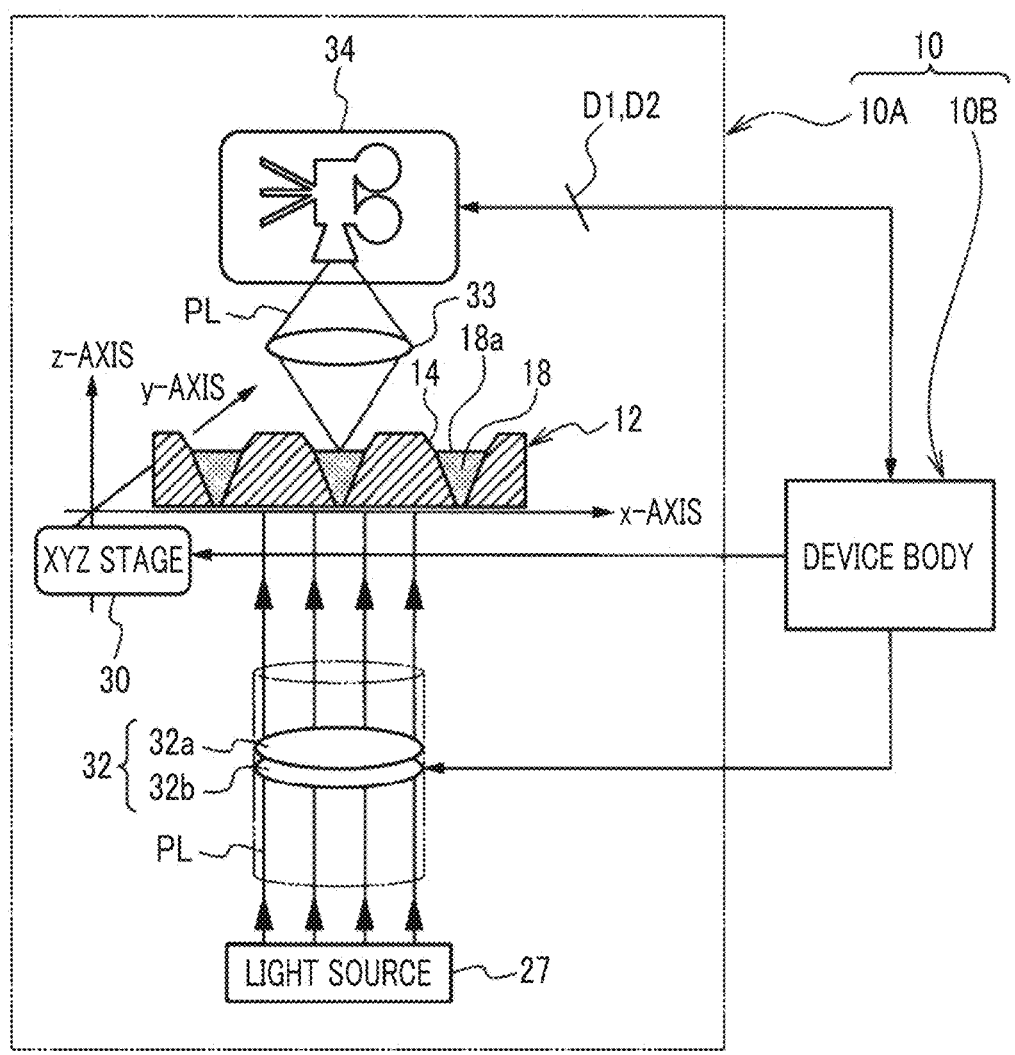
FIG. 1 is a schematic diagram of a measurement device according to a first embodiment of the measurement method and measurement device of the present invention.

FIG. 1 is a schematic diagram of a measurement device 10 according to a first embodiment according to the measurement method and the measurement device of the present invention. This measurement device 10 measures a volume of an aqueous drug solution 18 that is an aqueous solution of a drug 16 (see FIG. 3) filled in needle-like recesses 14 of a mold 12. The measurement device 10 roughly includes an imaging unit 10A, and a device body 10B. Both of the drug 16 and the aqueous drug solution 18 that is the drug 16 containing water 19 (see FIG. 4) correspond to a drug of the present invention.

Figure 2:
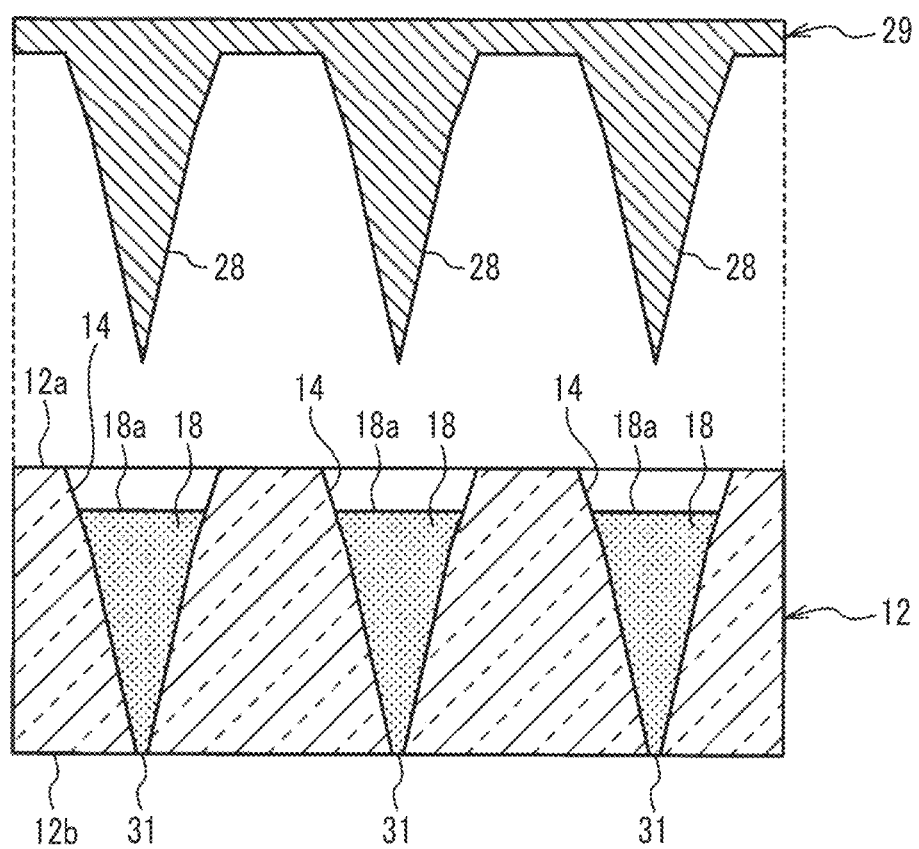
FIG. 2 is a cross-sectional view of a mold.

FIG. 2 is a cross-sectional view of the mold 12. As illustrated in FIG. 2, the mold 12 is a flat plate-shaped mold that is used for manufacture of an MNA 29 in which micro-needles 28 are arranged in an array form. In this embodiment, this mold 12 is formed of, for example, silicon rubber and has light transmittance. Here, the light transmittance is a concept including transparent and semi-transparent, and more particularly, is a property of transmitting at least a part of measurement light PL (corresponding to measurement waves of the present invention) that is emitted from a light source 27 to be described below. A plurality of needle-like recesses 14 that are an inverted type of micro-needles 28 are formed in an array form in the mold 12.

The needle-like recesses 14 have a conical shape that gradually tapers from a first surface 12a (an upper surface in FIG. 2) of the mold 12 to a second surface 12b (a lower surface in FIG. 2) opposite to the first surface 12a, corresponding to a shape of the micro-needles 28. Therefore, a wall surface of the needle-like recess 14 is an inclined surface. In this embodiment, the needle-like recess is formed so that a tilt angle of an opening adjacent portion on the first surface 12a side of the needle-like recess 14 among wall surfaces of the needle-like recesses 14 is smaller than a tilt angle of other portions (see FIG. 11B or the like).

The aqueous drug solution 18 is filled in each needle-like recess 14 of the mold 12 from the first surface 12a side. A reference sign 18a in FIG. 2 indicates a drug surface that is a surface (liquid surface) of the aqueous drug solution 18 filled in the needle-like recess 14.

A plurality of communication holes 31 communicating to the respective needle-like recesses 14 are formed in the second surface 12b of the mold 12. The mold 12 is set in the imaging unit 10A in a state in which the first surface 12a is directed to top in FIG. 2 and the second surface 12b is directed to bottom in FIG. 2 after the aqueous drug solution 18 is filled in the needle-like recesses 14.

After the aqueous drug solution 18 is filled in the needle-like recesses 14, the mold 12 is dried, the water 19 evaporates from the aqueous drug solution 18 in the needle-like recesses 14 (see FIG. 4), the drug 16 (see FIG. 3) is solidified, and the micro-needles 28 are formed in the needle-like recesses 14. Accordingly, the MNA 29 is formed on the first surface 12a of the mold 12, and the MNA 29 is peeled from the mold 12.

Figure 3:
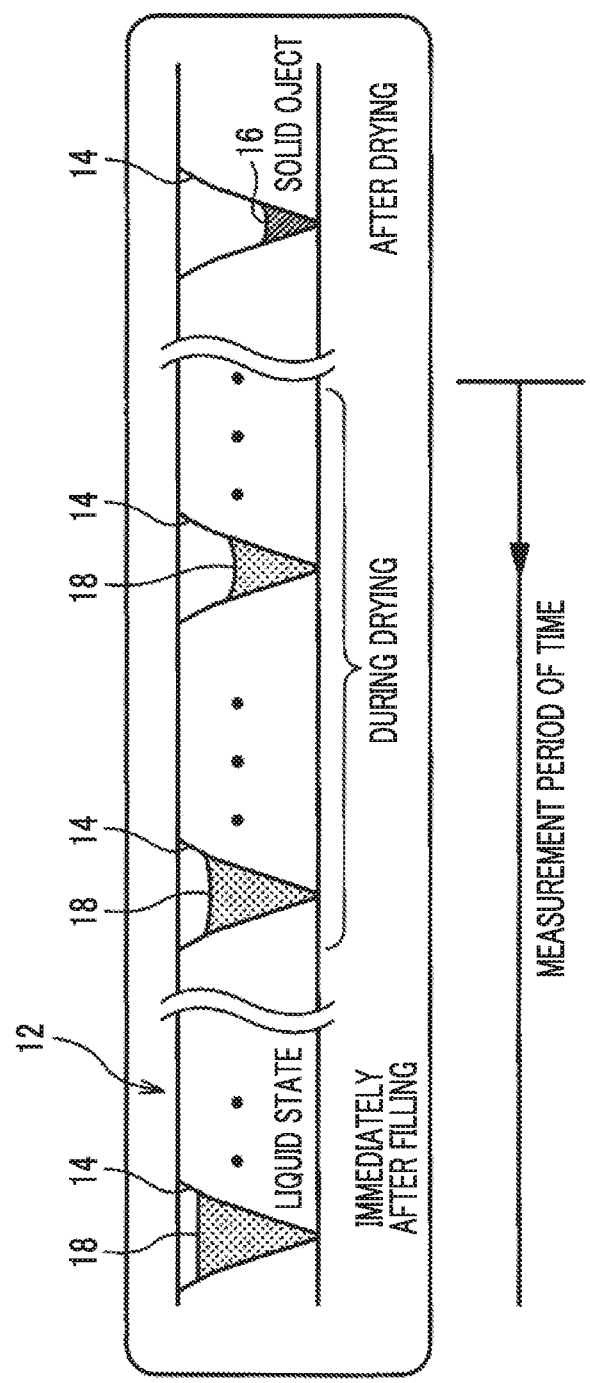
FIG. 3 is an illustrative diagram illustrating a state change of an aqueous drug solution filled in each needle-like recess of a mold.

FIG. 3 is an illustrative diagram illustrating a state change of the aqueous drug solution 18 filled in the needle-like recess 14 of the mold 12. Here, the left portion of FIG. 3 illustrates a state immediately after the aqueous drug solution 18 is filled in the needle-like recess 14, the middle portion of FIG. 3 illustrates a drying state in which the mold 12 is dried, and the right portion of FIG. 3 illustrates a state after the mold 12 is dried.

As illustrated in FIG. 3, the mold 12 is dried after the aqueous drug solution 18 is filled in the needle-like recesses 14, the water 19 (see FIG. 4) evaporates from the aqueous drug solution 18 in a liquid state in the needle-like recesses 14, the drug 16 is eventually solidified as a solid object, and the micro-needles 28 are formed in the needle-like recesses 14. Accordingly, the MNA 29 is formed on the first surface 12a of the mold 12, as illustrated in FIG. 2 described above.

The micro-needle 28 is a crystal of the drug 16 contained in the aqueous drug solution 18. Therefore, optical characteristics (such as a refractive index or an optical absorbance) of the micro-needles 28 may vary according to the type of the drug 16 contained in the aqueous drug solution 18.

On the other hand, in the aqueous drug solution 18, the water 19 (see FIG. 4) occupies about 80%, a proportion of the drug 16 is several %, and the remainder is a hydroxyethyl starch (HES) solution or the like. Thus, since the water 19 (see FIG. 4) and the HES solutions or the like occupy 95% in the aqueous drug solution 18, the water 19 (see FIG. 4) contained in the aqueous drug solution 18 determines the optical characteristics of the aqueous drug solution 18, which will be described in detail below. Accordingly, even when the type of the drug 16 in the aqueous drug solution 18 changes, the optical characteristics of the aqueous drug solution 18 do not greatly change. Therefore, in the measurement device 10, a volume (capacity) of the aqueous drug solution 18 filled in the needle-like recesses 14 is measured focusing on the optical absorption characteristics of the water 19 (see FIG. 4) contained in the aqueous drug solution 18.

Figure 4:
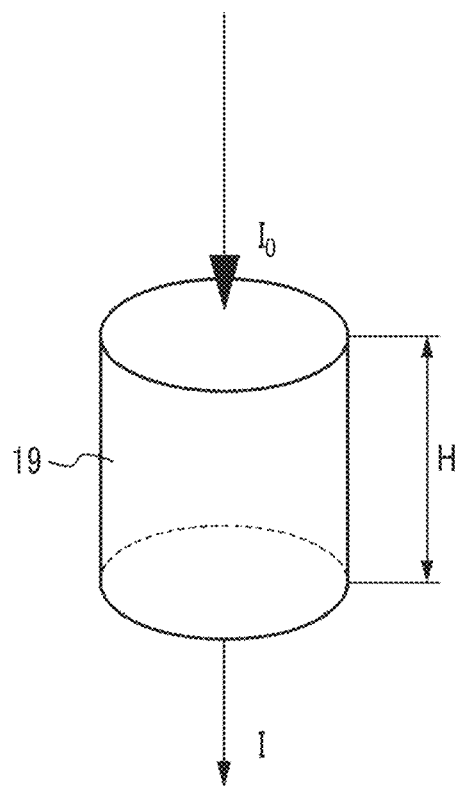
FIG. 4 is an illustrative diagram illustrating optical absorption characteristics of water contained in an aqueous solution of a drug.

FIG. 4 is an illustrative diagram illustrating optical absorption characteristics of the water 19 contained in the aqueous drug solution 18. In a case where an intensity of light incident on the water 19 is $I_0$, an intensity of light transmitted through the water 19 is I ($I<I_0$). a distance by which the light passes through (transmitted through) the water 19 is H, and an optical absorption coefficient of the water 19 for light with a wavelength is $\alpha_\lambda$ as illustrated in FIG. 4, the optical absorption characteristics of the water 19 are expressed using the following formula.

$$\frac{I}{Io} = 10^{-\alpha_\lambda H} \qquad \text{[General Formula 1]}$$

According to [General Formula 1], since a predetermined relationship between the absorption of light by the water 19 and the distance H by which the light passes through the water 19 is held, the distance H can be obtained by measuring the absorption of light by the water 19.

Figure 5:
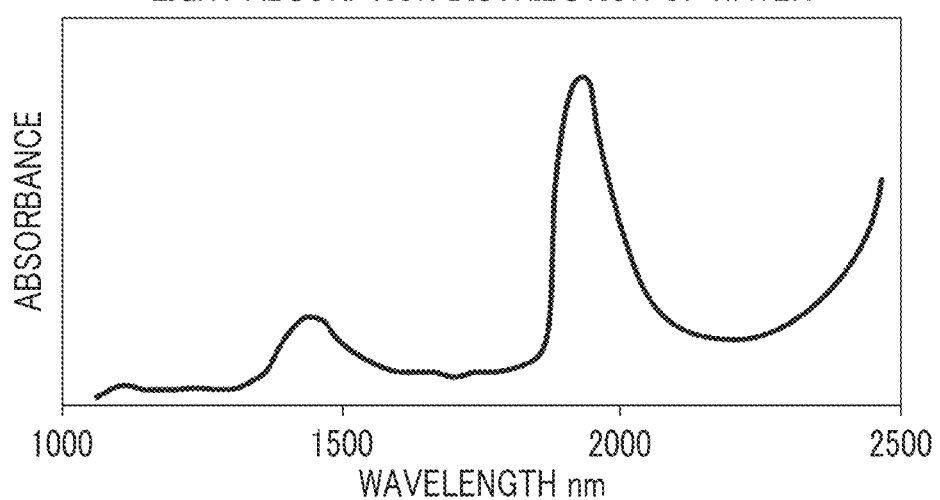
FIG. 5 is a graph of optical absorption distribution illustrating a distribution of optical absorption of the water.

FIG. 5 is a graph of an optical absorption distribution indicating a distribution of optical absorption of the water 19. A horizontal axis of this graph indicates a wavelength range λ (nm) of light, and a vertical axis indicates an optical absorption coefficient [log ($I_0/I$)]. As illustrated in FIG. 5, in a case where the wavelength λ of light is about 1400 nm and about 1900 nm, optical absorption by the water 19 increases. Accordingly, for example, in the case of the light having the wavelength λ of about 1400 nm, an absorbance of the light decreases in a case where there is a small amount of water 19 (in a case where the above distance H is short), and conversely, the absorbance of the light increases in a case where there is a large amount of water 19 (in a case where the above distance H is long).

Figure 6:
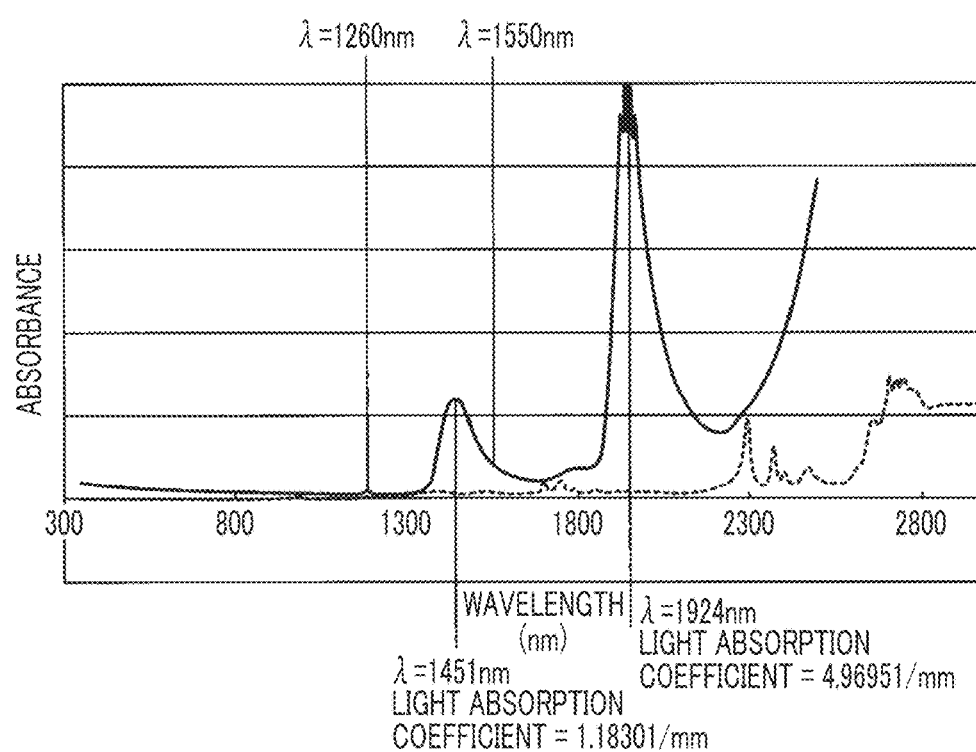
FIG. 6 is a graph of an optical absorption distribution illustrating a distribution of optical absorption of an aqueous drug solution.

FIG. 6 is a graph of an optical absorption distribution (indicated by a solid line in FIG. 6) indicating a distribution of optical absorption of the aqueous drug solution 18. Horizontal and vertical axes of this graph are the same as in the graph illustrated in FIG. 5. Further, in FIG. 6, an optical absorption distribution of the mold 12 (indicated by a dotted line in FIG. 6) is also displayed.

As illustrated in FIG. 6, the optical absorption distribution of the aqueous drug solution 18 is basically the same as the optical absorption distribution of the water 19 illustrated in FIG. 5 described above, and an absorbance of light is high at a wavelength λ of about 1400 nm and about 1900 nm. Therefore, a component (such as the drug 16) other than the water 19 contained in the aqueous drug solution 18 does not basically affect the optical absorption by the water 19 contained in the aqueous drug solution 18. Therefore, in the measurement device 10, the volume of the aqueous drug solution 18 filled in the needle-like recess 14 is measured regardless of a kind of the drug 16 contained in the aqueous drug solution 18 by focusing on the optical absorption by the water 19 contained in the aqueous drug solution 18. Although will be described in detail below, light having the wavelength λ in FIG. 6 of 1260 nm, light having the wavelength λ of about 1450 nm, and light having the wavelength λ of about 1550 nm are light in a wavelength range that is used for measurement of the measurement device 10 that will be described below.

A measurement time in the measurement device 10 is before the water contained in the aqueous drug solution 18 evaporates and the drug 16 is solidified and, specifically, is immediately after the aqueous drug solution 18 is filled in the needle-like recess 14 illustrated in the left portion of FIG. 3 described above, and during drying of the mold 12 illustrated in the middle portion of FIG. 3 described above. In a case where the measurement is performed during drying of the mold 12, it is preferable for the measurement to be started in a predetermined time after the aqueous drug solution 18 is filled in the needle-like recesses 14 of the mold 12 or at a certain time in the predetermined time. Here, "in a predetermined time" is in a time in which there is no great change in the state of the aqueous drug solution 18 in a measurement time. Since this time is changed due to manufacturing conditions of the MNA 29 (a kind of drug 16, a shape of the needle-like recess 14, temperature at the time of drying, or the like), the time is determined by an experiment, simulation, or the like for each manufacturing condition. For example, "in a predetermined time" in this embodiment is in 5 minutes. Further, if the measurement starts at a certain time in a predetermined time, the measurement of the volume of the aqueous drug solution 18 in the needle-like recess 14 can be always performed under the same conditions in a case where the water 19 evaporates from the aqueous drug solution 18.

Referring back to FIG. 1, in the measurement of the measurement device 10, first, the measurement light PL incident on the second surface 12b of the mold 12 by the imaging unit 10A vertically (Hereinafter, vertically includes substantially vertical in this specification), is passed through each part of the mold 12 (such as the aqueous drug solution 18), the measurement light PL emitted from the first surface 12a is imaged, and captured image data of the measurement light PL is obtained. Then, in the device body 10B, the captured image data is analyzed to acquire a transmitted light intensity of the measurement light PL, and the distance H by which the measurement light PL is passed through the aqueous drug solution 18 in each needle-like recess 14 is detected on the basis of the acquired transmitted light intensity. By detecting the distance H of the measurement light PL emitted from each position of the drug surface 18a within each needle-like recess 14, it is possible to detect the volume of the aqueous drug solution 18 filled in each needle-like recess 14.

In this case, calculation of the distance H using [General Formula 1] can be applied to only the measurement light PL that is not transmitted through the mold 12, that is, measurement light PL directly incident on the aqueous drug solution 18 in the needle-like recess 14 from the communication hole 31. The measurement light PL transmitted through the mold 12 and incident on the aqueous drug solution 18 in the needle-like recess 14 is affected by refraction or the like at an interface between an inner surface of the needle-like recess 14 and the aqueous drug solution 18. Therefore, since the transmitted light intensity of the measurement light PL is a value affected by a thing other than optical absorption of the aqueous drug solution 18 (water 19), an error may occur in the result of the detection of the distance H in [General Formula 1].

Accordingly, in the measurement device 10 of the first embodiment, two types of measurement light PL transmitted through the mold 12 are imaged by the imaging unit 10A using two types of measurement light PL having different wavelength ranges to acquire two types of the first captured image data D1 and the second captured image data D2. The two types of first captured image data D1 and second captured image data D2 are analyzed by the device body 10B to detect the distance H of the measurement light PL emitted from each position of the drug surface 18a within each needle-like recess 14.

<Configuration of Imaging Unit>

Figure 7:
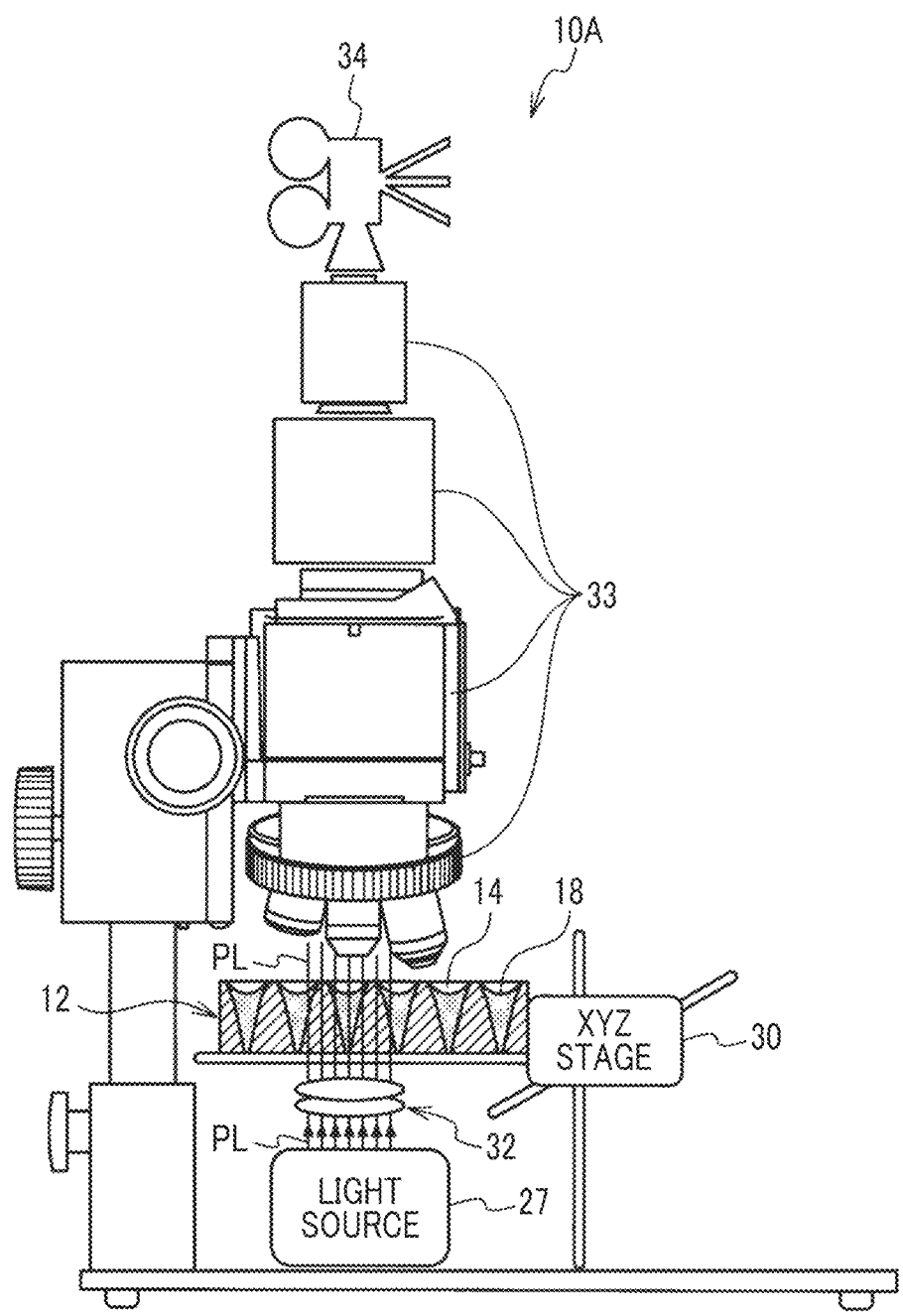
FIG. 7 is a side view of an imaging unit illustrating an example of a specific configuration of the imaging unit illustrated in FIG. 1.

FIG. 7 is a side view of the imaging unit 10A illustrating an example of a specific configuration of the imaging unit 10A illustrated in FIG. 1.

As illustrated in FIGS. 1 and 7, the imaging unit 10A roughly includes an XYZ stage 30, a light source 27, a wavelength selection filter 32, an imaging optical system 33, and an imaging portion 34.

The XYZ stage 30 is a transparent stage having light transmittance. This XYZ stage 30 movably supports the mold 12, in which the aqueous drug solution 18 has been filled in the needle-like recesses 14, in each direction of an X-axis, a Y-axis, and a Z-axis (see FIG. 1). Further, a position of the XYZ stage 30 is adjusted in each direction of the XYZ axes by a stage driving mechanism (not illustrated) under the control of the device body 10B to be described below. Thus, a position of the mold 12 can be adjusted in a parallel direction parallel to the first surface 12a and the second surface 12b (hereinafter simply referred to as a parallel direction) and a height direction perpendicular to the first surface 12a and the second surface 12b (hereinafter simply referred to as a height direction).

The light source 27 is arranged on the second surface 12b side of the mold 12, that is, below the mold 12 in FIG. 7. The light source 27 emits the measurement light PL toward the second surface 12b of the mold 12 after the filling of the aqueous drug solution 18. This measurement light PL corresponds to the first measurement wave and the second measurement wave of the present invention (that is, measurement waves of the present invention) and is, for example, parallel light orthogonal to (including substantially orthogonal to) the first surface 12a or the second surface 12b in this example. It is preferable for the measurement light PL to be light in a wavelength range in which an absorbance of light by the water 19 increases, that is, infrared light (IR light).

The wavelength selection filter 32 is arranged between the light source 27 and the XYZ stage 30. The wavelength selection filter 32 includes a first interference filter 32a and a second interference filter 32b corresponding to a filter of the present invention, and both of the interference filters 32a and 32b are alternately inserted into and arranged in an imaging optical path that is an optical path of the measurement light PL (corresponding to an optical path of the present invention). The wavelength selection filter 32 performs switching of the interference filter (the first interference filter 32a and the second interference filter 32b) that is inserted into the imaging optical path under the control of the device body 10B.

In FIG. 7, in order to prevent complication of the drawings, a state in which the two interference filters 32a and 32b are inserted into the imaging optical path is illustrated. Further, the imaging optical path is an optical path until the measurement light PL emitted from the light source 27 reaches the imaging portion 34 that will be described below.

For example, a band pass filter that limits the wavelength range of the measurement light PL that is transmitted may be used as the first interference filter 32a and the second interference filter 32b. The first interference filter 32a passes the measurement light PL in a first wavelength range of the present invention in which a center wavelength is a wavelength $\lambda 1$ (hereinafter simply abbreviated as a "wavelength range $\lambda 1$") among the measurement light PL incident from the light source 27. Accordingly, the measurement light PL with the wavelength range $\lambda 1$ is incident on the second surface 12b of the mold 12. On the other hand, the second interference filter 32b passes the measurement light PL in a second wavelength range of the present invention in which a center wavelength is a wavelength $\lambda 2$ (hereinafter simply abbreviated as a "wavelength range $\lambda 2$") different from the wavelength $\lambda 1$ among the measurement light PL incident from the light source 27. Accordingly, the measurement light PL with the wavelength range $\lambda 2$ is incident on the second surface 12b of the mold 12. Intensities of the measurement light PL in the wavelength range $\lambda 1$ and the measurement light PL in the wavelength range $\lambda 2$ are the same. Further, the "wavelength range" herein is not, for example, a band in which light with a single wavelength of laser light or the like is excluded.

The measurement light PL in two types of different wavelength ranges (wavelength ranges $\lambda 1$ and $\lambda 2$) can be caused to be alternately incident on the second surface 12b of the mold 12 by performing switching of the interference filters (the first interference filter 32a and the second interference filter 32b) to be inserted into the imaging optical path in this manner. The measurement light PL emitted from the light source 27 in a state in which the first interference filter 32a is inserted into the imaging optical path corresponds to a first measurement wave of the present invention, and the measurement light PL emitted from the light source 27 in a state in which the second interference filter 32b is inserted into the imaging optical path corresponds to a second measurement wave of the present invention.

Selection of the wavelength ranges $\lambda 1$ and the wavelength range $\lambda 2$ will be described in detail below, and the measurement light PL in the wavelength range $\lambda 1$ is light in a wavelength range in which a degree of absorption by the water 19 is lower than in the measurement light PL in the wavelength range $\lambda 2$ (an absorbance of light is low). Conversely, the measurement light PL in the wavelength range $\lambda 2$ is light in a wavelength range in which a degree of absorption by the water 19 is higher than in the measurement light PL in the wavelength range $\lambda 1$ (the absorbance of light is high).

The imaging optical system 33 is arranged on the first surface 12a side of the mold 12, that is, in an upper part in the drawing of the mold 12. The imaging optical system 33 guides the measurement light PL in the wavelength range $\lambda 1$ and the measurement light PL in the wavelength range $\lambda 2$ transmitted through the mold 12 (including the aqueous drug solution 18 in the needle-like recess 14) to the imaging portion 34, and causes the measurement light PL to be formed as an image on the imaging surface of the imaging portion 34.

The imaging portion 34 is arranged above the imaging optical system 33. The imaging portion 34 includes a charge coupled device (CCD) type imaging element or a complementary metal oxide semiconductor (CMOS) type imaging element. This imaging portion 34 is an infrared camera capable of imaging the measurement light PL with sensitivity in a wavelength range including the wavelength range $\lambda 1$ and the wavelength range $\lambda 2$, for example, an infrared range. The imaging portion 34 images the measurement light PL in the wavelength range $\lambda 1$ and the measurement light PL in the wavelength range $\lambda 2$ formed on the imaging surface of the imaging element from the imaging optical system 33 under control of the device body 10B.

In this case, in the imaging portion 34, imaging is performed in a state in which a focus (hereinafter referred to as an imaging focus) is set on the first surface 12a through the imaging optical system 33 in order to image the measurement light PL transmitted through the first surface 12a of the mold 12. As a method of setting the imaging focus on the first surface 12a, for example, various methods such as a method of forming a mark (may be irregularity letters or symbols) serving as a target of focus adjustment in the first surface 12a and performing the focus adjustment on the mark serving as the target, or a method of performing focus adjustment on trash, scratches, and various traces on the first surface 12a serving as a target may be adopted.

In a case where the measurement light PL in the wavelength range $\lambda 1$ is formed as an image on the imaging surface of the imaging element through the imaging optical system 33, the imaging portion 34 images the measurement light PL in the wavelength range $\lambda 1$ to generate the first captured image data D1, and outputs the first captured image data D1 to the device body 10B. On the other hand, in a case where the measurement light PL in the wavelength range $\lambda 2$ is formed as an image on the imaging surface of the imaging element through the imaging optical system 33, the imaging portion 34 images the measurement light PL in the wavelength range $\lambda 2$ to generate the second captured image data D2, and outputs the second captured image data D2 to the device body 10B. The first captured image data D1 and the second captured image data D2 have the same size and the same number of pixels.

Figure 8A:
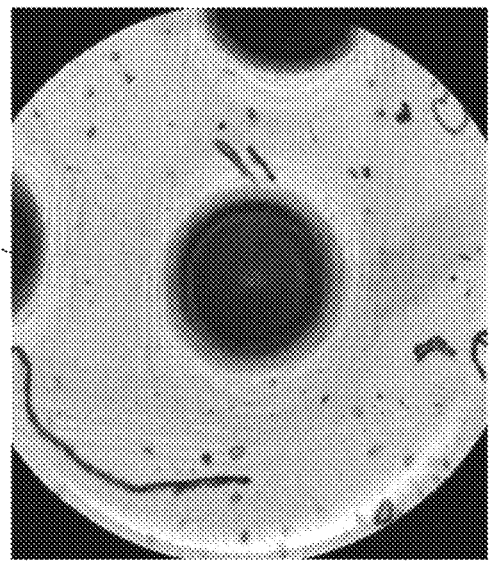
FIG. 8A is a front view of first captured image data.
Figure 8B:
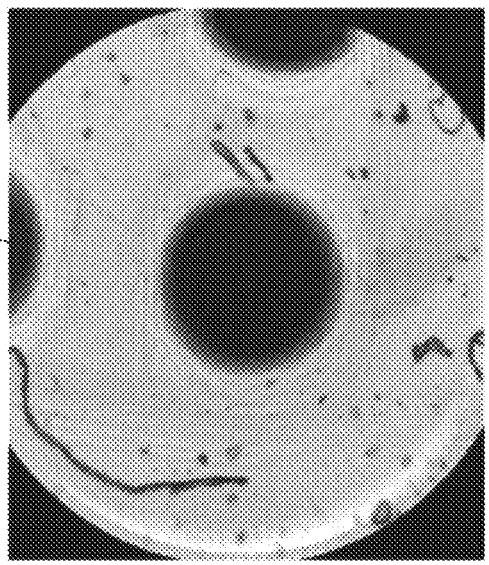
FIG. 8B is a front view of second captured image data.

In this embodiment, the number of needle-like recesses 14 included in the image based on the first captured image data D1 and the image based on the second captured image data D2 obtained by one imaging is one or more from a relationship of the resolution of the imaging element of the imaging portion 34 (see FIGS. 8A and 8B). Accordingly, in this embodiment, the measurement light PL in the wavelength range λ1 and the measurement light PL in the wavelength range λ2 transmitted through the aqueous drug solution 18 in the individual needle-like recesses 14 of the mold 12 are individually imaged using the imaging portion 34 while moving the mold 12 in a parallel direction (XY-axis direction) using the XYZ stage 30 described above. Thus, the first captured image data D1 and the second captured image data D2 of each needle-like recess 14 are output from the imaging portion 34 to the device body 10B.

FIG. 8A is a front view of the first captured image data D1, and FIG. 8B is a front view of the second captured image data D2. As described above, the measurement light PL in the wavelength range λ1 is light in a wavelength range that is difficult to be absorbed in the water 19 in the aqueous drug solution 18 than the measurement light PL in the wavelength range λ2, and conversely, the measurement light PL in the wavelength range λ2 is light in a wavelength range that is more strongly absorbed in the water 19 in the aqueous drug solution 18 than the measurement light PL in the wavelength range λ1. Therefore, as illustrated in FIGS. 8A and 8B, the first captured image data D1 becomes a brighter image than the second captured image data D2, and conversely, the second captured image data D2 becomes a darker image than the first captured image data D1.

Since the measurement light PL transmitted through the aqueous drug solution 18 in the needle-like recess 14 is absorbed in the water 19 in the aqueous drug solution 18 between the measurement light PL in the wavelength range λ1 and the measurement light PL in the wavelength range λ2 transmitted through the mold 12, the transmitted light intensity becomes lower than that of the measurement light PL transmitted through a region other than the aqueous drug solution 18 in the mold 12. Therefore, in the first captured image data D1 and the second captured image data D2, the region corresponding to the aqueous drug solution 18 filled in the needle-like recesses 14 becomes a dark image, and the other region becomes a bright image.

In this case, as described above, the measurement light PL transmitted through the aqueous drug solution 18 through the communication hole 31 is different from the measurement light PL transmitted through the mold 12 and the aqueous drug solution 18, and is not affected by refraction or the like at an interface between the inner surface of the needle-like recesses 14 and the aqueous drug solution 18. Therefore, the transmitted light intensity of the measurement light PL transmitted through the aqueous drug solution 18 through the communication hole 31 is higher than the transmitted light intensity of the measurement light PL transmitted through the mold 12 and the aqueous drug solution 18. As a result, within the first captured image data D1 brighter than the second captured image data D2, a central portion of the dark image corresponding to the aqueous drug solution 18, that is, a region corresponding to the communication hole 31 becomes bright (luminance is high).

Thus, within the image based on at least the first captured image data D1, the region corresponding to the communication hole 31 can be recognized. Thus, on the image based on the first captured image data D1, registration between a center of the imaging element of the imaging portion 34 and the communication hole 31 that is a center of the needle-like recess 14 can be performed.

Since optical absorption of the measurement light PL in a region (silicon rubber region) other than the aqueous drug solution 18 in the needle-like recesses 14 of the mold 12 is very small, brightness (luminance) of the region other than the aqueous drug solution 18 in the first captured image data D1 and the second captured image data D2 is the same or substantially the same.

<Configuration of Device Body of First Embodiment>

Figure 9:
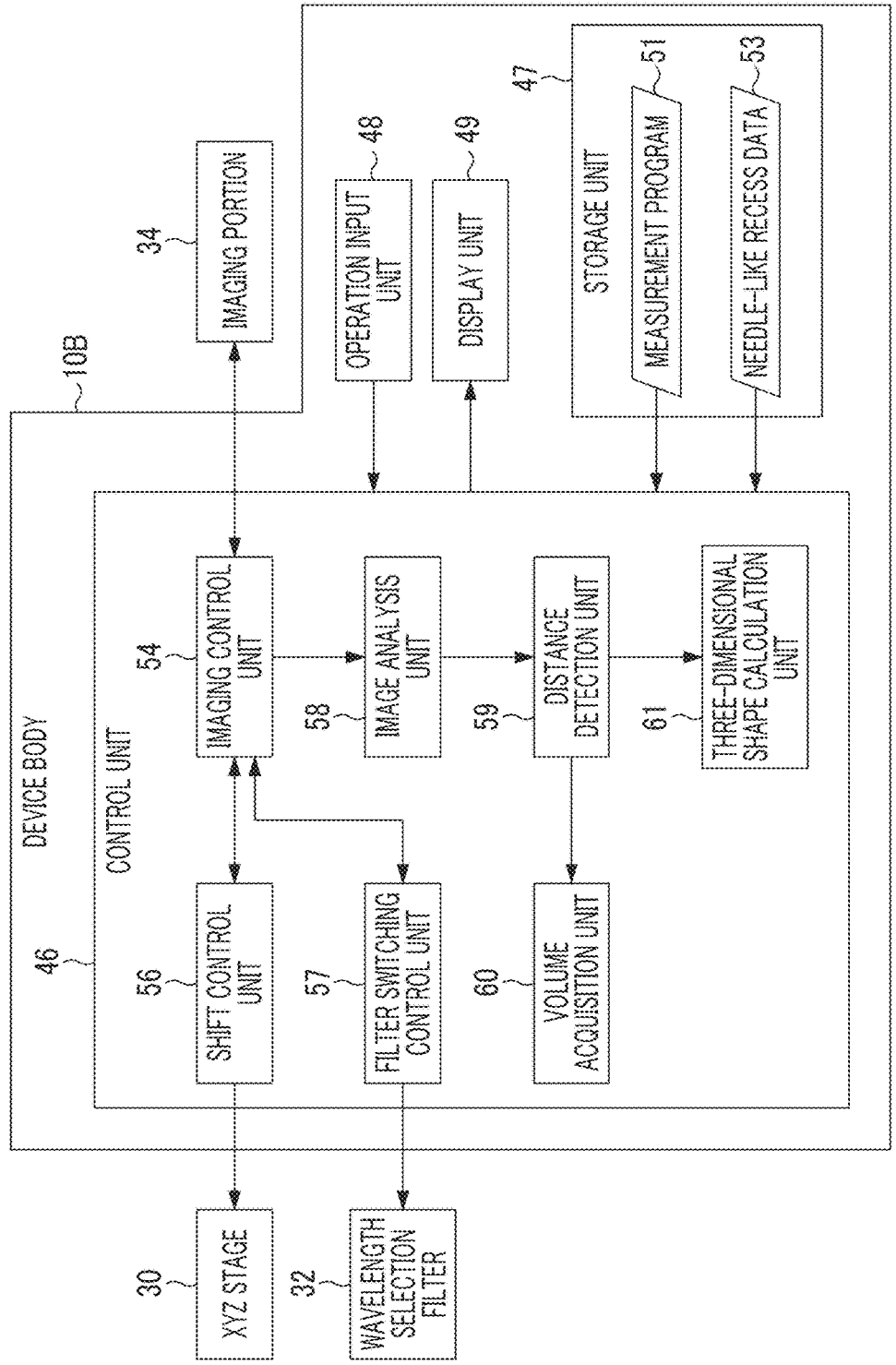
FIG. 9 is a block diagram illustrating a configuration of a device body according to the first embodiment.

FIG. 9 is a block diagram illustrating a configuration of the device body 10B of the first embodiment. The device body 10B detects the distance H of the transmitted light emitted from each position of the drug surface 18a within each needle-like recess 14 on the basis of the first captured image data D1 and the second captured image data D2 of each needle-like recess 14 of the mold 12 input from the imaging portion 34, and detects the volume of the aqueous drug solution 18 in each needle-like recess 14 on the basis of the result of the detection of the distance H.

As illustrated in FIG. 9, the device body 10B roughly includes a control unit 46, a storage unit 47, an operation input unit 48, and a display unit 49.

The control unit 46 includes various calculation units or processing units including, for example, a central processing unit (CPU), and executes various programs or information read from the storage unit 47 on the basis of a control signal from the operation input unit 48 to generally control the entire measurement device 10 including the imaging unit 10A. Further, the control unit 46 calculates the volume of the aqueous drug solution 18 in each needle-like recess 14, a three-dimensional shape of the drug surface 18a, or the like, which will be described below in detail.

Various types of information including a measurement program 51 and a needle-like recess data 53 are stored in the storage unit 47. The measurement program 51 corresponds to the program of the present invention, and causes the control unit 46 (a computer of the measurement device 10) to function as means for measuring the volume of the aqueous drug solution 18 in each needle-like recess 14.

The needle-like recess data 53 includes position information of each of the needle-like recesses 14 formed in an array form in the mold 12, and shape information (including a size) of the needle-like recess 14. As the needle-like recess data 53, data obtained by measuring each piece of information using a known method in advance may be used or data measured by a manufacturer of the mold 12 in advance may be used.

The operation input unit 48 is used, for example, for an operation of starting the measurement of the volume of the aqueous drug solution 18. Further, the display unit 49 is, for example, a liquid crystal display, and displays a result of calculating the volume of the aqueous drug solution 18 in the control unit 46.

<Configuration of Control Unit>

The control unit 46 executes the measurement program 51 read from the storage unit 47 to function as an imaging control unit 54, a shift control unit 56, a filter switching control unit 57, an image analysis unit 58, a distance detection unit 59, a volume acquisition unit 60, and a three-dimensional shape calculation unit 61 which correspond to an acquisition unit of the present invention.

The imaging control unit 54 makes a wired or wireless connection (including a connection via a communication network such as the Internet) to the imaging portion 34. This imaging control unit 54 controls imaging of the measurement light PL performed by an imaging element of the imaging portion 34.

Specifically, the imaging control unit 54 causes the imaging portion 34 to execute imaging in a state in which a center of the imaging element of the imaging portion 34 and a center of the needle-like recess 14 that is an imaging target coincide (including substantially coincide) with each other and the measurement light PL in the wavelength range $\lambda 1$ is formed as an image on an imaging surface of the imaging element. In this case, the imaging control unit 54 acquires the first captured image data D1 from the imaging portion 34. Further, the imaging control unit 54 causes the imaging portion 34 to execute imaging in a state in which the center of the imaging element of the imaging portion 34 and the center of the needle-like recess 14 that is an imaging target coincide with each other and the measurement light PL in the wavelength range $\lambda 2$ is formed as an image on an imaging surface of the imaging element. In this case, the imaging control unit 54 acquires the second captured image data D2 from the imaging portion 34. The imaging control unit 54 outputs the first captured image data D1 and the second captured image data D2 (hereinafter abbreviated as captured image data D1 and captured image data D2) acquired from the imaging portion 34 to the image analysis unit 58.

When the first interference filter 32a is set in the imaging optical path, the imaging control unit 54 causes the imaging portion 34 to execute real-time imaging for registration of the center of the imaging element of the imaging portion 34 and the communication hole 31 in the needle-like recess 14 that is the imaging target in the shift control unit 56 that will be described below. The imaging control unit 54 outputs the first captured image data D1 for registration acquired from the imaging portion 34 to the shift control unit 56.

The shift control unit 56 drives the XYZ stage 30 and performs the registration of the center of the imaging elements of the imaging portion 34 and the communication hole 31 of the needle-like recess 14 that is the imaging target on the basis of the needle-like recess data 53 in the storage unit 47 and the first captured image data D1 for registration that is input from the imaging control unit 54.

First, the shift control unit 56 acquires position information of each of the needle-like recesses 14 formed in an array form in the mold 12 (for example, position coordinates for which a corner portion of the mold 12 is a starting point) from the needle-like recess data 53, and recognizes an approximate position of each needle-like recess 14 in the mold 12. The shift control unit 56 drives the XYZ stage 30 and performs approximate registration of the center of the imaging element of the imaging portion 34 and the communication hole 31 of the first needle-like recess 14 that is the imaging target. Then, the shift control unit 56 performs accurate position adjustment of the center of the imaging element of the imaging portion 34 and the communication hole 31 of the needle-like recesses 14 that is a first imaging target on the basis of the first captured image data D1 for registration.

As illustrated in FIG. 8A described above, the region corresponding to the aqueous drug solution 18 becomes a dark image in the first captured image data D1, and the region corresponding to the communication hole 31 in the dark image is brighter than the other parts (luminance increases). Therefore, when there are the needle-like recesses 14 (the aqueous drug solution 18) in the first captured image data D1, the luminance value of the bright image corresponding to the region other than the aqueous drug solution 18 in the image is greatest, the luminance value of the dark image corresponding to the aqueous drug solution 18 is smallest, and the luminance value of the central portion of the dark image corresponding to the communication hole 31 is higher than the luminance value of the other portions of the dark image. Therefore, the shift control unit 56 can detect and compare the luminance values of all the pixels of the first captured image data D1 for registration to determine whether or not there is the communication hole 31 in the image based on the first captured image data D1, and the position can be discriminated in a case where there is the communication hole 31.

Thus, the shift control unit 56 drives the XYZ stage 30 on the basis of the determination result of the position of the communication hole 31 in the first captured image data D1, and performs registration between the center of the imaging element of the imaging portion 34 (a center of the image) and the communication hole 31 in the first needle-like recess 14.

Then, in a case where the imaging control unit 54 acquires the respective items of captured image data D1 and D2 corresponding to the first needle-like recess 14 from the imaging portion 34, the shift control unit 56 drives the XYZ stage 30 on the basis of the position information of the needle-like recesses 14, to perform registration between the center of the imaging element of the imaging portion 34 and the communication hole 31 in the second needle-like recesses 14. Since a pitch of each needle-like recess 14 is known, the registration between the center of the imaging element of the imaging portion 34 and the communication hole 31 in the second needle-like recesses 14 can be performed accurately to some extent without performing analysis of the first captured image data D1. The first captured image data D1 may be analyzed, the position of the communication hole 31 is determined, and the registration between the center of the imaging element of the imaging portion 34 and the communication hole 31 in the second needle-like recesses 14 may be performed on the basis of a result of this determination.

Thus, the shift control unit 56 drives the XYZ stage 30 each time the imaging control unit 54 acquires the respective items of captured image data D1 and D2 corresponding to the i-th needle-like recess 14 from the imaging portion 34, and performs registration between the center of the imaging element of the imaging portion 34 and the communication hole 31 in the (i+1)-th needle-like recess 14. Here, "i" is a natural number equal to or smaller than N in a case where the total number of needle-like recesses 14 formed in the mold 12 is "N". In a case where the imaging control unit 54 acquires the respective items of captured image data D1 and D2 corresponding to the N-th needle-like recess 14 from the imaging portion 34, the shift control unit 56 ends the registration. Accordingly, it is possible to individually image the measurement light PL in the wavelength range $\lambda 1$ and the measurement light PL in the wavelength range $\lambda 2$ transmitted through the individual needle-like recesses 14 (the aqueous drug solution 18) of the mold 12 using the imaging portion 34.

A method of registration between the center of the imaging element of the imaging portion 34 and the communication hole 31 in the needle-like recesses 14 of the mold 12 by the shift control unit 56 described above is an example, and the registration may be performed using another known method. Further, position adjustment in a height direction of the mold 12 by the shift control unit 56, that is, a focus adjustment method of setting an imaging focus on the first surface 12a may be performed using a known scheme, for example, on the basis of a result of discriminating marks or various traces on the first surface 12a in the image based on the first captured image data D1.

The filter switching control unit 57 controls switching of the interference filter (the first interference filter 32a and the second interference filter 32b) in which the wavelength selection filter 32 is inserted into the imaging optical path. The filter switching control unit 57 inserts the second interference filter 32b into the imaging optical path when the imaging control unit 54 acquires the first captured image data D1 (except for the first captured image data D1 for registration described above) from the imaging portion 34. Further, in a case where the imaging control unit 54 acquires the second captured image data D2 from the imaging portion 34, the filter switching control unit 57 inserts the first interference filter 32a into the imaging optical path. Thus, the measurement light PL in the wavelength range λ1 and the measurement light PL in the wavelength range λ2 can be alternately incident on each needle-like recess 14 (the aqueous drug solution 18) of the mold 12.

The image analysis unit 58 analyzes the respective items of captured image data D1 and D2 of each needle-like recess 14 input from the imaging control unit 54, and detects the transmitted light intensities in the measurement light PL of the wavelength range λ1 and the wavelength range λ2 transmitted through the aqueous drug solution 18 in the needle-like recess 14 and emitted from each position of the drug surface 18a, for each needle-like recess 14. The transmitted light intensity of each measurement light PL [corresponding to an intensity (emission intensity) of the measurement wave of the present invention] can be detected, for example, on the basis of the luminance value (luminance information) of each pixel of each of the captured image data D1 and D2. The image analysis unit 58 outputs the detection result of two types (the wavelength range λ1 and the wavelength range λ2) of transmitted light intensities of each needle-like recess 14 to the distance detection unit 59.

Thus, in this embodiment, the light source 27, the first interference filter 32a and the second interference filter 32b, the imaging portion 34, the imaging control unit 54, and the image analysis unit 58 constitute a measurement wave intensity acquisition unit of the present invention.

Figure 10:
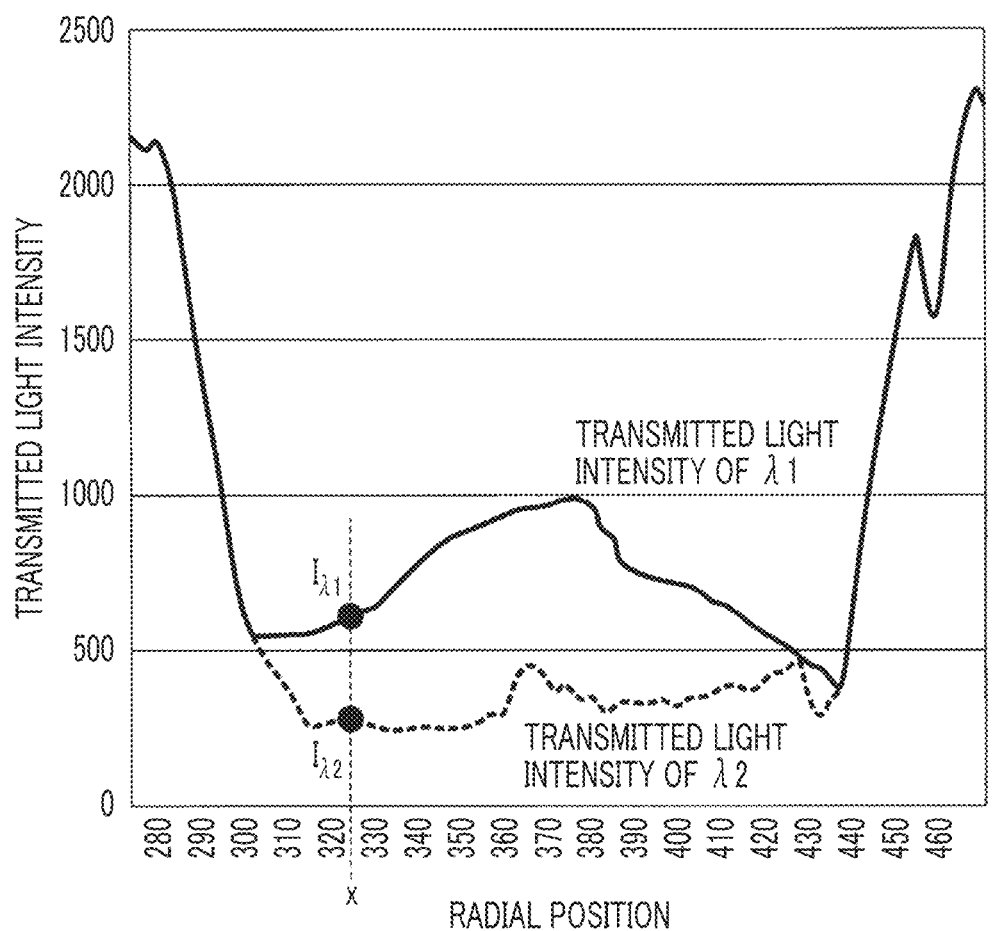
FIG. 10 is a graph showing a distribution of a transmitted light intensity of measurement light in a wavelength range $\lambda 1$ and a distribution of a transmitted light intensity of measurement light in a wavelength range $\lambda 2$ corresponding to one needle-like recess.

FIG. 10 is a graph showing a distribution (indicated by a solid line in FIG. 10, and corresponds to the intensity of the first measurement wave of the present invention) of the transmitted light intensity $I_{\lambda 1}$ of the measurement light PL in the wavelength range λ1 and a distribution (indicated by a dotted line in FIG. 10, and corresponds to the intensity of the second measurement wave of the present invention) of the transmitted light intensity $I_{\lambda 2}$ of the measurement light PL in the wavelength range λ2 corresponding to one needle-like recess 14 detected by the image analysis unit 58. A horizontal axis of this graph passes through a center in the radial direction of the needle-like recess 14 (a center of the respective items of captured image data D1 and D2 illustrated in FIGS. 8A and 8B) and indicates the radial position of the needle-like recess 14 along an arbitrary axis parallel to the second surface 12b. Accordingly, a center of the horizontal axis of the graph corresponds to the position of the communication hole 31 described above. Further, a vertical axis of the graph is a transmitted light intensity of the measurement light PL. In FIG. 10, the distribution of the transmitted light intensity is represented one-dimensionally, but an actual distribution of the transmitted light intensity obtained by analyzing respective items of the captured image data D1 and D2 is represented two-dimensionally.

The measurement light PL in the wavelength range λ1 and the measurement light PL in the wavelength range λ2 transmitted through the aqueous drug solution 18 in the needle-like recess 14 are absorbed by the water 19 contained in the aqueous drug solution 18 as described above, but the measurement light PL in the wavelength range λ2 is more easily absorbed by the water 19 than the measurement light PL in the wavelength range λ1. Therefore, as illustrated in FIG. 10, the transmitted light intensity $I_{\lambda 2}$ of the measurement light PL in the wavelength range λ2 transmitted through the aqueous drug solution 18 in the needle-like recess 14 is lower than the transmitted light intensity $I_{\lambda 1}$ of the measurement light PL in the wavelength range λ1 transmitted through the same optical path in the aqueous drug solution 18 and emitted from the drug surface 18a. Therefore, in a case where any radial position is "x", the radial position x satisfying $I_{\lambda 1} > I_{\lambda 2}$ indicates a region in which the aqueous drug solution 18 is filled in the needle-like recess 14. Therefore, the region of the drug surfaces 18a of the aqueous drug solution 18 in the needle-like recess 14 can be discriminated from a two-dimensional distribution of the transmitted light intensities $I_{\lambda 1}$ and $I_{\lambda 2}$ obtained by analyzing the respective items of the captured image data D1 and D2.

On the other hand, optical absorption by the water 19 contained in the aqueous drug solution 18 hardly occurs in a region (silicon rubber region) other than the aqueous drug solution 18 of the mold 12. Therefore, the transmitted light intensities of the measurement light PL in the wavelength range λ1 and the measurement light PL in the wavelength range λ2 emitted from the same position of the mold 12 through the same optical path in this region are substantially the same size. Therefore, the radial position x satisfying $I_{\lambda 1} \approx I_{\lambda 2}$ indicates a region (silicon rubber region) other than the aqueous drug solution 18 in the mold 12.

Figure 11A:
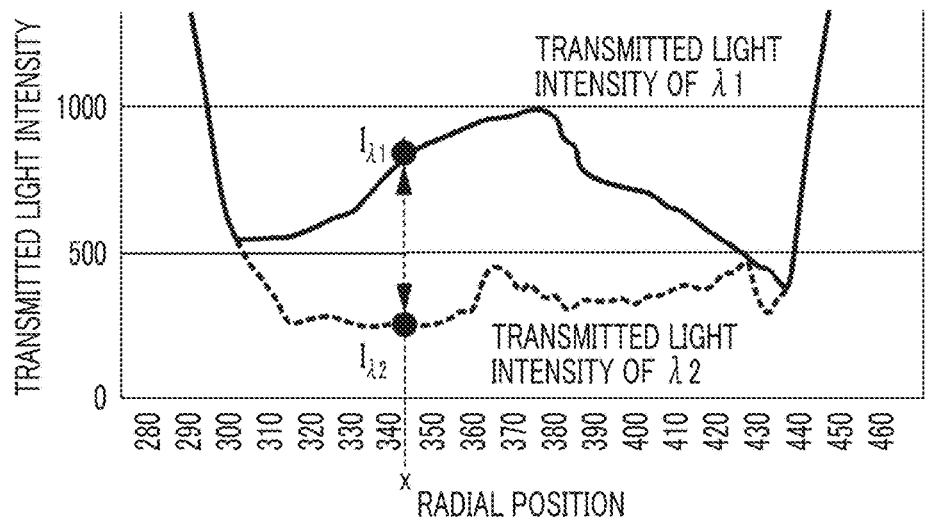
FIG. 11A is an enlarged view in which a portion of the graph illustrated in FIG. 10 is enlarged and displayed.
Figure 11B:
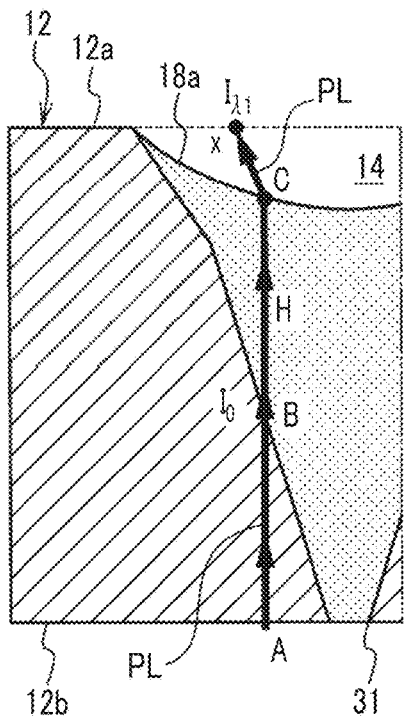
FIG. 11B is an illustrative diagram illustrating an optical path in the mold of measurement light in a wavelength ranges $\lambda 1$ incident on a radial position x illustrated in FIG. 11A.
Figure 11C:
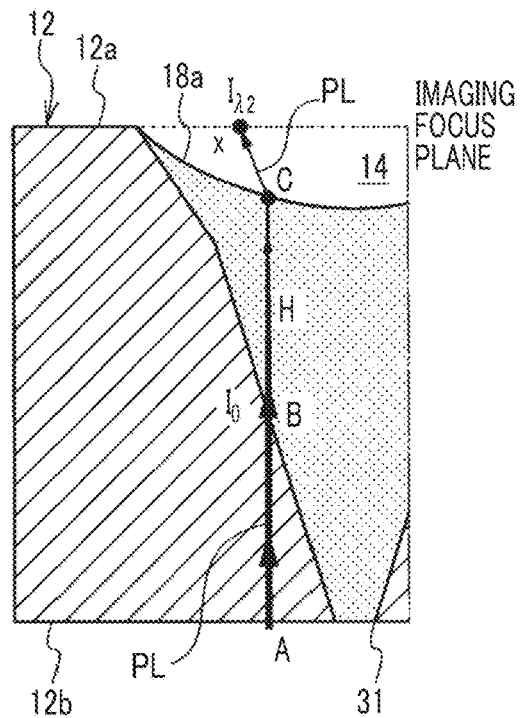
FIG. 11C is an illustrative diagram illustrating an optical path in the mold of the measurement light in a wavelength range $\lambda 2$ incident on the radial position x illustrated in FIG. 11A.

FIG. 11A is an enlarged view in which a portion of the graph illustrated in FIG. 10 is enlarged and displayed. FIG. 11B is an illustrative diagram illustrating an optical path in the mold 12 (including the aqueous drug solution 18 in the needle-like recess 14) of the measurement light PL in the wavelength ranges X1 incident on a radial position x illustrated in FIG. 11A. FIG. 11C is an illustrative diagram illustrating an optical path in the mold 12 of the measurement light PL in a wavelength range λ2 incident on the radial position x illustrated in FIG. 11A. "$I_0$" in FIGS. 11A to 11C indicate the intensity (incident light intensity) of the measurement light PL in the wavelength range λ1 and the measurement light PL in the wavelength range λ2 incident on the mold 12, "H" indicates a distance by which the measurement light PL in the wavelength range λ1 and the measurement light PL in the wavelength range λ2 are transmitted through the aqueous drug solution 18, and $I_0$ and H are basically the same as $I_0$ and H in [General Formula 1] described above.

As illustrated in FIGS. 11A and 11C, the measurement light PL in the wavelength range λ1 and the wavelength range λ2 incident on the same (including substantially the same) position A in the second surface 12b of the mold 12 directly proceeds straight in the silicon rubber region of the mold 12 toward the first surface 12a, and is incident on the same position B at an interface between the inner surface of the needle-like recess 14 and the aqueous drug solution 18.

In this case, since the refractive index (about 1.40 to 1.50) of the silicon rubber becomes a value close to the refractive index (about 1.35 to 1.50) of the aqueous drug solution 18, refraction angles of the measurement light PL in the wavelength range λ1 and the measurement light PL in the wavelength range λ2 respectively refracted at the position B becomes small. Therefore, the measurement light PL in the wavelength range λ1 and the measurement light PL in the wavelength range λ2 incident on the position B respectively proceed substantially straight toward the first surface 12a in the aqueous drug solution 18 and are incident on the same position C in the drug surface 18a.

The measurement light PL in the wavelength range λ1 and the measurement light PL in the wavelength range λ2 incident on the position C are refracted on the drug surface 18a (that is, an interface between the aqueous drug solution 18 and air) and are emitted from the drug surface 18a as the measurement light PL in the wavelength range λ1 and the measurement light PL in the wavelength range λ2. The measurement light PL in the wavelength range λ1 and the measurement light PL in the wavelength range λ2 emitted from the position C are incident on the radial position x and are imaged by the imaging portion 34 of which an imaging focus is set on the first surface 12a that is an imaging focal plane.

Here, the measurement light PL in the wavelength range λ1 and the measurement light PL in the wavelength range λ2 are refracted at the position C of the drug surface 18a. The wavelength range λ1 and the wavelength range λ2 are close wavelength ranges (for example, a difference between wavelengths of both of the wavelength ranges<100 nm to 200 nm), and refractive angles of the light emitted from the position C are substantially the same. Therefore, the measurement light PL in the wavelength range λ1 and the measurement light PL in the wavelength range λ2 emitted from the position C are incident on the radial position x described above, that is, substantially the same position in the imaging focal plane.

Therefore, the measurement light PL in the wavelength range λ1 indicating the transmitted light intensity $I_{\lambda 1}$ and the measurement light PL in the wavelength range λ2 indicating the transmitted light intensity $I_{\lambda 2}$ incident on the radial position x refer to light passing through the same optical path in the mold 12 (the aqueous drug solution 18 in the needle-like recess 14). That is, the distances H by which both of the measurement light PL are transmitted through the aqueous drug solution 18 are the same.

Since the optical absorption in the silicon rubber region of the mold 12 is very less, a difference between the transmitted light intensity $I_{\lambda 1}$ and the transmitted light intensity $I_{\lambda 2}$ in the radial position x is caused by only a difference in optical absorption between both of the measurement light PL by the water 19 contained in the aqueous drug solution 18. Therefore, when the distances H by which both of measurement light PL are transmitted through the aqueous drug solution 18 increase, the difference between the transmitted light intensity $I_{\lambda 1}$ and the transmitted light intensity $I_{\lambda 2}$ increases. Therefore, the transmitted light intensity $I_{\lambda 1}$ and the transmitted light intensity $I_{\lambda 2}$ indicate the distances H by which both of the measurement light PL emitted from the position C in the drug surface 18a are transmitted through the aqueous drug solution 18. As a result, by detecting the transmitted light intensity $I_{\lambda 1}$ and the transmitted light intensity $I_{\lambda 2}$ for each pixel from the captured image data D1 and D2, the distance H between the position B and the position C at each position in the drug surface 18a can be detected. This distance H indicates a liquid surface height at each position of the drug surface 18a (for example, a liquid surface height with reference to the second surface 12b) if the shape information of the needle-like recesses 14 is known on the basis of the needle-like recess data 53.

The distance H at each position in the drug surface 18a can be more accurately detected as described above in a case where the light source 27 is arranged on the second surface 12b side of the mold 12 and the imaging portion 34 is arranged on the first surface 12a side. In a case where a positional relationship of the light source 27 and the imaging portion 34 is reversed, accuracy of detection of the distance H between the position B and the position C is lower than in the case illustrated in FIGS. 11A to 11C.

FIG. 12A is an illustrative diagram illustrating an optical path of a comparative example in which the measurement light PL in the wavelength range λ1 is transmitted through the aqueous drug solution 18 in the needle-like recess 14 in a case where the positional relationship between the light source 27 and the imaging portion 34 is reversed from this embodiment. Further, FIG. 12B is an illustrative diagram illustrating an optical path of a comparative example in which the measurement light PL in the wavelength range λ2 is transmitted through the aqueous drug solution 18 in the needle-like recess 14 in a case where the positional relationship between the light source 27 and the imaging portion 34 is reversed.

As illustrated in FIGS. 12A and 12B, the measurement light PL in the wavelength range λ1 and the measurement light PL in the wavelength range λ2 vertically incident on the same position $B_X$ of the drug surface 18a from the same position $A_X$ on the drug surface 18a are refracted by the drug surface 18a, are incident on substantially the same position $C_X$ of the inner surface of the needle-like recesses 14, proceed straight to the silicon rubber region, and then are incident on the radial position x of the second surface 12b (imaging focal plane). Accordingly, the distance H in this case is a distance between the position $B_X$ and the position $C_X$, and is not a distance between the position $B_X$ and a position $D_X$ located vertically below the position $B_X$. That is, when a positional relationship between the light source 27 and the imaging portion 34 is reversed to this embodiment, an error is generated between the distance H and a liquid surface height at each position of the drug surface 18a. Therefore, it is preferable that the light source 27 is arranged on the second surface 12b side of the mold 12, and the imaging portion 34 is arranged on the first surface 12a side, as in this embodiment.

Referring back to FIG. 9, the distance detection unit 59 detects the distance H at each position in the drug surface 18a for each needle-like recess 14 on the basis of detection results (the transmitted light intensity b and the transmitted light intensity $I_{\lambda 2}$) of two types (the wavelength range λ1 and the wavelength range λ2) of the transmitted light intensities of each needle-like recess 14. Hereinafter, the detection of the distance H in the distance detection unit 59 will be described below.

The transmitted light intensity $I_{\lambda 1}$ and the transmitted light intensity $I_{\lambda 2}$ are expressed as the following formulas in a case where the intensity of the measurement light PL in the wavelength range λ1 and the measurement light PL in the wavelength range λ2 is "$I_0$" described above, a loss when the measurement light PL in the wavelength range λ1 and the measurement light PL in the wavelength range λ2 are refracted on the drug surface 18a (an attenuation rate of the light intensity) is "η", an optical absorption coefficient of the water 19 for light in the wavelength range λ1 is "$\alpha_{\lambda 1}$", and an optical absorption coefficient of the water 19 for light in the wavelength range λ2 is "$\alpha_{\lambda 2}$".

$$I_{\lambda_1} = \eta \cdot I_o \cdot 10^{-\alpha_{\lambda_1} H} \qquad \text{[General Formula 2]}$$

$$I_{\lambda_2} = \eta \cdot I_o \cdot 10^{-\alpha_{\lambda_2} H} \qquad \text{[General Formula 3]}$$

[General Formula 4] is obtained from [General Formula 2] and [General Formula 3], and [General Formula 5] indicating a relationship between "the transmitted light intensity $I_{\lambda_1}$ and the transmitted light intensity $I_{\lambda_2}$" and "the distance H" is obtained from [General Formula 4].

$$\frac{I_{\lambda_2}}{I_{\lambda_1}} = 10^{-(\alpha_{\lambda_2} - \alpha_{\lambda_1})H} \qquad \text{[General Formula 4]}$$

$$H = \frac{\log_{10} I_{\lambda_1} - \log_{10} I_{\lambda_2}}{\alpha_{\lambda_2} - \alpha_{\lambda_1}} \qquad \text{[General Formula 5]}$$

The transmitted light intensity $I_{\lambda_1}$ and the transmitted light intensity $I_{\lambda_2}$ and the optical absorption coefficient $\alpha_{\lambda_1}$ and the optical absorption coefficient $\alpha_{\lambda_2}$ are applied to [General Formula 5], making it possible to calculate the distance H at a point (position C) in the drug surface 18a. A method of determining the optical absorption coefficient $\alpha_{\lambda_1}$ and the optical absorption coefficient $\alpha_{\lambda_2}$ will be described below.

Further, a formula for calculating the distance H on the basis of the transmitted light intensities $I_{\lambda_1}$ and $I_{\lambda_2}$ and the optical absorption coefficients $\alpha_{\lambda_1}$ and $\alpha_{\lambda_2}$ is not limited to [General Formula 5] and the distance H may be calculated using [General Formula 5A] including the transmitted light intensities $I_{\lambda_1}$ and $I_{\lambda_2}$ and the optical absorption coefficients $\alpha_{\lambda_1}$ and $\alpha_{\lambda_2}$. Further, the distance H may be calculated using [General Formula 5B] including the transmitted light intensities $I_{\lambda_1}$ and $I_{\lambda_2}$ and the parameters P affecting the transmitted light intensities $I_{\lambda_1}$ and $I_{\lambda_2}$. Here, examples of the parameter P may include the refractive index of the mold 12 for each of the measurement light PL in the wavelength range λ1 and the measurement light PL in the wavelength range λ2, in addition to the above-described optical absorption coefficients $\alpha_{\lambda_1}$ and $\alpha_{\lambda_2}$.

$$H = f[(I_{\lambda_1}), (I_{\lambda_2}), \alpha_{\lambda_1}, \alpha_{\lambda_2}] \qquad \text{[General Formula 5A]}$$

$$H = f[(I_{\lambda_1}), (I_{\lambda_2}), P] \qquad \text{[General Formula 5B]}$$

The distance detection unit 59 sequentially applies, for example, the transmitted light intensity $I_{\lambda_1}$ and the transmitted light intensity $I_{\lambda_2}$ for each pixel from the upper left pixel of each of the captured image data D1 and D2 corresponding to the first needle-like recess 14 to [General Formula 5] in a raster scan scheme and detects the distance H for each pixel. In the pixel in the region corresponding to the drug surface 18a of the captured image data D1 and D2, the distance H>0 since the transmitted light intensity $I_{\lambda_1}$>transmitted light intensity $I_{\lambda_2}$. On the other hand, in pixels in the silicon rubber region other than the drug surface 18a of the captured image data D1 and D2, the distance H=0 is detected since the transmitted light intensity $I_{\lambda_1} \approx$ transmitted light intensity $I_{\lambda_2}$. Therefore, the result of the detection of the distance H of each pixel of the respective items of captured image data D1 and D2 shows the distance H at each position of the drug surface 18a in the first needle-like recess 14.

Hereinafter, similarly, the distance detection unit 59 detects the distance H for each pixel with respect to the respective items of captured image data D1 and D2 corresponding to the second and subsequent needle-like recesses 14. Thus, the distance H at each position in the drug surface 18a can be detected for each needle-like recess 14. The distance detection unit 59 outputs the detection result of the distance H of all pixels of each needle-like recess 14 to the volume acquisition unit 60 and the three-dimensional shape calculation unit 61.

The volume acquisition unit 60 calculates, for each needle-like recess 14, a volume (capacity) of the aqueous drug solution 18 filled in the needle-like recesses 14 on the basis of the result of the detection of the distance H of all the pixels for each needle-like recess 14, to acquire the volume of the aqueous drug solution 18 in each needle-like recess 14. Specifically, the volume acquisition unit 60 adds the results of the detection of the distance H of all the pixels corresponding to the first needle-like recess 14. Since the distance H≈0 in the pixel in the silicon rubber region other than the drug surface 18a as described above, a result of addition of the distances H of all the pixels is obtained by adding the distances H at the respective positions in the drug surface 18a of the first needle-like recess 14, and corresponds to the volume $V_1$ of the aqueous drug solution 18 filled in the first needle-like recesses 14. Thus, the volume of the aqueous drug solution 18 in the first needle-like recess 14 is calculated.

Hereinafter, similarly, the volume acquisition unit 60 calculates the volume of the aqueous drug solution 18 in the second and subsequent needle-like recesses 14. Thus, the volume of the aqueous drug solution 18 filled in all the needle-like recesses 14 can be acquired. The volume acquisition unit 60 can acquire the volume of the aqueous drug solution 18 filled in one mold 12 (all the needle-like recesses 14). In a case where the volume of the aqueous drug solution 18 in the i-th needle-like recesses 14 is $V_i$, a total volume $V_{total}$ of the volume of the aqueous drug solution 18 filled in one mold 12 is expressed as follows.

$$V_{total} = \sum_{i=1}^{N} V_i \qquad \text{[General Formula 6]}$$

The volume of the aqueous drug solution 18 in each needle-like recess 14 and the total volume of the aqueous drug solution 18 in the mold 12 acquired (calculated) by the volume acquisition unit 60 are stored in the storage unit 47 as a measurement result of the volume of the aqueous drug solution 18 and displayed on the display unit 49.

The three-dimensional shape calculation unit 61 calculates the three-dimensional shape (surface shape) of the drug surface 18a of each needle-like recess 14 on the basis of the result of the detection of the distance H of all the pixels for each needle-like recess 14 which is input from the distance detection unit 59, and the needle-like recess data 53 stored in the storage unit 47. If an inner surface of the needle-like recess 14 having a smooth shape and a surface tension of the drug surface 18a are considered, a distance between the radial position x and the position C illustrated in FIGS. 11B and 11C is very small. Therefore, if the shape information of the needle-like recess 14 is known on the basis of the needle-like recess data 53 as described above, a liquid surface height at each position C of the drug surface 18a for each needle-like recess 14 (for example, a liquid surface height with reference to the second surface 12b) is determined from the result of the detection of the distance H of all the pixels for each needle-like recess 14. Therefore, the three-dimensional shape calculation unit 61 can calculate the three-dimensional shape of the drug surface 18a of each needle-like recess 14 on the basis of the detection result of the distance H of all the pixels for each needle-like recess 14 and the needle-like recess data 53.

Figure 13:
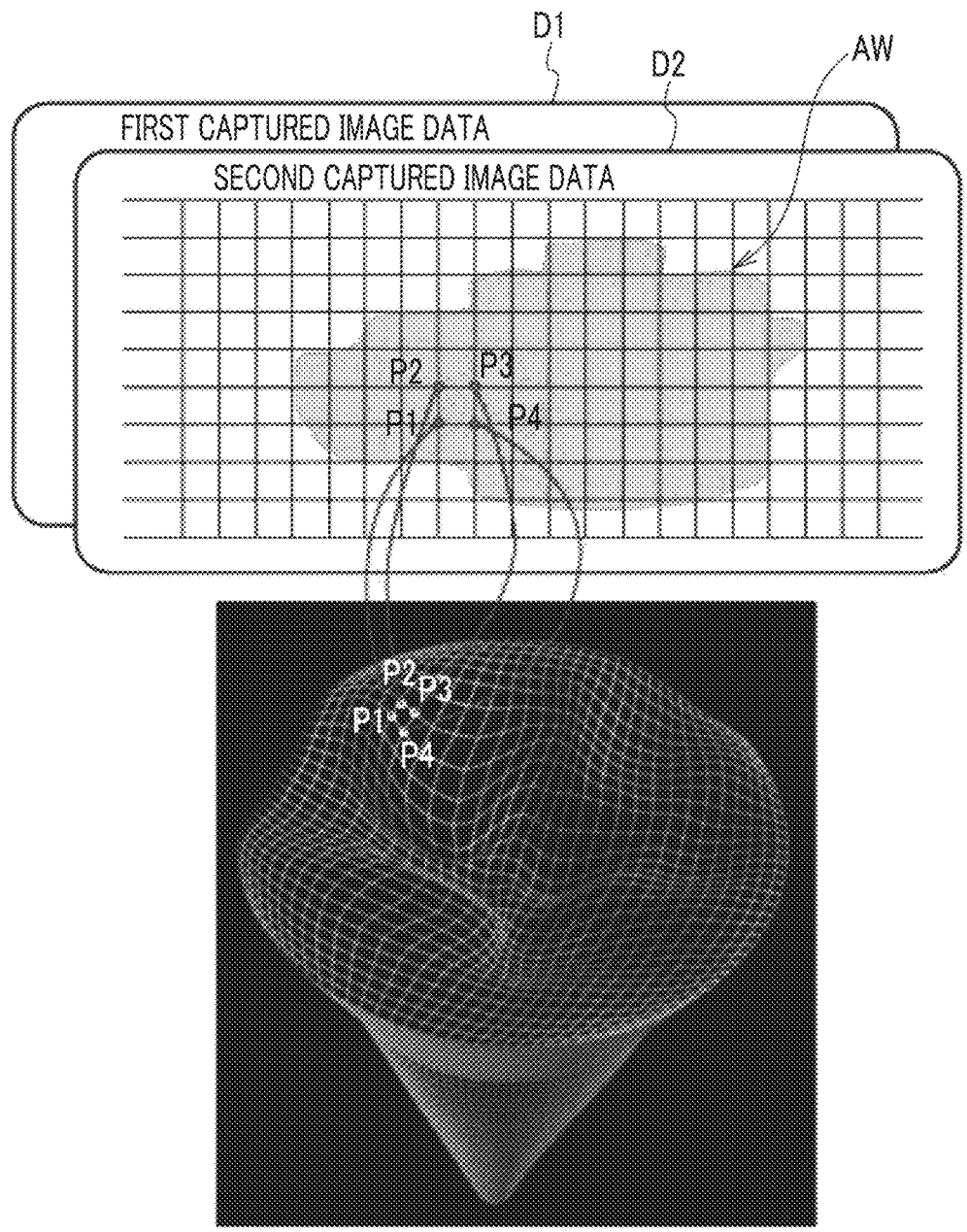
FIG. 13 is an illustrative diagram illustrating an example of a process of calculating a three-dimensional shape of a drug surface in a three-dimensional shape calculation unit.

FIG. 13 is an illustrative diagram illustrating an example of a process of calculating the three-dimensional shape of the drug surface 18a in the three-dimensional shape calculation unit 61. In FIG. 13, a region AW of each of the captured image data D1 and D2 is a region satisfying "transmitted light intensity $I_{\lambda 1}$>transmitted light intensity $I_{\lambda 2}$", that is, a region corresponding to the drug surface 18a of the needle-like recesses 14.

First, the three-dimensional shape calculation unit 61 registers coordinates of each pixel existing within the region AW of the respective items of captured image data D1 and D2 corresponding to the first needle-like recess 14, in a vertex list of a mesh illustrated in FIG. 13. Further, the three-dimensional shape calculation unit 61 calculates the liquid surface height of each pixel in the region AW (for example, a distance between positions AC illustrated in FIGS. 11B and 11C) on the basis of the shape information of the needle-like recess 14 based on the needle-like recess data 53 and the result of the detection of the distance H of all the pixels.

Then, the three-dimensional shape calculation unit 61 registers a triangle constituted by three points in the mesh with respect to vertices (the three points: p2, p3, p4 in FIG. 13) adjacent to an arbitrary vertex (p1 in FIG. 13) of the mesh. By repeatedly executing this registration process for each vertex of the mesh, a three-dimensional shape of the drug surface 18a in the first needle-like recess 14 is calculated.

Hereinafter, similarly, the three-dimensional shape calculation unit 61 also calculates the three-dimensional shape of the drug surface 18a of the second and subsequent needle-like recesses 14. Since the shape of the needle-like recess 14 is known, a three-dimensional shape of the entire aqueous drug solution 18 filled in each needle-like recess 14 can also be calculated on the basis of the three-dimensional shape of the drug surface 18a of each needle-like recess 14. A calculation result of the three-dimensional shape is stored in the storage unit 47 and displayed on the display unit 49.

[Selection of First Interference Filter (Wavelength Range λ1) and Second Interference Filter (Wavelength Range λ2)]

Next, selection of the first interference filter 32a (wavelength range λ1) and the second interference filter 32b (wavelength range λ2) will be described. As illustrated in FIGS. 5 and 6 above, the water 19 has a high optical absorbance with respect to light having a wavelength of about 1450 nm and light having a wavelength of about 1945 nm, and an optical absorbance with respect to light having a wavelength of about 1945 nm is higher than an optical absorbance with respect to light having a wavelength of about 1450 nm. In this embodiment, a wavelength range having a center wavelength of 1450 nm is defined as $\lambda_{low}$ and a wavelength range having a center wavelength of 1945 nm is defined as $\lambda_{high}$.

In this case, the water 19 has a very high optical absorbance for the light in the wavelength range $\lambda_{high}$. Accordingly, in a case where the measurement light PL in the wavelength range $\lambda_{high}$ is incident on the aqueous drug solution 18 in the needle-like recess 14, most of the measurement light PL is absorbed by the aqueous drug solution 18 according to a magnitude of the volume (distance H) of the aqueous drug solution 18. As a result, the transmitted light intensities $I_{\lambda 1}$ and $I_{\lambda 2}$ become substantially zero, and the distance H may not be calculated in [General Formula 5] or the like. Therefore, in this embodiment, according to the thickness of the mold 12 or the magnitude of the amount of filling of the aqueous drug solution 18, the wavelength range $\lambda_{high}$ is excluded as the wavelength ranges λ1 and λ2, and the wavelength ranges λ1 and λ2 are determined with reference to the wavelength range $\lambda_{low}$. Further, since the light near 1350 nm in the wavelength range $\lambda_{low}$ is also absorbed by the mold 12, an error caused by this absorption may occur at the distance H which is calculated using [General Formula 5] or the like. Therefore, in this embodiment, the wavelength near 1350 nm is excluded as the wavelength ranges λ1 and λ2.

Further, in a case where the volume of the aqueous drug solution 18 is measured on the basis of the difference between the transmitted light intensity $I_{\lambda 1}$ and the transmitted light intensity $I_{\lambda 2}$, it is preferable for the first interference filter 32a (the wavelength range λ1) and the second interference filter 32b (the wavelength range λ2) to be appropriately determined according to a thickness of the mold 12 or the volume of the aqueous drug solution 18 filled in the needle-like recesses 14 in order to increase the measurement accuracy.

Specifically, in this embodiment, in a case where a mold 12 of which the thickness (a thickness in the vertical direction with respect to the first surface 12a or the second surface 12b) is greater than a predetermined reference value, as the mold 12, is a measurement target, that is, in a case where a volume of the aqueous drug solution 18 filled in the needle-like recess 14 is large, a wavelength range $\lambda_{low}$ (near 1450 nm) that is a wavelength range in which optical absorption by the water 19 is low is selected as the wavelength range λ2 of the second interference filter 32b. Further, a wavelength range in which the optical absorbance is lower than in a wavelength range $\lambda 2=\lambda_{low}$ is determined as the wavelength range λ1 of the first interference filter 32a as described below.

On the other hand, in a case where a mold 12 of which the thickness is equal to or smaller than the predetermined reference value, as the mold 12, is a measurement target, that is, in a case where the volume of the aqueous drug solution 18 filled in the needle-like recess 14 is small, the wavelength range $\lambda_{high}$ (near 1945 nm) in which the optical absorption by the water 19 is high is selected as the wavelength range λ2 of the second interference filter 32b. Further, a wavelength range in which the optical absorbance is lower than in a wavelength range $\lambda 2=\lambda_{high}$ is determined as the wavelength range λ1 of the first interference filter 32a. In a case where the volume of the aqueous drug solution 18 is small, even when the measurement light PL in the wavelength range in which optical absorption by the water 19 is low is incident on the aqueous drug solution 18, the transmitted light intensity $I_{\lambda 1}$≈transmitted light intensity $I_{\lambda 2}$ since optical absorption by the aqueous drug solution 18 is small, and the distance H may not be calculated in [General Formula 5] or the like. Therefore, in a case where the volume of the aqueous drug solution 18 is small, the wavelength range $\lambda_{high}$ (near 1945 nm) is selected as the wavelength range λ2 of the second interference filter 32b, and the transmitted light intensity $I_{\lambda 1}$>transmitted light intensity $I_{\lambda 2}$. Therefore, the distance H can be calculated.

Further, even when the thickness of the mold 12 is the same, the wavelength ranges λ1 and λ2 may be determined from a plurality of specific wavelength ranges such as the wavelength range $\lambda_{high}$ or the wavelength range $\lambda_{low}$ light-absorbed by the water 19, which are a plurality of specific wavelength ranges in which optical absorbances are different, according to the amount of filling of the aqueous drug solution 18 filled in each needle-like recess 14 (the volume of the aqueous drug solution 18 immediately after filling).

For example, in a case where the amount of filling of the aqueous drug solution 18 filled in the needle-like recess 14 is larger than a predetermined reference, the volume in the needle-like recess 14 at the time of the measurement increases. Accordingly, in this case, after the wavelength range $\lambda_{low}$ (about 1450 nm) is selected as the wavelength range $\lambda 2$ of the second interference filter 32b, the wavelength range $\lambda 1$ of the first interference filter 32a is selected. Further, when the amount of filling of the aqueous drug solution 18 filled in the needle-like recess 14 is smaller than the predetermined reference, the volume in the needle-like recess 14 at the time of the measurement decreases. Accordingly, in this case, after the wavelength range $\lambda_{high}$ (about 1945 nm) is selected as the wavelength range $\lambda 2$ of the second interference filter 32b, the wavelength range $\lambda 1$ of the first interference filter 32a is selected.

The calculation of the distance H can be reliably performed by determining appropriate wavelength ranges as the wavelength ranges $\lambda 1$ and $\lambda 2$ from among a plurality of specific wavelength ranges light-absorbed by the water 19 according to a thickness of the mold 12 or the amount of filling (volume) of the aqueous drug solution 18 in the needle-like recesses 14 in this manner.

In a case where the wavelength range $\lambda 2$ of the second interference filter 32b is selected, selection of the wavelength range $\lambda 1$ of the first interference filter 32a suitable for this wavelength range $\lambda 2$ is performed. It is preferable that the wavelength range $\lambda 1$ is a wavelength range near the wavelength range $\lambda 2$ since the wavelength range $\lambda 1$ does not cause chromatic dispersion, is a wavelength range in which light emission luminance of the light source 27 increases so that transmitted light intensity $I_{\lambda 1}$ increases, and is a wavelength range in which an optical absorbance of light by the water 19 is low.

Here, in the chromatic dispersion, a refractive index of substance that transmits and refracts rays does not generally constant and is different according to a wavelength (frequency) of the rays. It is preferable that the light in the wavelength range $\lambda 1$ and the wavelength range $\lambda 2$ used in this embodiment has less chromatic dispersion, and optical absorption of the water 19 is different. In a case where the chromatic dispersion is less, if the two types of rays (the light in the wavelength range $\lambda 1$ and the wavelength range $\lambda 2$) are incident on the same position of the mold 12 at the same incidence angle, a ray route from the mold 12 to emission as transmitted light becomes substantially the same. In this case, since optical absorptions of the two types of rays (the light in the wavelength range $\lambda 1$ and the wavelength range $\lambda 2$) by the water 19 are greatly different, a difference in intensity of two types of transmitted light (the light in the wavelength range $\lambda 1$ and the wavelength range $\lambda 2$) emitted from the mold 12 is caused only by the difference between optical absorptions by the water 19.

Further, one important parameter indicating the characteristics of the light source 27 is an emission spectrum of the light source 27. For example, in an emission spectrum of a light emitting diode (LED) infrared light source having a center wavelength of 1450 nm (see FIG. 14B to be described below), a wavelength range of light emitted from the LED infrared light source extends from a wavelength of 1200 nm to 1600 nm.

Figure 14B:
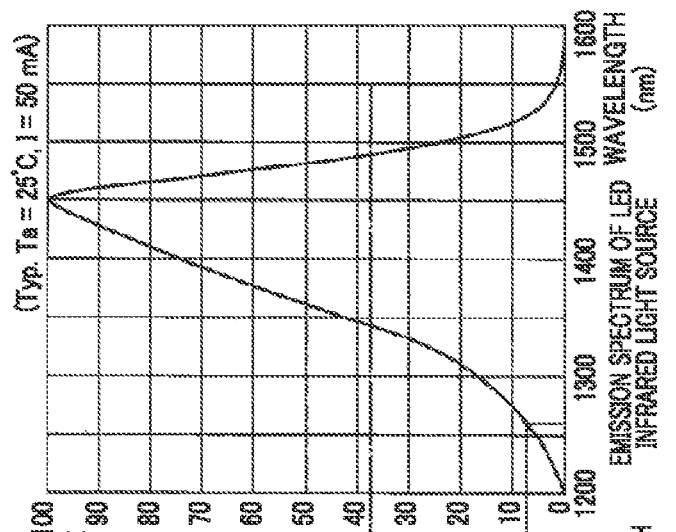
FIG. 14B is a graph illustrating an emission spectrum of the LED infrared light source used as the light source.
Figure 14A:
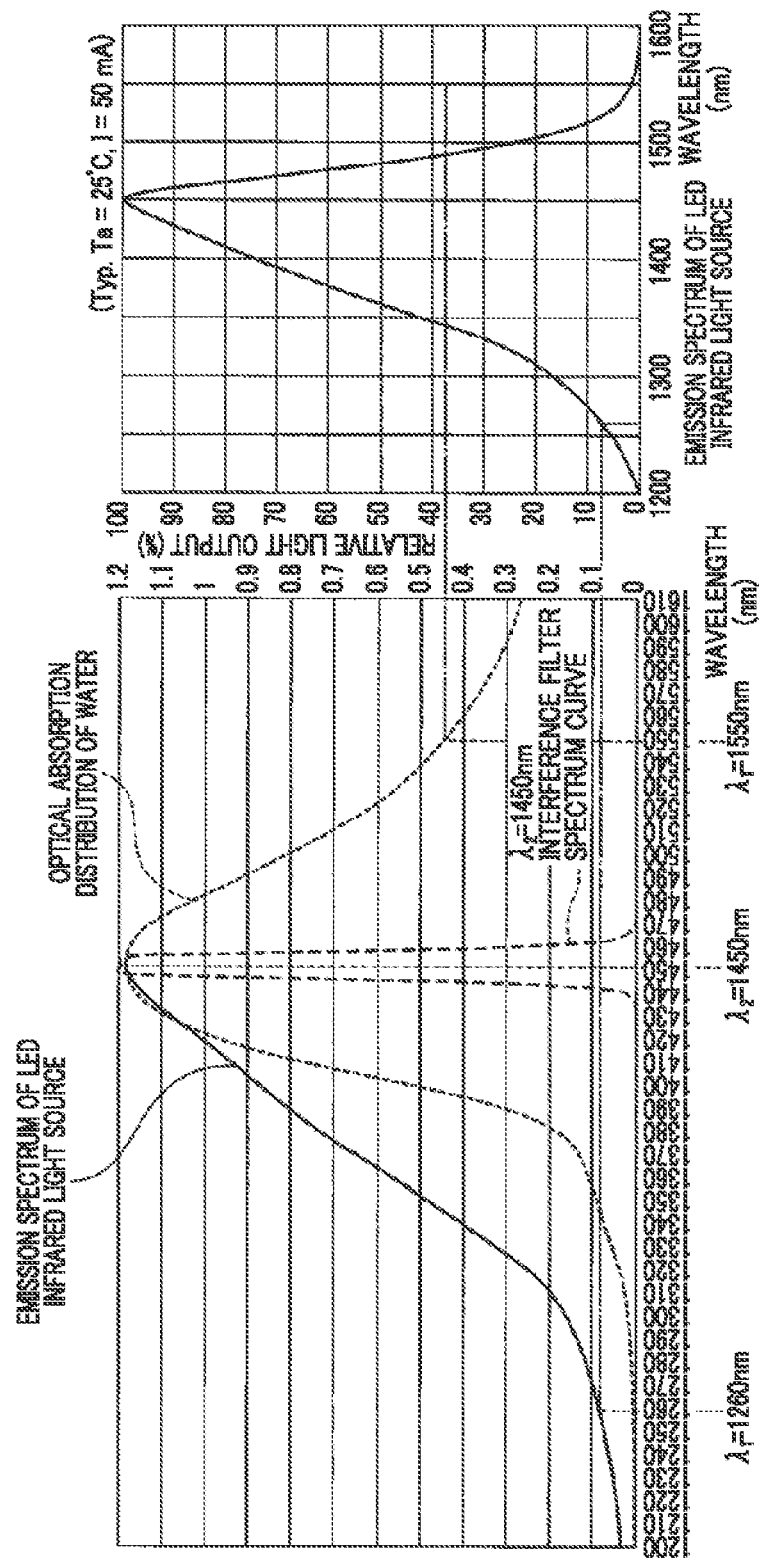
FIG. 14A is an illustrative diagram illustrating a method of selecting a wavelength range $\lambda 1$ of a first interference filter in a case where a commercially available LED infrared light source is used as a light source of a wavelength range $\lambda 2 = \lambda_{low}$.

FIG. 14A is an illustrative diagram illustrating a method of selecting the wavelength range $\lambda 1$ of the first interference filter 32a in a case where a commercially available LED infrared light source is used as the light source 27 of a wavelength range $\lambda 2=\lambda_{low}$ (1450 nm). FIG. 14B is a graph illustrating an emission spectrum of the LED infrared light source used as the light source 27. As illustrated in FIGS. 14A and 14B, in a case where the wavelength range $\lambda 2=\lambda_{low}$, 1260 nm or 1550 nm is selected as a center wavelength of the wavelength ranges $\lambda 1$ in which an optical absorption ratio by the water 19 is lower than in the wavelength range $\lambda 2$ in consideration of light emitting efficiency of the light source 27 and optical absorption by the water 19.

[Determination of Optical Absorption Coefficient $\alpha_{\lambda 1}$ and Optical Absorption Coefficient $\alpha_{\lambda 2}$]

Next, a determination of the optical absorption coefficient $\alpha_{\lambda 1}$ and the optical absorption coefficient $\alpha_{\lambda 2}$ will be described. If the measurement light PL incident on the mold 12 is single wavelength light, the optical absorption coefficients $\alpha_{\lambda 1}$ and $\alpha_{\lambda 2}$ can be easily determined on the basis of the graph illustrated in FIG. 5. However, since a bandwidth of the first interference filter 32a and the second interference filter 32b (band pass filters) is a constant width, the measurement light PL transmitted through the first interference filter 32a and the second interference filter 32b has a plurality of wavelengths rather than a single wavelength. According to an optical absorption distribution of the water 19 illustrated in FIG. 5, if the wavelength of light (the measurement light PL) changes, the optical absorption coefficient also changes. Therefore, it is preferable to totally consider the full width at half maximum FWHM of the first interference filter 32a and the second interference filter 32b or an emission spectrum of the light source 27, and the optical absorption distribution of the water 19 as the optical absorption coefficient with respect to light (measurement light PL) having a predetermined width.

Specifically, a central wavelength of the interference filter (the first interference filter 32a and the second interference filter 32b) is "$\lambda_f$" and the full width at half maximum FWHM described above is "fwhm". Since spectral characteristics of light (the measurement light PL) transmitted through the interference filter is an addition of the spectral characteristics of the light source 27 and spectral characteristics of the interference filter, the light transmitted through the interference filter is defined as light that is emitted from the "filtered light source" corresponding to a light source that emits light having the center wavelength range of $\lambda_f$ and the full width at half maximum FWHM=fwhm.

Figure 15:
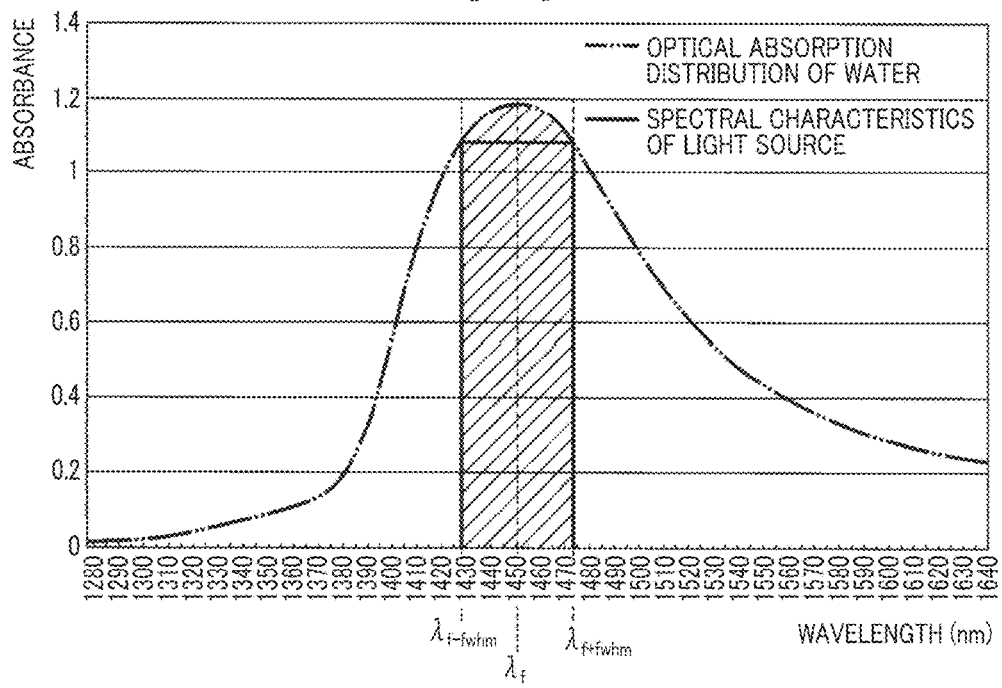
FIG. 15 is an illustrative diagram illustrating calculation of an optical absorption coefficient.

FIG. 15 illustrates calculation of the optical absorption coefficient in a case where a spectrum of the "filtered light source" is uniform at "$\lambda_f$−fwhm" and "$\lambda_f$+fwhm". In FIG. 15, a two-dot chain line indicates optical absorption distribution by the water 19, and a solid line indicates spectral characteristics of the light source 27 having a center wavelength range of $\lambda_f$ and a full width at half maximum FWHM=fmwh (filtered). For the light (the measurement light PL) emitted from the light source 27, an optical absorption coefficient $\alpha_{\lambda f}$ of the water 19 is calculated using the following formula.

$$\alpha_{\lambda_f} = \frac{\int_{\lambda_f - fwhm}^{\lambda_f + fwhm} W(\lambda) d\lambda}{2 \times fwhm} \quad \text{[General Formula 7]}$$

In [General Formula 7], $W(\lambda)$ indicates optical absorption distribution by the water 19. The optical absorption coefficient $\alpha_{\lambda f}$ is obtained by dividing an area of a hatched portion in FIG. 15 by "2×fwhm".

Figure 16:
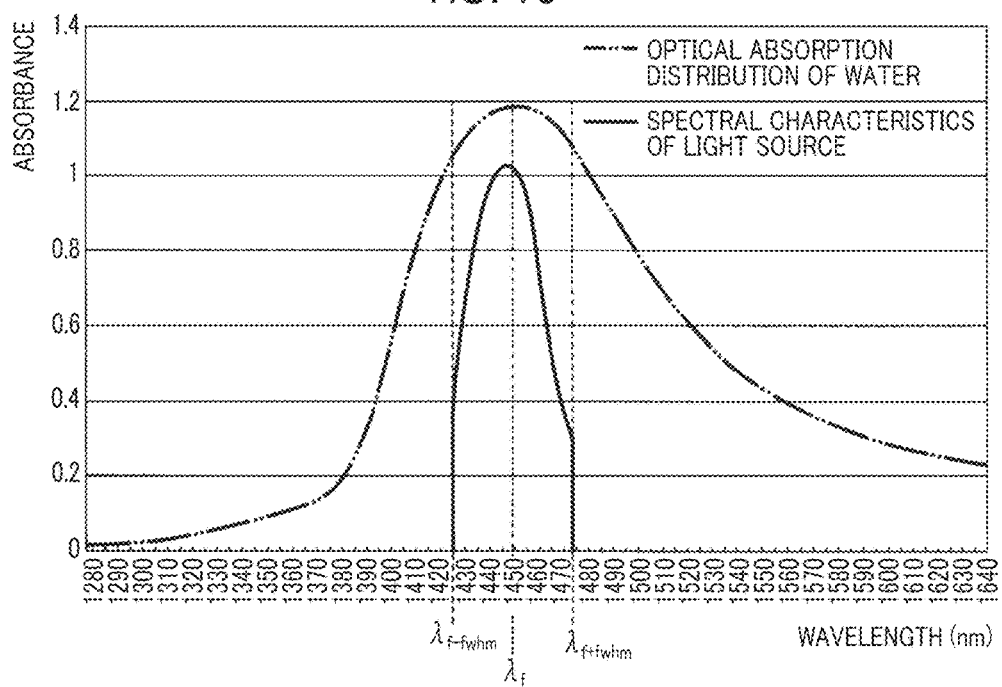
FIG. 16 is an illustrative diagram illustrating calculation of an optical absorption coefficient different from that in FIG. 15.

FIG. 16 is an illustrative diagram illustrating calculation of the optical absorption coefficient in a case where a spectrum of the "filtered light source" is not uniform at "$\lambda_f$-fwhm" and "$\lambda_f$+fwhm". In FIG. 16, a two-dot chain line indicates optical absorption distribution by the water 19, and a solid line indicates spectral characteristics of the light source 27 having a center wavelength range of $\lambda_f$ and a full width at half maximum FWHM=fmwh (filtered). For the light (the measurement light PL) emitted from the light source 27, an optical absorption coefficient $\alpha_{\lambda_f}$ of the water 19 is calculated using the following formula.

$$\alpha_{\lambda_f} = \frac{\int_{\lambda_f-fwhm}^{\lambda_f+fwhm} W(\lambda)F(\lambda)d\lambda}{\int_{\lambda_f-fwhm}^{\lambda_f+fwhm} F(\lambda)d\lambda} \qquad \text{[General Formula 8]}$$

In [General Formula 8], $W(\lambda)$ indicates the optical absorption distribution by the water 19, and $F(\lambda)$ is the spectral characteristics of the light source.

As described above, in this embodiment, the optical absorption coefficient $\alpha_{\lambda_1}$ and the optical absorption coefficient $\alpha_{\lambda_2}$ may be determined using [General Formula 7] and [General Formula 8].

[Operation of Measurement Device of First Embodiment]

Figure 17:
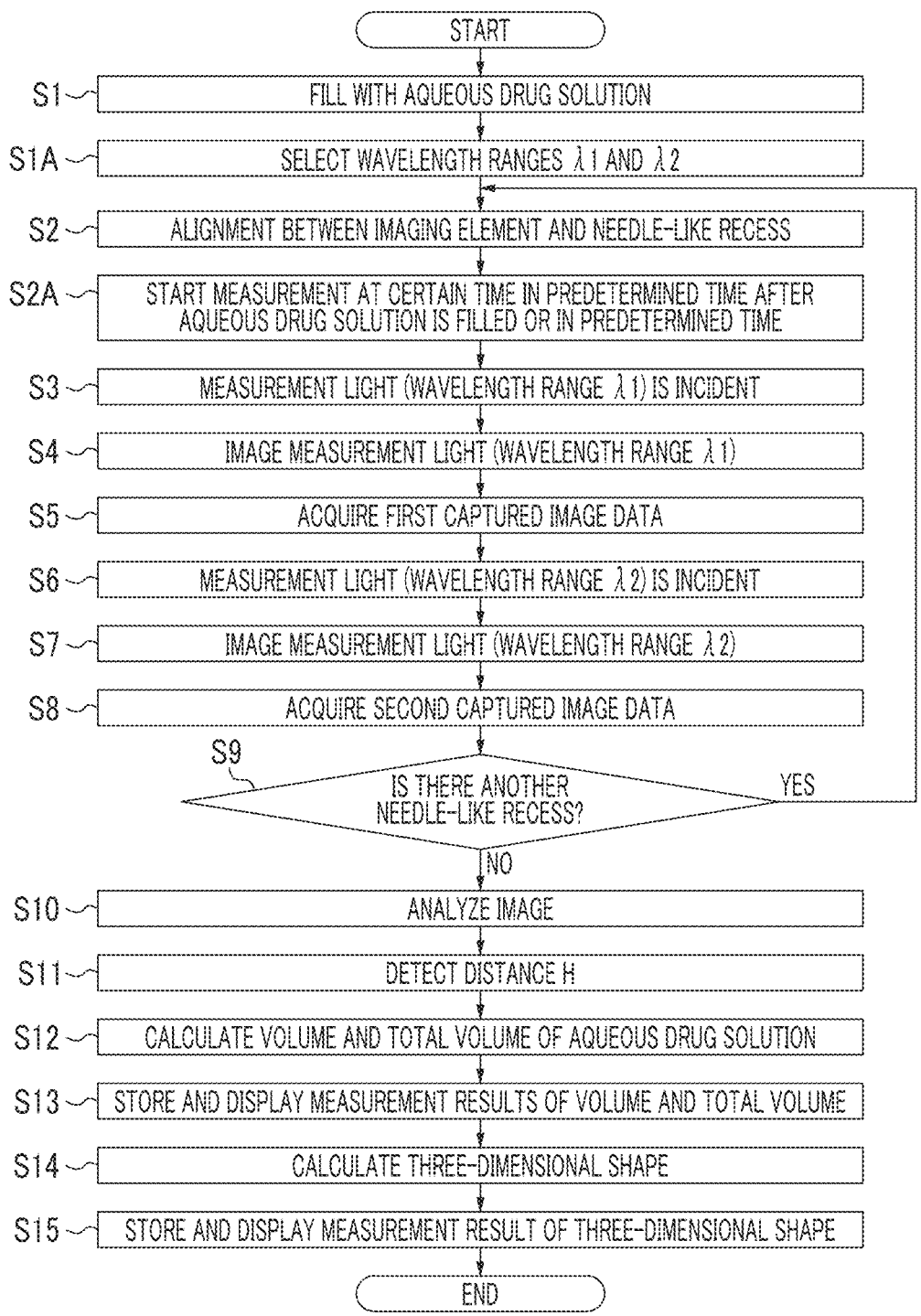
FIG. 17 is a flowchart illustrating a flow of a process of measuring a volume of an aqueous drug solution for each needle-like recess in the first embodiment.

Next, an operation of the measurement device 10 of the first embodiment having the above-described configuration, that is, a process of measuring a volume of the aqueous drug solution 18 in each needle-like recess 14 of the mold 12 (a measurement method of the present invention) will be described with reference to FIG. 17. FIG. 17 is a flowchart illustrating a flow of a process of measuring the volume of the aqueous drug solution 18 in each needle-like recess 14 in the first embodiment. Needle-like recess data 53 measured using a known scheme is stored in the storage unit 47 in advance.

As illustrated in FIG. 17, after the aqueous drug solution 18 is filled in the needle-like recess 14 of the mold 12, the mold 12 is set on the XYZ stage 30 of the measurement device 10 (step S1). Further, as described above, appropriate wavelength ranges as wavelength ranges $\lambda 1$ and $\lambda 2$ are selected from among a plurality of specific wavelength ranges in which optical absorption occurs by the water 19 in advance according to a thickness of the mold 12 or the amount of filling of the aqueous drug solution 18 filled in and the needle-like recesses 14 (step S1A).

Then, when a measurement start operation of the volume of the aqueous drug solution 18 is performed in the operation input unit 48, the shift control unit 56 of the control unit 46 recognizes approximate positions of the needle-like recesses 14 in the mold 12 on the basis of needle-like recess data 53 read from the storage unit 47. The shift control unit 56 drives the XYZ stage 30 to perform approximate registration of a center of the imaging element of the imaging portion 34 and the communication hole 31 in the first needle-like recess 14 that is an imaging target.

Further, the filter switching control unit 57 of the control unit 46 controls the wavelength selection filter 32 and inserts and arranges the first interference filter 32a into the imaging optical path (corresponding to an arrangement step of the present invention). Thereafter, the measurement light PL is emitted from the light source 27 to the second surface 12b of the mold 12. Thus, the measurement light PL in the wavelength range $\lambda 1$ is vertically incident on the second surface 12b through the first interference filter 32a, and the measurement light PL in the wavelength range $\lambda 1$ transmitted through the mold 12 is emitted from the first surface 12a. The measurement light PL in the wavelength range $\lambda 1$ is incident on the imaging surface of the imaging element of the imaging portion 34 via the imaging optical system 33.

The imaging portion 34 performs imaging of the measurement light PL in the wavelength range $\lambda 1$ formed on the imaging surface of the imaging element by the imaging optical system 33 under the control of the imaging control unit 54, and outputs first captured image data D1 for registration to the imaging control unit 54. The imaging control unit 54 outputs the first captured image data D1 for registration acquired from the imaging portion 34 to the shift control unit 56.

The shift control unit 56 analyzes the first captured image data D1 for registration (see FIG. 8A) input from the imaging control unit 54 and recognizes the position of the communication hole 31 present in the image on the basis of the first captured image data D1. Then, the shift control unit 56 drives the XYZ stage 30 and performs an accurate registration between the center of the imaging element of the imaging portion 34 and the communication hole 31 in the first needle-like recess 14 (step S2). After this registration, the measurement in the measurement device 10 is started. In this embodiment, the measurement is started at a certain time in a predetermined time after the aqueous drug solution 18 is filled in the needle-like recess 14 (for example, in 5 minutes) or in a predetermined time (step S2A). Accordingly, it is possible to start the measurement while there is no significant change in the state of the aqueous drug solution 18 filled in each needle-like recess 14. Further, by starting the measurement at a certain time in a predetermined time, measurement of the volume of the aqueous drug solution 18 in the needle-like recess 14 can be always performed under the same conditions even when the water 19 evaporates from the aqueous drug solution 18.

Then, the measurement light PL in the wavelength range $\lambda 1$ is vertically incident on the second surface 12b of the mold 12 through the first interference filter 32a (step S3, which corresponds to an incidence step of the present invention). The measurement light PL in the wavelength range $\lambda 1$ is transmitted through the aqueous drug solution 18 or the like of the first needle-like recess 14, as illustrated in FIG. 11B. Thus, the measurement light PL in the wavelength range $\lambda 1$ is emitted from, for example, the position of the drug surface 18a of the aqueous drug solution 18, and the measurement light PL in the wavelength range $\lambda 1$ is incident on the imaging surface of the imaging element of the imaging portion 34 through the imaging optical system 33.

The imaging portion 34 performs imaging of the measurement light PL in the wavelength range $\lambda 1$ formed as an image on the imaging surface of the imaging element by the imaging optical system 33, and outputs first captured image data D1 for transmitted light intensity detection to the imaging control unit 54 under control of the imaging control unit 54 (step S4). Accordingly, the imaging control unit 54 acquires the first captured image data D1 corresponding to the first needle-like recess 14 from the imaging portion 34, and outputs the first captured image data D1 to the image analysis unit 58 (step S5). The steps S4 and S5 correspond to a captured image acquisition step of the present invention.

After the imaging control unit 54 acquires the first captured image data D1 from the imaging portion 34, the filter switching control unit 57 inserts and arranges the second interference filter 32b into the imaging optical path (corresponding to an arrangement step of the present invention). Thus, the interference filter inserted into the imaging optical path is switched from the first interference filter 32a to the second interference filter 32b. The measurement light PL having the wavelength range λ2 is vertically incident on the second surface 12b of the mold 12 through the second interference filter 32b (step S6, which corresponds to an incidence step of the present invention).

The measurement light PL in the wavelength range λ2 is transmitted through the aqueous drug solution 18 of the first needle-like recess 14, or the like, as illustrated in FIG. 11C. Accordingly, the measurement light PL in the wavelength range λ2 is emitted from each position of the field drug surface 18a of the aqueous drug solution 18, or the like, and the measurement light PL in the wavelength range λ2 is incident on the imaging surface of the imaging element of the imaging portion 34 via the imaging optical system 33.

The imaging portion 34 performs imaging of the measurement light PL in the wavelength range λ2 formed as an image on the imaging surface of the imaging element by the imaging optical system 33, and outputs second captured image data D2 for transmitted light intensity detection to the imaging control unit 54 under control of the imaging control unit 54 (step S7). Accordingly, the imaging control unit 54 acquires the second captured image data D2 corresponding to the first needle-like recess 14 from the imaging portion 34, and outputs the second captured image data D2 to the image analysis unit 58 (step S8). The steps S7 and S8 correspond to a captured image acquisition step of the present invention.

Next, the shift control unit 56 drives the XYZ stage 30 on the basis of the position information (such as a pitch) of each needle-like recess 14 obtained from the needle-like recess data 53 described above, and performs registration between the center of the imaging element of the imaging portion 34 and the communication hole_31 in the second needle-like recesses 14 (YES in step S9, and step S2).

After registration between the center of the imaging element of the imaging portion 34 and the communication hole 31 in the second needle-like recesses 14, a process from steps S3 to S8 described above is repeatedly executed. Accordingly, the imaging control unit 54 acquires the respective items of captured image data D1 and D2 corresponding from the imaging portion 34 to the second needle-like recess 14, and outputs the respective items of captured image data D1 and D2 to the image analysis unit 58.

Hereinafter, similarly, the imaging control unit 54 sequentially acquires the respective items of captured image data D1 and D2 corresponding to the all needle-like recesses 14 in the mold 12 from the imaging portion 34, and outputs the captured image data D1 and D2 to the image analysis unit 58 (NO in step S9).

The image analysis unit 58 analyzes the respective items of captured image data D1 and D2 of each needle-like recess 14 input from the imaging control unit 54. Thus, as illustrated in FIG. 10, the image analysis unit 58 detects the transmitted light intensity $I_{\lambda 1}$ in the measurement light PL in the wavelength range λ1 and the transmitted light intensity $I_{\lambda 2}$ in the measurement light PL in the wavelength range λ2 transmitted through the aqueous drug solution 18 in the needle-like recess 14 and emitted from each position of the drug surface 18a, for each needle-like recess 14 (step S10, which corresponds to an image analysis step of the present invention). As a result, in the device body 10B (control unit 46), the transmitted light intensity $I_{\lambda 1}$ and the transmitted light intensity $I_{\lambda 2}$ of each needle-like recess 14 can be acquired. That is, steps S2 to S10 correspond to a measurement wave intensity acquisition step of the present invention. Then, the image analysis unit 58 outputs a result of the acquisition of the transmitted light intensities $I_{\lambda 1}$ and $I_{\lambda 2}$ of each needle-like recess 14 to the distance detection unit 59.

The distance detection unit 59 detects the distance H at each position in the drug surface 18a for each needle-like recess 14 on the basis of a detection result of the transmitted light intensities $I_{\lambda 1}$ and $I_{\lambda 2}$ for each needle-like recess 14 input from the imaging control unit 54.

First, the distance detection unit 59 sequentially applies the transmitted light intensities $I_{\lambda 1}$ and $I_{\lambda 2}$ for each pixel to [General Formula 5] from the upper left pixel of each of the captured image data D1 and D2 corresponding to the first needle-like recesses 14, and calculates the distance H for each pixel. Accordingly, the distance H at each position of the first drug surface 18a in the first needle-like recess 14 is detected.

Then, the distance detection unit 59 similarly detects the distance H of each pixel corresponding to the second and subsequent needle-like recesses 14. Accordingly, the distance H at each position in the drug surface 18a can be detected for each needle-like recess 14 (step S11, which corresponds to a distance detection step of the present invention). The distance detection unit 59 outputs the detection result of the distance H of all the pixels of each needle-like recess 14 to the volume acquisition unit (60) and the three-dimensional shape calculation unit 61.

The analysis in the image analysis unit 58 and the detection of the distance H in the distance detection unit 59 may be executed by the imaging control unit 54 acquiring the respective items of captured image data D1 and D2 corresponding to the individual needle-like recesses 14.

The volume acquisition unit 60 first adds the result of the detection of the distance H of all pixels corresponding to the first needle-like recesses 14 on the basis of the result of the detection of the distance H of all the pixels of each needle-like recess 14, and calculates the volume $V_1$ of the aqueous drug solution 18 filled in the first needle-like recesses 14.

Next, for the second and subsequent needle-like recesses 14, the volume acquisition unit 60 similarly adds results of the detection of the distance H of all the pixels for each individual needle-like recess 14 to calculate volumes $V_2$ to $V_N$ of the aqueous drug solution 18 filled in the second and subsequent needle-like recesses 14. Thus, the volume of the aqueous drug solution 18 filled in all of the needle-like recesses 14 can be individually calculated, and the volume of the aqueous drug solution 18 in each needle-like recess 14 can be acquired (step S12, which corresponds to a volume calculation step the present invention). Further, in step S12, the volume acquisition unit 60 adds the volumes $V_1$ to $V_N$ of the aqueous drug solution 18 of each needle-like recess 14 to calculate the total volume $V_{total}$ of the entire aqueous drug solution 18 filled in one mold 12. That is, steps S11 to S12 correspond to a volume acquisition step of the present invention.

The volume acquisition unit 60 outputs the calculation results (the volumes V1 to VN and the volume $V_{total}$) of the volume and the total volume of the aqueous drug solution 18 to the storage unit 47 and the display unit 49 as measurement results of the volume and the total volume of the aqueous drug solution 18. Thus, the measurement results of the volume and the total volume of the aqueous drug solution 18 are stored in the storage unit 47 and displayed on the display unit 49 (step S13; which corresponds to an acquisition result processing step of the present invention). Both of the storage and the display of the measurement results of the volume and the total volume of the aqueous drug solution 18 are not necessary to be performed, and only any one of both may be executed. Further, a display aspect and a storage (recording) aspect of the measurement results are not particularly limited.

On the other hand, the three-dimensional shape calculation unit 61 calculates a three-dimensional shape of the drug surface 18a of each needle-like recess 14 as illustrated in FIG. 13 described above on the basis of a result of the detection of the distance H of all the pixels of each needle-like recess 14 and the needle-like recess data 53 (step S14, which corresponds to the shape detection step of the present invention). Further, the three-dimensional shape calculation unit 61 calculates a three-dimensional shape of the aqueous drug solution 18 filled in each needle-like recess 14 on the basis of the three-dimensional shape of the drug surface 18a of each needle-like recess 14 and a known shape of each needle-like recess 14. A result of the calculation of the three-dimensional shape is stored in the storage unit 47 as a result of the measurement of the three-dimensional shape of each needle-like recess 14 and is displayed on the display unit 49 (step S15).

The measurement result of the volume of the aqueous drug solution 18 obtained by the measurement device 10 is fed back to the filling device that fills the aqueous drug solution 18 in the needle-like recess 14 of the mold 12. For example, the step of filling the aqueous drug solution 18 in the filling device includes an coating step of coating the first surface 12a of the mold 12 with the aqueous drug solution 18, and a step of removing an extra aqueous drug solution 18 on the first surface 12a using a brush, a scraper, or the like to form a thin film of the aqueous drug solution 18 on the first surface 12a. The coating step or the removing step is a step that affects the volume of the aqueous drug solution 18 in each needle-like recess 14. Therefore, by controlling a coating speed of the coating process or a removal rate of the removing step according to the measurement result of the volume of the aqueous drug solution 18 (a magnitude or a variation in the volume), the volume of the aqueous drug solution 18 in each needle-like recess 14 can be appropriately adjusted.

[Effects of First Embodiment]

As described above, in the measurement device 10 of the first embodiment, since the volume of the aqueous drug solution 18 in each needle-like recess 14 is measured on the basis of the two types of the captured image data D1 and D2 obtained by imaging two types of measurement light PL in different wavelength ranges transmitted through the mold 12 (the aqueous drug solution 18 in the needle-like recesses 14), it is possible to non-destructively measure the volume of the aqueous drug solution 18 in each needle-like recess 14 of the mold 12 with high precision. Further, the measurement device 10 can perform the measurement without changing a basic measurement method even when a type of drugs 16 included in the aqueous drug solution 18 is changed. Further, high-speed measurement can be performed in comparison with a method using a high-precision electronic balance of the related art.

Modification Example of First Embodiment

In the imaging unit 10A of the above embodiment, the wavelength selection filter 32 is arranged between the light source 27 and the second surface 12b of the mold 12 is arranged, but an arrangement position of the wavelength selection filter 32 is not particularly limited as long as the position is between the light source 27 and the imaging portion 34 (that is, the imaging optical path)

Figure 18:
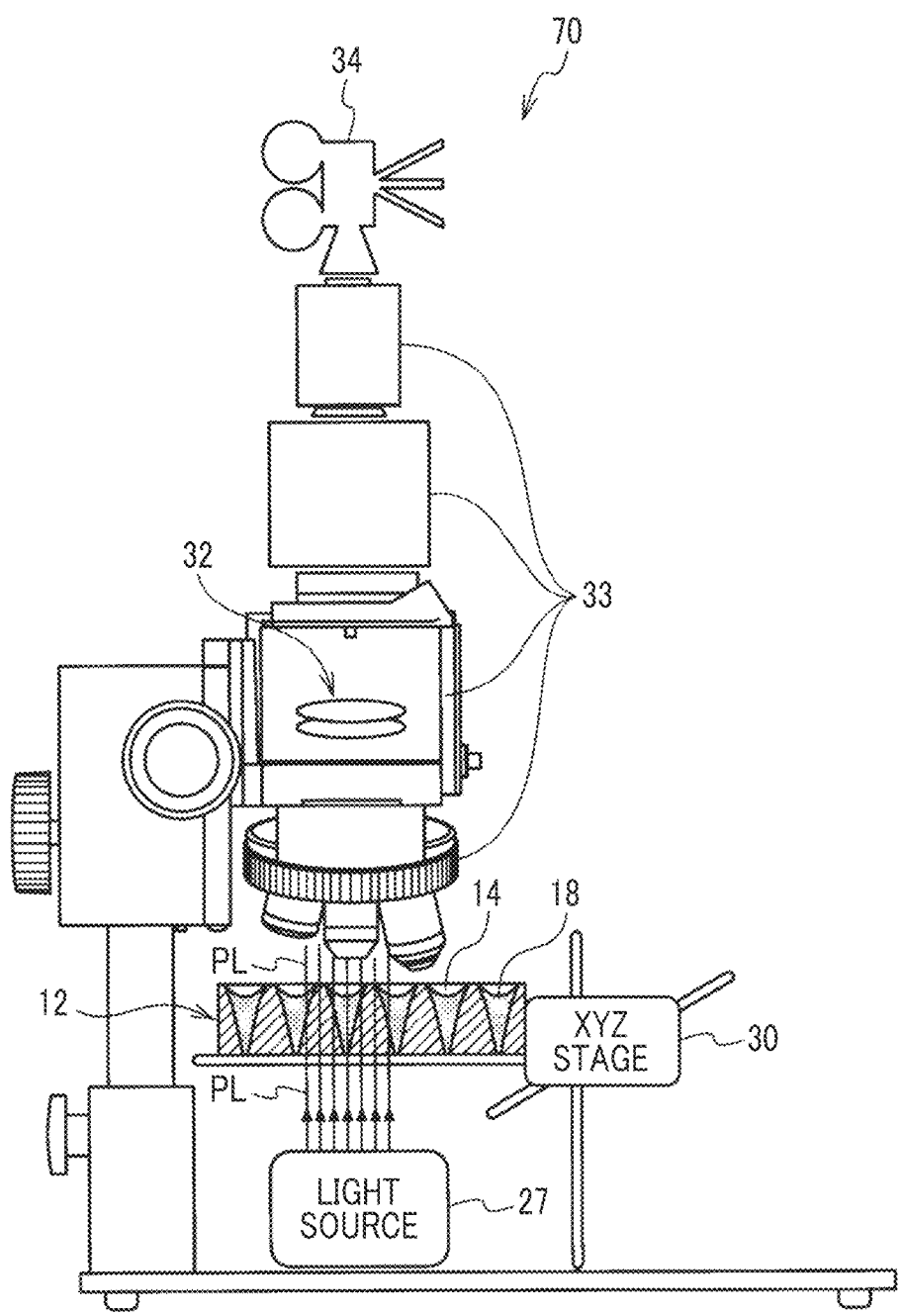
FIG. 18 is a side view of an imaging unit in which an arrangement position of a wavelength selection filter is different from the first embodiment.

FIG. 18 is a side view of the imaging unit 70 in which an arrangement position of the wavelength selection filter 32 is different from in the first embodiment. As illustrated in FIG. 18, in the imaging unit 70, the wavelength selection filter 32 is arranged inside the imaging optical system 33 (for example, the inside of a small incident light projecting tube), that is, between the light source 27 and the first surface 12a of the mold 12. In this case, since the measurement light PL in the wavelength range λ1 and the measurement light PL in the wavelength range λ2 are incident to in the imaging element of the imaging portion 34, the respective items of captured image data D1 and D2 as in the first embodiment are obtained. As a result, it is possible to measure the volume of the aqueous drug solution 18 in each needle-like recess 14, as in the first embodiment.

Although the respective needle-like recesses 14 in the mold 12 are imaged one by one from a relationship of resolution of the imaging element of the imaging portion 34 in the first embodiment, all the needle-like recesses 14 of one mold 12 can be simultaneously imaged when the resolution of the imaging element is sufficiently high.

Figure 19:
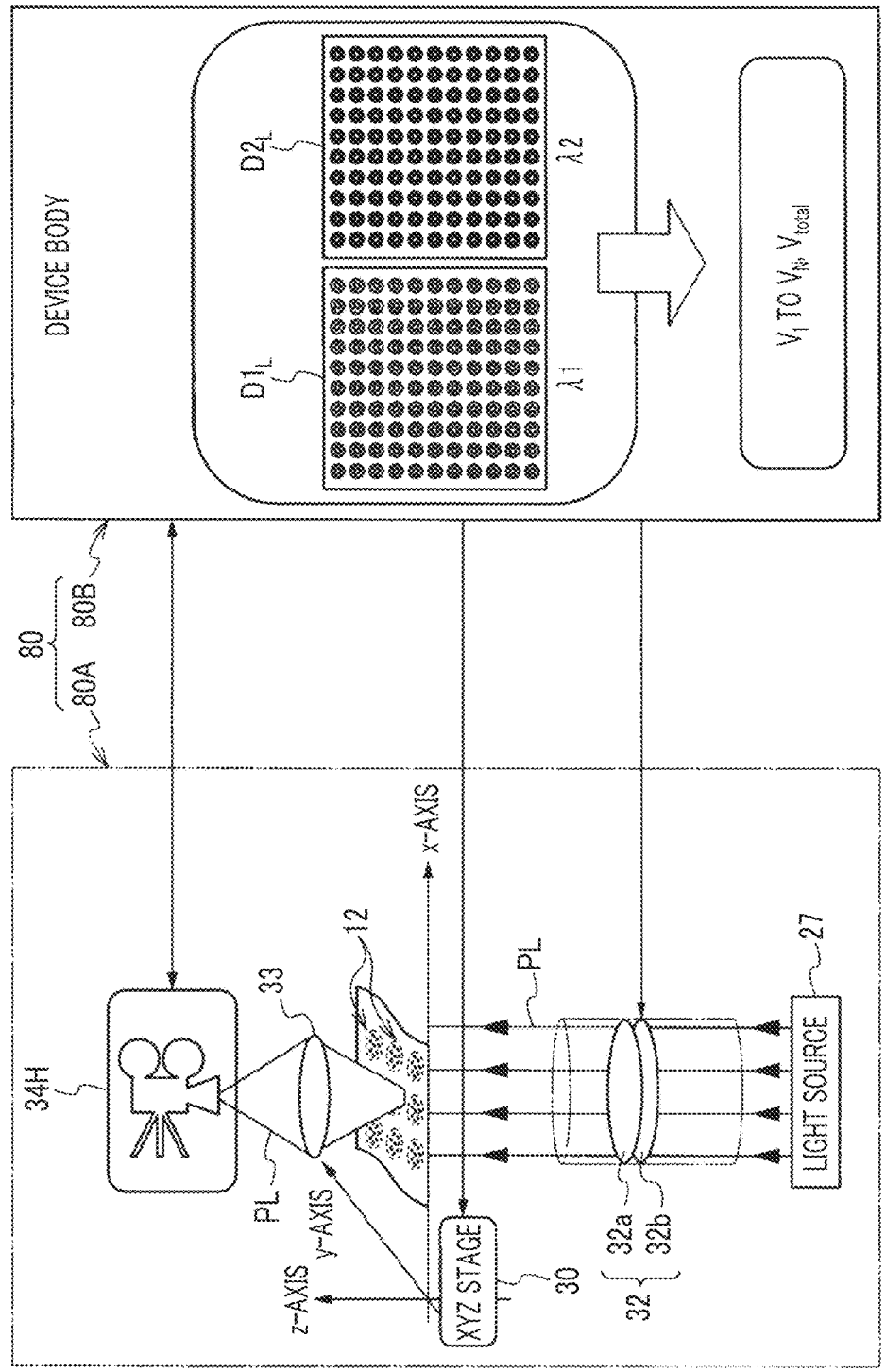
FIG. 19 is a schematic diagram of a measurement device that simultaneously images all of needle-like recesses in one mold, analyzes respective items of captured image data obtained by imaging, and calculates a volume of an aqueous drug solution in each needle-like recess.

FIG. 19 is a schematic diagram of the measurement device 80 that simultaneously images all of the needle-like recesses 14 in one mold 12, analyzes the respective items of captured image data $D1_L$ and $D2_L$ obtained by the imaging, and calculates the volume of the aqueous drug solution 18 in each needle-like recess 14.

As illustrated in FIG. 19, the measurement device 80 has basically the same configuration as the measurement device 10 in the first embodiment except that all the needle-like recesses 14 in one mold 12 are simultaneously imaged, and the first captured image data $D_{1L}$ and the second captured image data $D_{2L}$ obtained by imaging are analyzed. Thus, components having the same function or configuration as in the first embodiment are denoted with the same reference signs and description thereof will be omitted.

The measurement device 80 includes an imaging unit 80A and a device body 80B. The imaging unit 80A has basically the same configuration as the imaging unit 10A of the first embodiment except that a plurality of molds 12 are set on the XYZ stage 30 and an imaging portion 34H is included in place of the imaging portion 34 of the embodiment. However, in the imaging unit 80A, the measurement light PL is incident on the entire surface (including substantially the entire surface) of the second surface 12b of one mold 12, the measurement light PL is emitted from the entire surface of the first surface 12a, and the measurement light PL is incident on an imaging surface of the imaging element of the imaging portion 34H through the imaging optical system 33.

The imaging portion 34H includes a high-resolution imaging element capable of simultaneously imaging all the needle-like recesses 14 of the mold 12. When the first interference filter 32a is arranged in the imaging optical path by the wavelength selection filter 32, the imaging portion 34H images the measurement light PL in the wavelength range λ1 to generate the first captured image data $D1_L$, and outputs the first captured image data $D1_L$ to the device body 80B. Further, when the second interference filter 32b is arranged in the imaging optical path by the wavelength selection filter 32, the imaging portion 34H images the measurement light PL in the wavelength range λ2 to generate the second captured image data $D2_L$, and outputs the second captured image data $D2_L$ to the device body 80B.

Images of all the needle-like recesses 14 of the respective molds 12 are included in the first captured image data $D1_L$ and the second captured image data $D2_L$.

In the imaging unit 80A, after the generation and the output of respective items of captured image data D1$_L$ and D2$_L$ of one mold 12 have been completed, the XYZ stage 30 is driven, and the mold 12 that is the next imaging target is set at a measurement position (the imaging optical path). Then, the imaging unit 80A images the measurement light PL in the wavelength range λ1 and the measurement light PL in the wavelength range λ2 transmitted through the mold 12 that is the next imaging target using the imaging portion 34H, and performs generation of the captured image data D1$_L$ and D2$_L$ and output of the captured image data D1$_L$ and D2$_L$ to the device body 80B.

Hereinafter, similarly, the imaging unit 80A images the measurement light PL in the wavelength range λ1 and the measurement light PL in the wavelength range λ2 transmitted through the individual molds 12 on the XYZ stage 30 using the imaging portion 34H, and outputs respective items of captured image data D1L and D2L for each mold 12 to the device body 80B.

The device body 80B analyzes respective items of captured image data D1$_L$ and D2$_L$ of each mold 12, detects the transmitted light intensities I$_{λ1}$ and I$_{λ2}$ of each needle-like recess 14 for each mold, and then detects the distance H of all pixels of each needle-like recess 14. Then, the device body 80B calculates volumes V$_1$ to V$_N$ of the aqueous drug solutions 18 of the respective needle-like recesses 14, a total volume V$_{total}$ of the entire aqueous drug solution 18, and a three-dimensional shape of the drug surface 18a or the like in the needle-like recess 14, for each mold. Since a method of detecting the transmitted light intensities I$_{λ1}$ and I$_{λ2}$, a method of detecting the distance H, a method of calculating the volume and the total volume of the aqueous drug solution 18, and a method of calculating the three-dimensional shape are basically the same methods as in the first embodiment, specific description will not be omitted herein.

Thus, in the measurement device 80, all of the needle-like recesses 14 in the mold 12 are simultaneously imaged, the volume of the aqueous drug solution 18 in each needle-like recess 14 is measured on the basis of the captured image data D1$_L$ and D2$_L$ obtained by the imaging, and therefore, higher-speed measurement than in the first embodiment can be performed while obtaining the same effects as in the first embodiment. Thus, when the measurement device 80 is incorporated in a manufacturing process for the MNA 29, production of the efficient MNA 29 (for example, production in a Roll to Roll scheme) can be performed.

In the first embodiment, the case in which the measurement light PL in the wavelength range λ1 and the measurement light PL in the wavelength range λ2 incident on the position B respectively proceed substantially straight toward the first surface 12a in the aqueous drug solution 18 has been described (see FIGS. 11A to 11C), but the measurement light PL in the wavelength range λ1 and the measurement light PL in the wavelength range λ2 incident on the position B are refracted due to a difference between the refractive index of the silicon rubber and the refractive index of the aqueous drug solution 18. The refraction angle of each measurement light PL changes with the concentration of the drug 16 in the aqueous drug solution 18 and is up to 15°. Since this refraction angle is constant if the tilt angle of the inner surface of the needle-like recess 14 is constant, the distance H can be corrected using the following formula. In the following formula, "H$_R$" is a distance after correction, and "θ" is a refraction angle.

$$H_R = H \times \cos\theta \quad \text{[General Formula 9]}$$

Although surface treatment is not performed on the first surface 12a of the mold 12 in the first embodiment, for example, hydrophilic treatment such as Teflon (registered trademark) treatment may be performed on the first surface 12a in advance prior to filling of the aqueous drug solution 18 into the needle-like recess 14. FIG. 20A is a cross-sectional view of the mold 12 in which hydrophilic treatment is not performed on the first surface 12a, and FIG. 20B is a cross-sectional view of the mold 12 in which hydrophilic treatment is performed on the first surface 12a.

As illustrated in FIG. 20A, in the mold 12 in which hydrophilic treatment is not performed on the first surface 12a, meniscus is generated on the drug surface 18a in the needle-like recess 14. On the other hand, as illustrated in FIG. 20B, in the mold 12 in which the hydrophilic treatment is performed on the first surface 12a in advance before the drug 16 is filled in the needle-like recess 14, the meniscus is prevented from being generated on the drug surface 18a in the needle-like recess 14, and the drug surface 18a may be a plane. Thus, since the refraction angles of both the measurement light PL at the position C illustrated in FIGS. 11B and 11C can be reduced, an error of the position C (radial position x) of both the measurement light PL is reduced. As a result, it is possible to measure the volume of the aqueous drug solution 18 or the three-dimensional shape of the drug surface 18a with higher accuracy.

Although the volume acquisition unit 60 of the first embodiment calculates the volume of the aqueous drug solution 18 in the needle-like recess 14, the volume acquisition unit 60 may calculate the volume of the drug 16 contained in the aqueous drug solution 18 in the needle-like recess 14 on the basis of the calculation result of the volume of the aqueous drug solution 18 in the needle-like recess 14.

Figure 21:
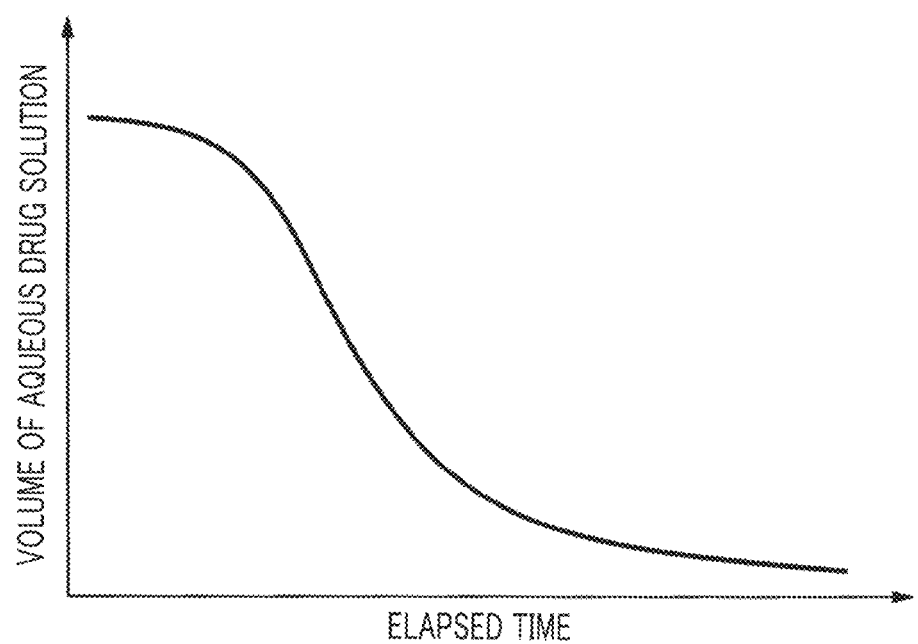
FIG. 21 is a graph illustrating a relationship between a volume of an aqueous drug solution filled in a needle-like recess and an elapsed time immediately after filling.

FIG. 21 is a graph illustrating a relationship between the volume of the aqueous drug solution 18 filled in the needle-like recess 14 and an elapsed time immediately after filling. As illustrated in FIG. 21, the volume of the aqueous drug solution 18 in the needle-like recess 14 decreases over time due to evaporation of the water 19 contained in the aqueous drug solution 18 as illustrated in FIG. 3 described above, but the volume of the drug 16 in the needle-like recess 14 does not change. Therefore, the concentration of the drug 16 in the aqueous drug solution 18 increases over time. Thus, by obtaining the temporal change in the volume of the aqueous drug solution 18 in the needle-like recess 14 as illustrated in FIG. 21, the temporal change in the concentration of the drug 16 in the aqueous drug solution 18 in the needle-like recess 14 is obtained.

By storing such a temporal change in concentration of the drug 16 in the storage unit 47 in advance, the volume acquisition unit 60 can determine the concentration of the drug 16 in the aqueous drug solution 18 in the needle-like recess 14 at the time of measurement of the volume of the aqueous drug solution 18 described above. Thus, the volume acquisition unit 60 can calculate the volume of the drug 16 in each needle-like recess 14 on the basis of the concentration of the drug 16 in the aqueous drug solution 18 and the measurement result of the volume of the aqueous drug solution 18 in each needle-like recess 14. Further, the volume acquisition unit 60 can calculate a total volume of the volume of the entire drug 16 in the mold 12. Calculation results of the volume and the total volume of the drug 16 are stored in the storage unit 47 as a measurement result of the volume and the total volume of the drug 16 and displayed on the display unit 49.

In the first embodiment, since the water 19 contained in the aqueous drug solution 18 evaporates over time after the aqueous drug solution 18 is filled in the needle-like recess 14 of the mold 12, the volume of the aqueous drug solution 18 in the needle-like recess 14 is reduced. In this case, for example, humidity around the mold 12 is adjusted to humidity of 100% (including substantially 100%) between the filling of the aqueous drug solution 18 and at least completion of the measurement in the measurement device 10, so that the evaporation of the water 19 is suppressed. Thus, a concentration of the drug 16 in the aqueous drug solution 18 is substantially constant regardless of the elapse of time, and therefore, the volume of the drug 16 can be easily determined from the measurement result of the volume of the aqueous drug solution 18. The evaporation of the water 19 may be suppressed by covering the first surface 12a of the mold 12 with a transparent lid (for example, a film) instead of adjusting the humidity around the mold 12 to humidity of 100%.

Second Embodiment

Figures 22A, 22B:
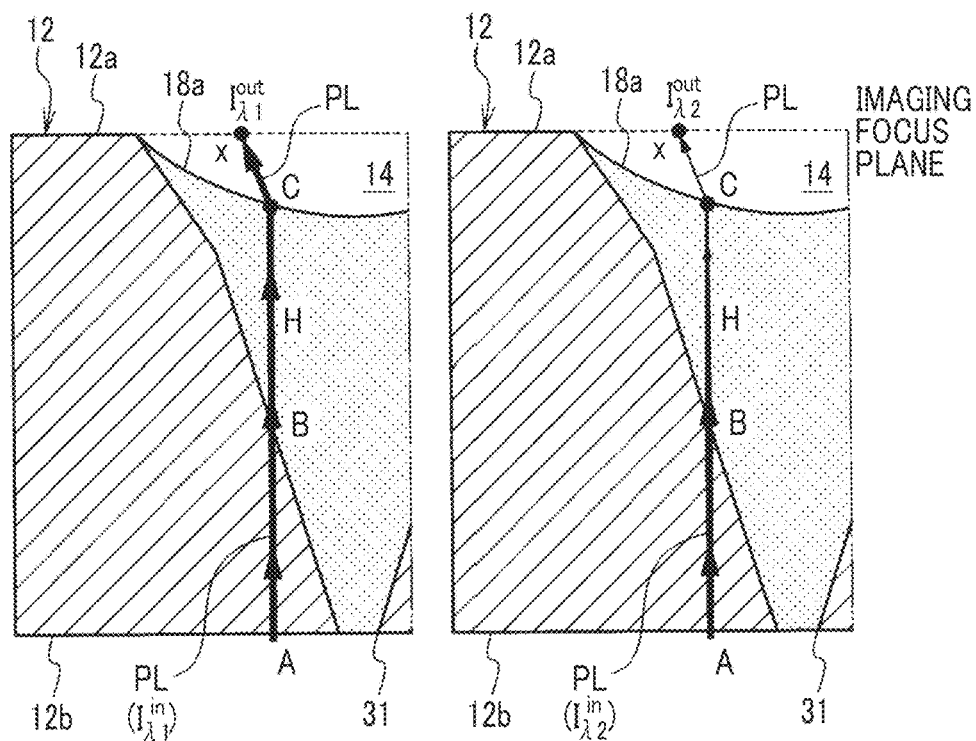
FIGS. 22A and 22B are illustrative diagrams illustrating a process of detecting a distance H in a measurement device of a second embodiment.

FIGS. 22A and 22B are illustrative diagrams illustrating a process of detecting the distance H using the measurement device 10 of a second embodiment. In the first embodiment (including the modification example thereof, hereinafter the same), as illustrated in FIGS. 11B and 11C, the distance detection unit 59 detects the distance H at each position in the drug surface 18a using [General Formula 5] on the assumption that the incident light intensities (incidence intensities) of the measurement light PL in the wavelength range λ1 and the measurement light PL in the wavelength range λ2 incident on the second surface 12b are both "$I_0$". On the other hand, the distance detection unit 59 of the second embodiment detects the distance H at each position in the drug surface 18a on the assumption that the incident light intensities (incidence intensities) of the measurement light PL in the wavelength range λ1 and the measurement light PL in the wavelength range λ2 incident on the second surface 12b are different.

Further, since the measurement device 10 of the second embodiment has basically the same configuration as the measurement device 10 in the first embodiment, components having the same function or configuration as in the first embodiment are denoted with the same reference signs and description thereof will be omitted. However, in the second embodiment, in steps S2 to S10 illustrated in FIG. 17 described above (measurement wave intensity acquisition step of the present invention), acquisitions of incident light intensities (incidence intensities) of the measurement light PL in the wavelength range λ1 and the measurement light PL in the wavelength range λ2 by the control unit 46 are performed in parallel, and the respective incident light intensities are input to the distance detection unit 59. The incident light intensity may be acquired through actual measurement or a predicted incident light intensity may be acquired.

As illustrated in FIGS. 22A and 22B, in a case where the incident light intensity of each of the measurement light PL in the wavelength range λ1 and the measurement light PL in the wavelength range λ2 incident on the second surface 12b are different, the transmitted light intensity (emission intensity) of the measurement light PL in the wavelength range λ1 is expressed by [General Formula 10] and the transmitted light intensity (emission intensity) of the measurement light PL in the wavelength range λ2 is expressed by [General Formula 11]. A loss in the following formula represents a loss due to refraction at a position (point) B and a loss of the measurement light PL due to refraction at a position (point) C.

$$I_{\lambda_1}^{out} = I_{\lambda_1}^{in} \cdot 10^{-\alpha_{\lambda_1} \cdot H} \cdot \eta_{\lambda_1}^{all} \qquad \text{[General Formula 10]}$$

$I_{\lambda_1}^{in}$: Incident light intensity of measurement light in wavelength range λ1
$I_{\lambda_1}^{out}$: Transmitted light intensity of measurement light in wavelength range λ1
$\alpha_{\lambda_1}$: Optical absorption coefficient of water corresponding to measurement light in wavelength range λ1
$\eta_{\lambda_1}^{all}$: Loss caused by refraction of measurement light in wavelength range λ1

$$I_{\lambda_2}^{out} = I_{\lambda_2}^{in} \cdot 10^{-\alpha_{\lambda_2} \cdot H} \cdot \eta_{\lambda_2}^{all} \qquad \text{[General Formula 11]}$$

$I_{\lambda_2}^{in}$: Incident light intensity of measurement light in wavelength range λ2
$I_{\lambda_2}^{out}$: Transmitted light intensity of measurement light in wavelength range λ2
$\alpha_{\lambda_2}$: Optical absorption coefficient of water corresponding to measurement light in wavelength range $\lambda_2$
$\eta_{\lambda_2}^{all}$: Loss caused by refraction of measurement light in wavelength range $\lambda_2$ Here, in a case where the wavelength range λ1 and the wavelength range λ2 are close values to each other and the optical absorption coefficient of the water 19 is set to be greatly different, a loss in [General Formula 10] and a loss in [General Formula 11] are approximated. Therefore, if the transmitted light intensity of the measurement light PL in the wavelength range λ1 in [General Formula 10] is divided by the transmitted light intensity of the measurement light PL in the wavelength range λ2 in [General Formula 11], the transmitted light intensity is expressed as shown in [General Formula 12]. From [General Formula 12], [General Formula 13] indicating a distance H at each position in the drug surface 18a is derived.

$$\frac{I_{\lambda_2}^{out}}{I_{\lambda_1}^{out}} = \frac{I_{\lambda_2}^{in}}{I_{\lambda_1}^{in}} \cdot 10^{-(\alpha_{\lambda_2} - \alpha_{\lambda_1})H} \qquad \text{[General Formula 12]}$$

$$H = -\frac{\log_{10} I_{\lambda_2}^{out} - \log_{10} I_{\lambda_1}^{out} - (\log_{10} I_{\lambda_2}^{in} - \log_{10} I_{\lambda_1}^{in})}{\alpha_{\lambda_2} - \alpha_{\lambda_1}} \qquad \text{[General Formula 13]}$$

Thus, in the second embodiment, when the incident light intensities of the measurement light PL in the wavelength range λ1 and the measurement light PL in the wavelength range λ2 are different, it is possible to accurately detect the distance H at each position of the drug surface 18a in comparison with the first embodiment using [General Formula 13]. Since subsequent processes are basically the same as in the first embodiment, description thereof will be omitted.

Third Embodiment

FIGS. 23A and 23B are illustrative diagrams illustrating a process of detecting the distance H in the measurement device 10 of the third embodiment. In each of the above embodiments, [General Formula 5] and [General Formula 13] are derived from a formula in which the transmitted light intensity of the measurement light PL in the wavelength range λ2 is divided by the transmitted light intensity of the measurement light PL in the wavelength range λ1 as shown in [General Formula 4] and [General Formula 12] to obtain the distance H. On the other hand, in the third embodiment, the distance H is obtained from a difference between the transmitted light intensity of the measurement light PL in the wavelength range λ1 and the transmitted light intensity of the measurement light PL in the wavelength range λ2 in consideration of an influence of stray light indicated by a sign "φ" (a suffix is omitted), as illustrated in FIGS. 23A and 23B. Here, the stray light is light different from the measurement light PL that is a measurement target of the distance H, and is also called a flare component.

Since the measurement device 10 of the third embodiment has basically the same configuration of the measurement device 10 of each of the above embodiments, components having the same function or configuration as in each of the above embodiments are denoted with the same reference signs and description thereof will be omitted.

When an influence of stray light is considered, the transmitted light intensity of the measurement light PL in the wavelength range λ1 is represented using [General Formula 14] and the transmitted light intensity of the measurement light PL in the wavelength range λ2 is expressed using [General Formula 15]. A difference between the transmitted light intensity of the measurement light PL in the wavelength range λ1 and the transmitted light intensity of the measurement light PL in the wavelength range λ2 is expressed by [General Formula 16].

$$I_{\lambda_1}^{out} = I_{\lambda_1}^{in} \cdot 10^{-\alpha_{\lambda_1} H} \cdot \eta_{\lambda_1}^{all} + \phi_{\lambda_1} \qquad \text{[General Formula 14]}$$

$I_{\lambda_1}^{in}$: Incident light intensity of measurement light in wavelength range λ1

$I_{\lambda_1}^{out}$: Transmitted light intensity of measurement light in wavelength range λ1

$\alpha_{\lambda_1}$: Optical absorption coefficient of water corresponding to measurement light in wavelength range λ1

$\eta_{\lambda_1}^{all}$: Loss caused by refraction of measurement light in wavelength range λ1

$\phi_{\lambda_1}$: Intensity of stray light $$I_{\lambda_2}^{out} = I_{\lambda_2}^{in} \cdot 10^{-\alpha_{\lambda_2} H} \cdot \eta_{\lambda_2}^{all} + \phi_{\lambda_2} \qquad \text{[General Formula 15]}$$

$I_{\lambda_2}^{in}$: Incident light intensity of measurement light in wavelength range λ2

$I_{\lambda_2}^{out}$: Transmitted light intensity of measurement light in wavelength range λ2

$\alpha_{\lambda_2}$: Optical absorption coefficient of water corresponding to measurement light in wavelength range λ2

$\eta_{\lambda_2}^{all}$: Loss caused by refraction of measurement light in wavelength range λ2

$\phi_{\lambda_2}$: Intensity of stray light $$\nabla I_{\lambda_1 \lambda_2}^{out} = I_{\lambda_1}^{out} - I_{\lambda_2}^{out} \qquad \text{[General Formula 16]}$$
$$= \left(I_{\lambda_1}^{in} \cdot 10^{-\alpha_{\lambda_1} H} \cdot \eta_{\lambda_1}^{all} + \phi_{\lambda_1}\right) -$$
$$\left(I_{\lambda_2}^{in} \cdot 10^{-\alpha_{\lambda_2} H} \cdot \eta_{\lambda_2}^{all} + \phi_{\lambda_2}\right)$$

Here, as in the second embodiment, in a case where the wavelength range λ1 and the wavelength range λ2 are values close to each other and the optical absorption coefficient of the water 19 is set to be greatly different, intensity of the stray light included in the transmitted light intensity of the measurement light PL in the wavelength range λ1 and intensity of the stray light included in the transmitted light intensity of the measurement light PL in the wavelength range λ2 are similar. Further, incident light intensity of the measurement light PL in the wavelength range λ1 and incident light intensity of the measurement light PL in the wavelength range λ2 are approximate. Further, a loss of the measurement light PL in the wavelength range λ1 and a loss of the measurement light PL in the wavelength range λ2 are approximate. As a result, [General Formula 16] is expressed by [General Formula 17].

$$\nabla I_{\lambda_1 \lambda_2}^{out} = I^{in} \cdot \left(10^{-\alpha_{\lambda_1} H} - 10^{-\alpha_{\lambda_2} H}\right) \cdot \eta \qquad \text{[General Formula 17]}$$
$$\phi_{\lambda_1} = \phi_{\lambda_2}$$
$$I_{\lambda_1}^{in} = I_{\lambda_2}^{in} \Rightarrow I^{in}$$
$$\eta_{\lambda_1}^{all} = \eta_{\lambda_2}^{all} \Rightarrow \eta$$

When [General Formula 17] is approximated using an approximate formula as expressed by [General Formula 18], [General Formula 17] is expressed as [General Formula 19].

$$10^{-\alpha_\lambda h} = (10^{-\alpha_\lambda h})_{h_0} + (10^{-\alpha_\lambda h})'_{h_0} \cdot (h - h_0) + \qquad \text{[General Formula 18]}$$
$$\frac{1}{2!}(10^{-\alpha_\lambda h})''_{h_0} \cdot (h - h_0)^2 + \ldots +$$
$$o(h - h_0)$$
$$= (10^{-\alpha_\lambda h_0}) + (-\alpha_\lambda 10^{-\alpha_\lambda h_0} \ln 10) \cdot$$
$$(h - h_0) + \frac{1}{2!}(\alpha_\lambda^2 10^{-\alpha_\lambda h_0} \ln^2 10) \cdot$$
$$(h - h_0)^2 + \ldots$$
$$\approx E_\lambda + F_\lambda \cdot h$$

$$\nabla I_{\lambda_1 \lambda_2}^{out} = I^{in} \cdot \left(10^{-\alpha_{\lambda_1} H} - 10^{-\alpha_{\lambda_2} H}\right) \cdot \eta = A + B \cdot H \qquad \text{[General Formula 19]}$$

"A" and "B" included in [General Formula 19] are parameters regarding refraction of the measurement light PL, and can approximate by a constant. Thus, the distance detection unit 59 of the third embodiment can accurately detect the distance H at each position of the drug surface 18a using [General Formula 19] from the transmitted light intensity of the measurement light PL in the wavelength range λ1, the transmitted light intensity of the measurement light PL in the wavelength range λ2, and the optical absorption coefficient of the water 19. Further, in the third embodiment, since the distance H is detected from a difference between the transmitted light intensity of the measurement light PL in the wavelength range λ1 and the transmitted light intensity of the measurement light PL in the wavelength range λ2 as illustrated in [General Formula 19], it is possible to cancel an influence of stray light. As a result, it is possible to more accurately detect the distance H at each position of the drug surface 18a in comparison with the first embodiment. Since a subsequent process is basically the same as in the first embodiment, description thereof will be omitted.

As described in the first embodiment, the refractive index of the aqueous drug solution 18 and the refractive index of the silicon rubber that is a material of the mold 12 are close values. Therefore, refraction angles of the measurement light PL in the wavelength range λ1 and the measurement light PL in the wavelength range λ2 refracted at a position B in FIGS. 23A and 23B decrease, and the volume (capacity) of the aqueous drug solution 18 in the needle-like recesses 14 is proportional to the distance H. Further, in a case where the distance between the imaging portion 34 and the mold 12 is long, the measurement light PL incident on the imaging portion 34 becomes parallel light. Therefore, an influence of the shape of the drug surface 18a is reduced. Further, in a case where the resolution of the imaging portion 34 is low, "A" and "B" included in [General Formula 19] can approximate to an integer. As a result, as illustrated in [General Formula 20], a sum of differences between the transmitted light intensities at the respective positions of the drug surface 18a is proportional to the volume V of the aqueous drug solution 18 in the needle-like recess 14.

$$\Sigma \nabla I_{\lambda_1 \lambda_2}^{out} \propto V \qquad \text{[General Formula 20]}$$

Fourth Embodiment

Figure 24A:
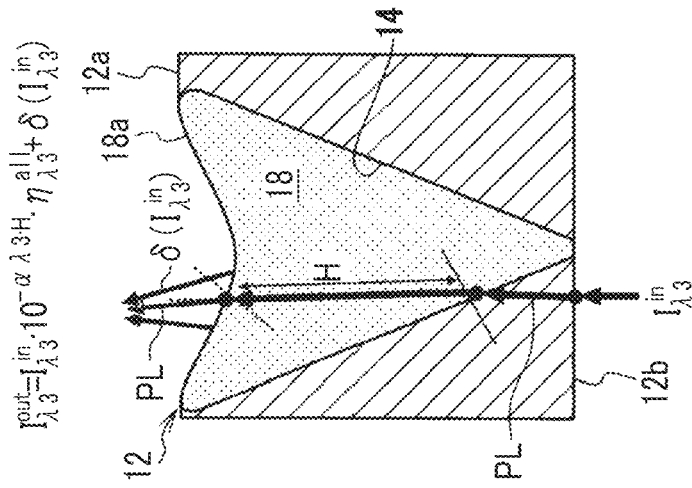
FIGS. 24A, 24B, and 24C are illustrative diagrams illustrating a process of detecting a distance H in a measurement device of a fourth embodiment.
Figure 24B:
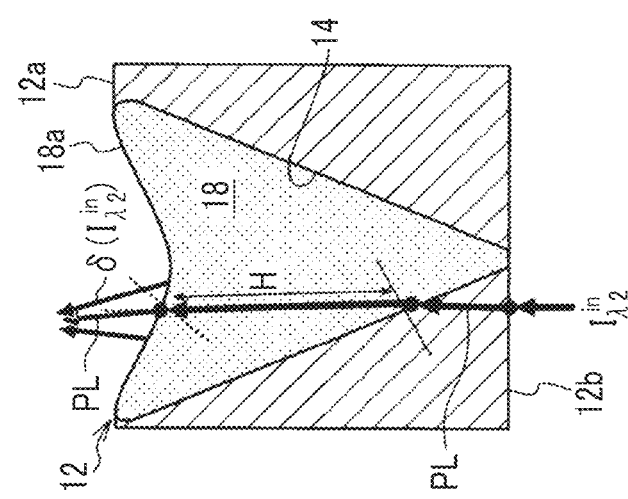
Figure 24C:
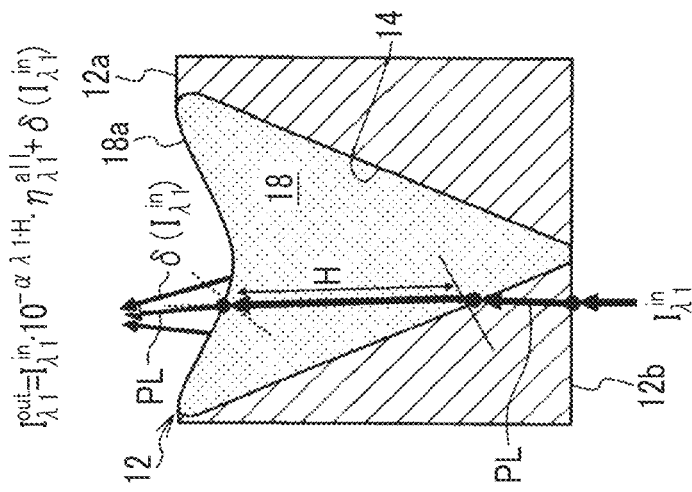

FIGS. 24A, 24B, and 24C are illustrative diagrams illustrating a process of detecting the distance H in the measurement device 10 of the fourth embodiment. In each of the above embodiments, the distance H at each position of the drug surface 18a in the needle-like recess 14 is detected using the measurement light PL in the two wavelength ranges λ1 and λ2, whereas in the fourth embodiment, the distance H at each position of the drug surface 18a in the needle-like recess 14 is detected using the measurement light PL in three wavelength ranges λ1, λ2, and λ3. Here, the measurement light PL in the wavelength range λ3 corresponds to a third measurement wave of the present invention. For example, in this embodiment, the wavelength range λ1 is 1350 nm, the wavelength range λ2 is 1450 nm, and the wavelength range λ3 is 1550 nm.

The measurement device 10 of the fourth embodiment has basically the same configuration of the measurement device 10 of each of the above embodiments except that in the imaging unit 10A (see FIGS. 1 and 18), three types of filters (interference filters; band-pass filters) corresponding to the wavelength ranges λ1, λ2, and λ3 can be alternately inserted into the imaging optical path of the measurement light PL and arranged. The same components on a function or a configuration as in each of the above embodiments are denoted with the same reference signs and description thereof will be omitted.

As illustrated in FIGS. 24A, 24B, and 24C, in the fourth embodiment, the measurement light PL in the wavelength range λ1, the measurement light PL in the wavelength range λ2, and the measurement light PL in the wavelength range λ3 transmitted through the aqueous drug solution 18 in each needle-like recess 14 are imaged by the imaging portion 34. Accordingly, first captured image data, second captured image data, and third captured image data (not illustrated) can be acquired for each needle-like recess 14. As a result, respective transmitted light intensities of the measurement light PL in the wavelength ranges λ1, λ2, and λ3 can be detected for each needle-like recess 14 by the image analysis unit 58 (see FIG. 9) described above.

The transmitted light intensity of the measurement light PL in the wavelength range λ1, the transmitted light intensity of the measurement light PL in the wavelength range λ2, and the transmitted light intensity of the measurement light PL in the wavelength range λ3 are expressed by [General Formula 21] in a case where an influence of the above-described stray light is considered. In the fourth embodiment, the intensity of the stray light is indicated by δ.

$$I_{\lambda_1}^{out} = I_{\lambda_1}^{in} \cdot 10^{-\alpha_{\lambda_1} \cdot H} \cdot \eta_{\lambda_1}^{all} + \delta(I_{\lambda_1}^{in}) \qquad \text{[General Formula 21]}$$

$$I_{\lambda_2}^{out} = I_{\lambda_2}^{in} \cdot 10^{-\alpha_{\lambda_2} \cdot H} \cdot \eta_{\lambda_2}^{all} + \delta(I_{\lambda_2}^{in})$$

$$I_{\lambda_3}^{out} = I_{\lambda_3}^{in} \cdot 10^{-\alpha_{\lambda_3} \cdot H} \cdot \eta_{\lambda_3}^{all} + \delta(I_{\lambda_3}^{in})$$

$I_{\lambda_3}^{in}$: Incident light intensity of measurement light in wavelength range λ3

$I_{\lambda_3}^{out}$: Transmitted light intensity of measurement light in wavelength range λ3

$\alpha_{\lambda_3}$: Optical absorption coefficient of water corresponding to measurement light in wavelength range λ3

$\eta_{\lambda_3}^{all}$: Loss caused by refraction of measurement light in wavelength range λ3

$$\left.\begin{array}{l}\delta(I_{\lambda_1}^{in})\\ \delta(I_{\lambda_2}^{in})\\ \delta(I_{\lambda_3}^{in})\end{array}\right\} : \text{Intensity of stray light}$$

Here, in a case where the wavelength range λ1 and the wavelength range λ2 are close values, the intensity of the stray light included in the transmitted light intensity of the measurement light PL in the wavelength range λ1 and the intensity of the stray light included in the transmitted light intensity of the measurement light PL in the wavelength range λ2 approximate. Further, a loss caused by refraction of the measurement light PL in the wavelength range λ1 and a loss caused by refraction of the measurement light PL in the wavelength range λ2 approximate. Accordingly, if a difference between the transmitted light intensity of the measurement light PL in the wavelength range λ1 and the transmitted light intensity of the measurement light PL in the wavelength range λ2 is obtained, the difference is expressed by [General Formula 22].

$$I_{\lambda_1}^{out} - I_{\lambda_2}^{out} = I_{\lambda_1}^{in} \cdot 10^{-\alpha_{\lambda_1} \cdot H} \cdot \eta_{\lambda_1}^{all} - I_{\lambda_2}^{in} \cdot \qquad \text{[General Formula 22]}$$

$$10^{-\alpha_{\lambda_2} \cdot H} \cdot \eta_{\lambda_2}^{all}$$

$$= (I_{\lambda_1}^{in} \cdot 10^{-\alpha_{\lambda_1} \cdot H} - I_{\lambda_2}^{in} \cdot 10^{-\alpha_{\lambda_2} \cdot H})$$

$$\cdot \eta_{\lambda_{12}}^{all}$$

$$\left(\begin{array}{l}\delta(I_{\lambda_1}^{in}) \approx \delta(I_{\lambda_3}^{in})\\ \eta_{\lambda_1}^{all} \approx \eta_{\lambda_2}^{all} \to \eta_{\lambda_{12}}^{all}\end{array}\right)$$

Further, in a case where the wavelength range λ2 and the wavelength range λ3 are close values, the intensity of the stray light included in the transmitted light intensity of the measurement light PL in the wavelength range λ2 and the intensity of the stray light included in the transmitted light intensity of the measurement light PL in the wavelength range λ3 are approximate. Further, a loss caused by refraction of the measurement light PL in the wavelength range λ2 and a loss caused by refraction of the measurement light PL in the wavelength range λ3 approximate. Accordingly, if a difference between the transmitted light intensity of the measurement light PL in the wavelength range λ3 and the transmitted light intensity of the measurement light PL in the wavelength range λ2 is obtained, the difference is expressed by [General Formula 23].

$$I_{\lambda_3}^{out} - I_{\lambda_2}^{out} = \left(I_{\lambda_3}^{in} \cdot 10^{-\alpha_{\lambda_3} \cdot H} - I_{\lambda_2}^{in} \cdot 10^{-\alpha_{\lambda_2} \cdot H}\right) \cdot \eta_{32}^{all} \quad \text{[General Formula 23]}$$

$$\left(\begin{array}{c} \delta(I_{\lambda_3}^{in}) \approx \delta(I_{\lambda_2}^{in}) \\ \eta_{\lambda_3}^{all} \approx \eta_{\lambda_2}^{all} \rightarrow \eta_{\lambda_{32}}^{all} \end{array}\right)$$

When a difference expressed by [General Formula 22] is divided by a difference expressed by [General Formula 23], the difference is expressed by [General Formula 24]. Since the difference is obtained in each of [General Formula 23] and [General Formula 24], it is possible to cancel effects of the stray light.

$$\frac{I_{\lambda_1}^{out} - I_{\lambda_2}^{out}}{I_{\lambda_3}^{out} - I_{\lambda_2}^{out}} = \frac{I_{\lambda_1}^{in} \cdot 10^{-\alpha_{\lambda_1} \cdot H} - I_{\lambda_2}^{in} \cdot 10^{-\alpha_{\lambda_2} \cdot H}}{I_{\lambda_3}^{in} \cdot 10^{-\alpha_{\lambda_3} \cdot H} - I_{\lambda_2}^{in} \cdot 10^{-\alpha_{\lambda_2} \cdot H}} \quad \text{[General Formula 24]}$$

Since the distance H is expressed by an index in [General Formula 24], it is difficult for the distance detection unit 59 of the fourth embodiment to obtain the distance H using [General Formula 24]. Therefore, the distance detection unit 59 of the fourth embodiment applies, for example, the distance H from 0 to $H_{MAX}$ with an increment of 0.01 to ΔD expressed by [General Formula 25] obtained by modifying [General Formula 24] to obtain the distance H in which ΔD is minimized. That is, the distance detection unit 59 of the fourth embodiment detects the distance H at each position of the drug surface 18a using [General Formula 26].

$$\Delta D = \left| \left(I_{\lambda_1}^{out} - I_{\lambda_2}^{out}\right) \cdot \left(I_{\lambda_3}^{in} \cdot 10^{-\alpha_{\lambda_3} \cdot H} - I_{\lambda_2}^{in} \cdot 10^{-\alpha_{\lambda_2} \cdot H}\right) - \right. \quad \text{[General Formula 25]}$$
$$\left. \left(I_{\lambda_3}^{out} - I_{\lambda_2}^{out}\right) \cdot \left(I_{\lambda_1}^{in} \cdot 10^{-\alpha_{\lambda_1} \cdot H} - I_{\lambda_2}^{in} \cdot 10^{-\alpha_{\lambda_2} \cdot H}\right) \right|$$

$$H = \operatorname*{argmin}_{H=0 \sim H_{max}} \left\{ \Delta D = \left| \left(I_{\lambda_1}^{out} - I_{\lambda_2}^{out}\right) \cdot \right. \right. \quad \text{[General Formula 26]}$$
$$\left(I_{\lambda_3}^{in} \cdot 10^{-\alpha_{\lambda_3} \cdot H} - I_{\lambda_2}^{in} \cdot 10^{-\alpha_{\lambda_2} \cdot H}\right) -$$
$$\left(I_{\lambda_3}^{out} - I_{\lambda_2}^{out}\right) \cdot$$
$$\left. \left. \left(I_{\lambda_1}^{in} \cdot 10^{-\alpha_{\lambda_1} \cdot H} - I_{\lambda_2}^{in} \cdot 10^{-\alpha_{\lambda_2} \cdot H}\right) \right| \right\}$$

Figure 25A:
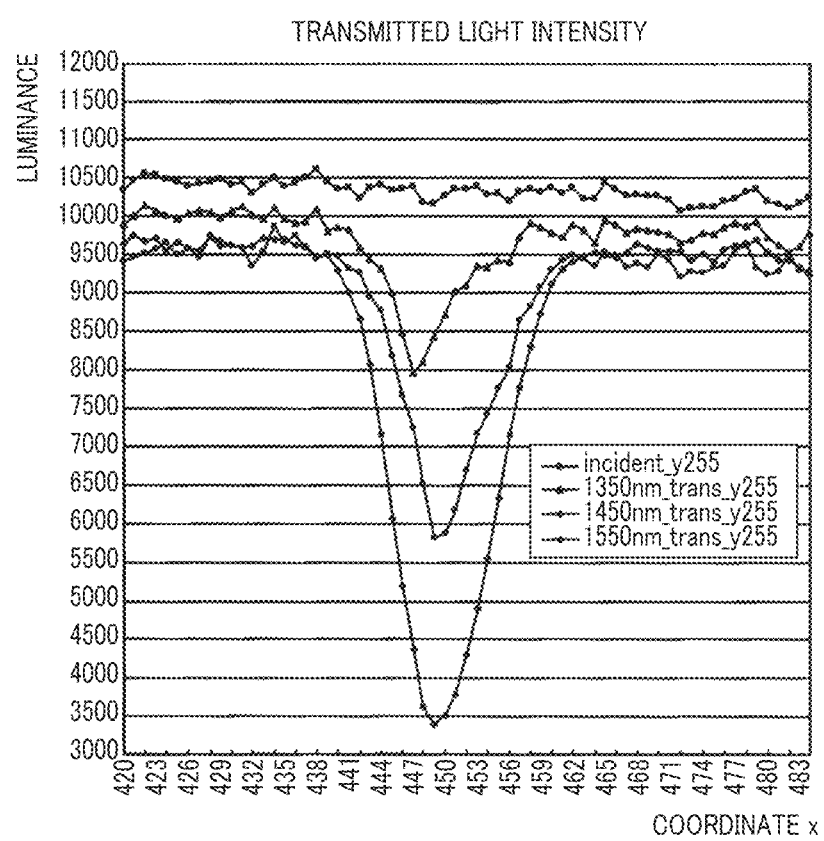
FIGS. 25A and 25B are illustrative diagrams specifically illustrating detection of a distance H in a distance detection unit of the fourth embodiment.
Figure 25B:
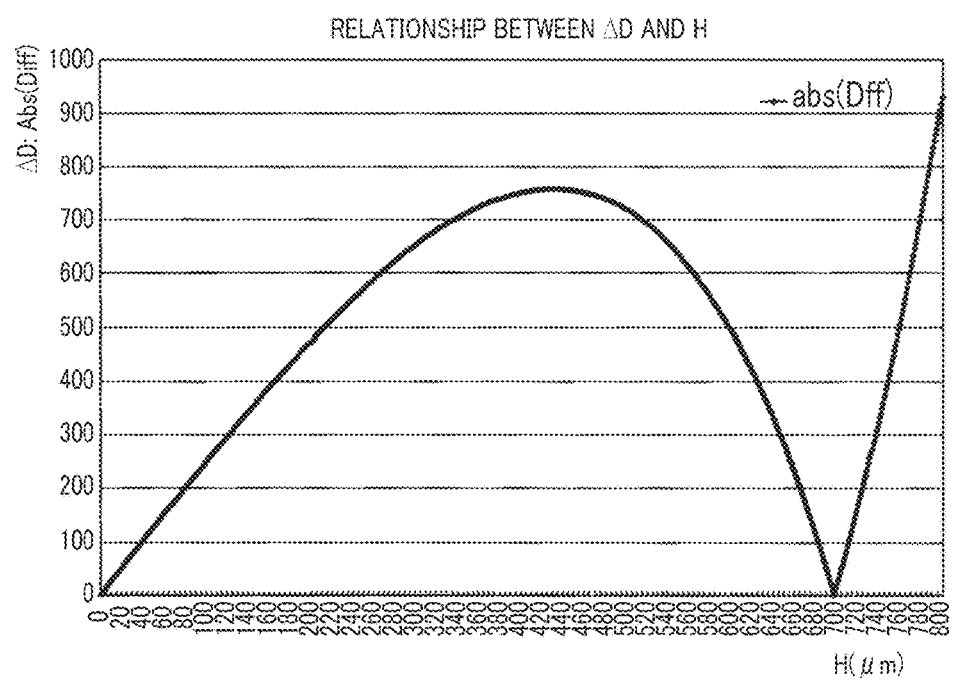

FIGS. 25A and 25B are illustrative diagrams specifically illustrating detection of the distance H in the distance detection unit 59 of the fourth embodiment. As illustrated in FIG. 25A, the distance detection unit 59 of the fourth embodiment acquires the transmitted light intensity of the measurement light PL in the wavelength ranges λ1, λ2, and λ3 from the image analysis unit 58, for each needle-like recess 14. "incident_y255" in FIGS. 25A and 25B indicates an example of the incident light intensity of the measurement light PL, and "1350 nm_trans_y255", "1450 nm_trans_y255", and "1550 nm_trans_y255" indicate examples of the transmitted light intensity of the measurement light PL in the wavelength ranges λ1, λ2, and λ3.

Then, the distance detection unit 59 of the fourth embodiment applies the acquisition result of each transmitted light intensity and a known optical absorption coefficient for each wavelength range to [General Formula 26], and then, applies, for example, the distance H from 0 to $H_{MAX}$ with an increment of 0.01 to ΔD to obtain the distance H at which ΔD is minimized, as illustrated in FIG. 25B. For example, in FIG. 25B, since ΔD is minimized in a case where the distance H is 698 nm, the distance detection unit 59 of the fourth embodiment sets the distance H to 698 nm. Hereinafter, similarly, the distance detection unit 59 of the fourth embodiment detects the distance H at each position of the drug surface 18a. Since subsequent processes are basically the same as in the first embodiment, description thereof will be omitted herein.

Thus, in the fourth embodiment, since the distance H at each position of the drug surface 18a in the needle-like recesses 14 is detected using [General Formula 26] after the transmission light intensities of the measurement light PL in three wavelength ranges λ1, λ2, and λ3 are acquired, an influence of the stray light can be canceled. As a result, it is possible to more accurately detect the distance H at each position of the drug surface 18a in comparison with the first embodiment.

Although the case where the distance H at each position of the drug surface 18a in the needle-like recess 14 is detected using the measurement light PL in three wavelength ranges λ1, λ2, and λ3 has been described in the fourth embodiment, the distance H at each position of the drug surface 18a may be detected using the measurement light PL in four or more wavelength ranges that are different from one another (may partially overlap one another).

Fifth Embodiment

Figure 26:
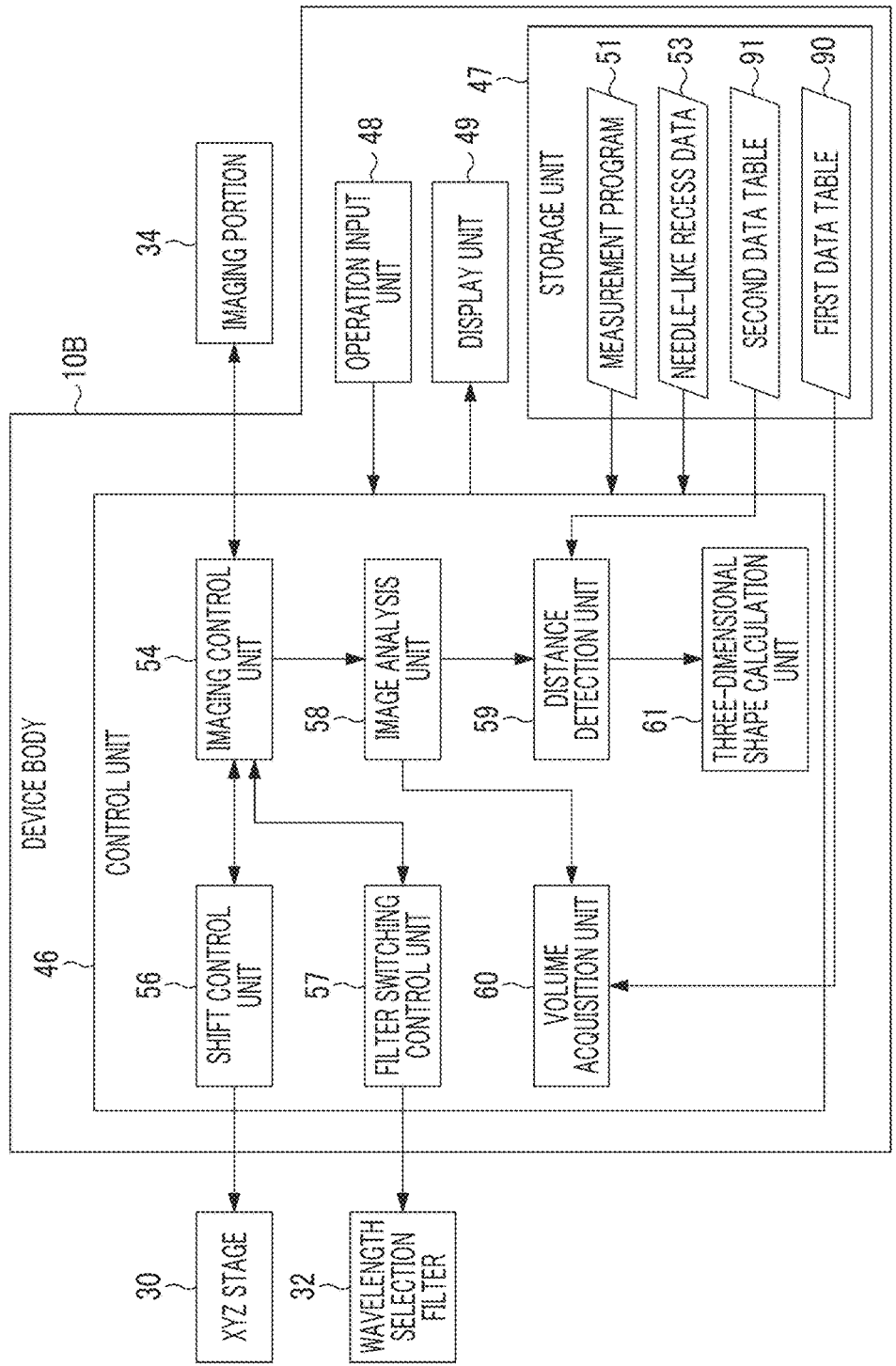
FIG. 26 is a block diagram illustrating a configuration of a device body of a measurement device of a fifth embodiment.

FIG. 26 is a block diagram illustrating a configuration of the device body 10B of the measurement device 10 of a fifth embodiment. In the first embodiment, the distance H at each position of the drug surface 18a in the needle-like recess 14 is detected for each needle-like recess 14 using [General Formula 5] on the basis of the detection result of the transmitted light intensities $I_{\lambda,1}$ and $I_{\lambda,2}$ of each needle-like recess 14, and the volume of the aqueous drug solution 18 in each needle-like recess 14 is calculated from the detection result or the like. On the other hand, in the fifth embodiment, the volume for each needle-like recess 14 of the aqueous drug solution 18 can be directly acquired without performing a calculation process using a formula on the basis of the detection result of the transmitted light intensities $I_{\lambda,1}$ and $I_{\lambda,2}$ of each needle-like recess 14. Since the measurement device of the fifth embodiment has basically the same configuration of the measurement device 10 of the first embodiment, components having the same function or configuration as in the first embodiment are denoted with the same reference signs and description thereof will be omitted.

As illustrated in FIG. 26, the image analysis unit 58 of the fifth embodiment outputs a detection result of the transmitted light intensities $I_{\lambda,1}$ and $I_{\lambda,2}$ of each needle-like recess 14 to the distance detection unit 59 and the volume acquisition unit 60. Further, the first data table 90 and the second data table 91 are stored in the storage unit 47 of the fifth embodiment in advance. The first data table 90 corresponds to a correspondence relationship of the present invention, and is used to acquire the volume of the aqueous drug solution 18 of each needle-like recess 14 in the volume acquisition unit 60 of the fifth embodiment. Further, the second data table 91 is used to detect the distance H at each position of the drug surface 18a of each needle-like recess 14 in the distance detection unit 59 of the fifth embodiment.

FIG. 27A is an illustrative diagram illustrating an example of the first data table 90, and FIG. 27B is an illustrative diagram illustrating an example of the second data table 91.

As illustrated in FIG. 27A, the first data table 90 is generated by obtaining a correspondence relationship between each of the transmitted light intensities $I_{\lambda 1}$ and $I_{\lambda 2}$ and the volume of the aqueous drug solution 18 in the needle-like recess 14 through an experiment, a simulation, or the like in advance.

For example, the first data table 90 indicates a correspondence relationship between a sum or a representative value of the transmitted light intensities $I_{\lambda 1}$ at respective positions of the drug surface 18a and the volume of the aqueous drug solution 18, and a correspondence relationship between a sum or a representative value of the transmitted light intensities $I_{\lambda 2}$ at respective positions and the volume of the aqueous drug solution 18. The representative value is the transmitted light intensities $I_{\lambda 1}$ and $I_{\lambda 2}$ at an arbitrary point (for example, a center) among respective positions of the drug surface 18a or average transmitted light intensities $I_{\lambda 1}$ and $I_{\lambda 2}$ at a plurality of arbitrary points among the respective positions.

As illustrated in FIG. 27B, the second data table 91 is generated by obtaining a correspondence relationship between each of the transmitted light intensities $I_{\lambda 1}$ and $I_{\lambda 2}$ and the distance H through an experiment, a simulation, or the like in advance. The second data table 91 may be generated for each incidence position according to a position of incidence of the measurement light PL on the needle-like recess 14 (for example, the communication hole 31 or the wall surface of the needle-like recesses 14).

Referring back to FIG. 26, the volume acquisition unit 60 of the fifth embodiment acquires the volume of the aqueous drug solution 18 in each needle-like recess 14 by referring to the first data table 90 acquired from the storage unit 47 on the basis of the detection result of the transmitted light intensities $I_{\lambda 1}$ and $I_{\lambda 2}$ of each needle-like recess 14 input from the image analysis unit 58. For example, an average of the volume of the aqueous drug solution 18 obtained from the detection result of the transmitted light intensity $I_{\lambda 1}$ and the volume of the aqueous drug solution 18 obtained from the detection result of the transmitted light intensity $I_{\lambda 2}$ or a predetermined one of the volumes may be acquired as the volume of the aqueous drug solution 18 of each needle-like recess 14.

Further, the volume acquisition unit 60 of the fifth embodiment calculates a total volume of the entire aqueous drug solution 18 in the mold 12 from the volumes of the aqueous drug solutions 18 of the respective needle-like recesses 14, similar to the first embodiment.

The distance detection unit 59 of the fifth embodiment detects the distance H at each position of the drug surface 18a of each needle-like recess 14 by referring to the second data table 91 acquired from the storage unit 47 on the basis of the detection result of the transmitted light intensities $I_{\lambda 1}$ and $I_{\lambda 2}$ of each needle-like recess 14 input from the image analysis unit 58, and outputs the detection result to the three-dimensional shape calculation unit 61. For example, an average or a predetermined one of the distance H obtained from the detection result of the transmitted light intensity $I_{\lambda 1}$ and the distance H obtained from the detection result of the transmitted light intensity $I_{\lambda 2}$ is determined as a distance H at each position of the drug surface 18a of each needle-like recess 14.

The first data table 90 and the second data table 91 may be stored in a storage unit separate from the device body 10B, such as a server or a database on the Internet, instead of being stored in the storage unit 47, and the first data table 90 and the second data table 91 may be acquired from the storage unit.

Figure 28:
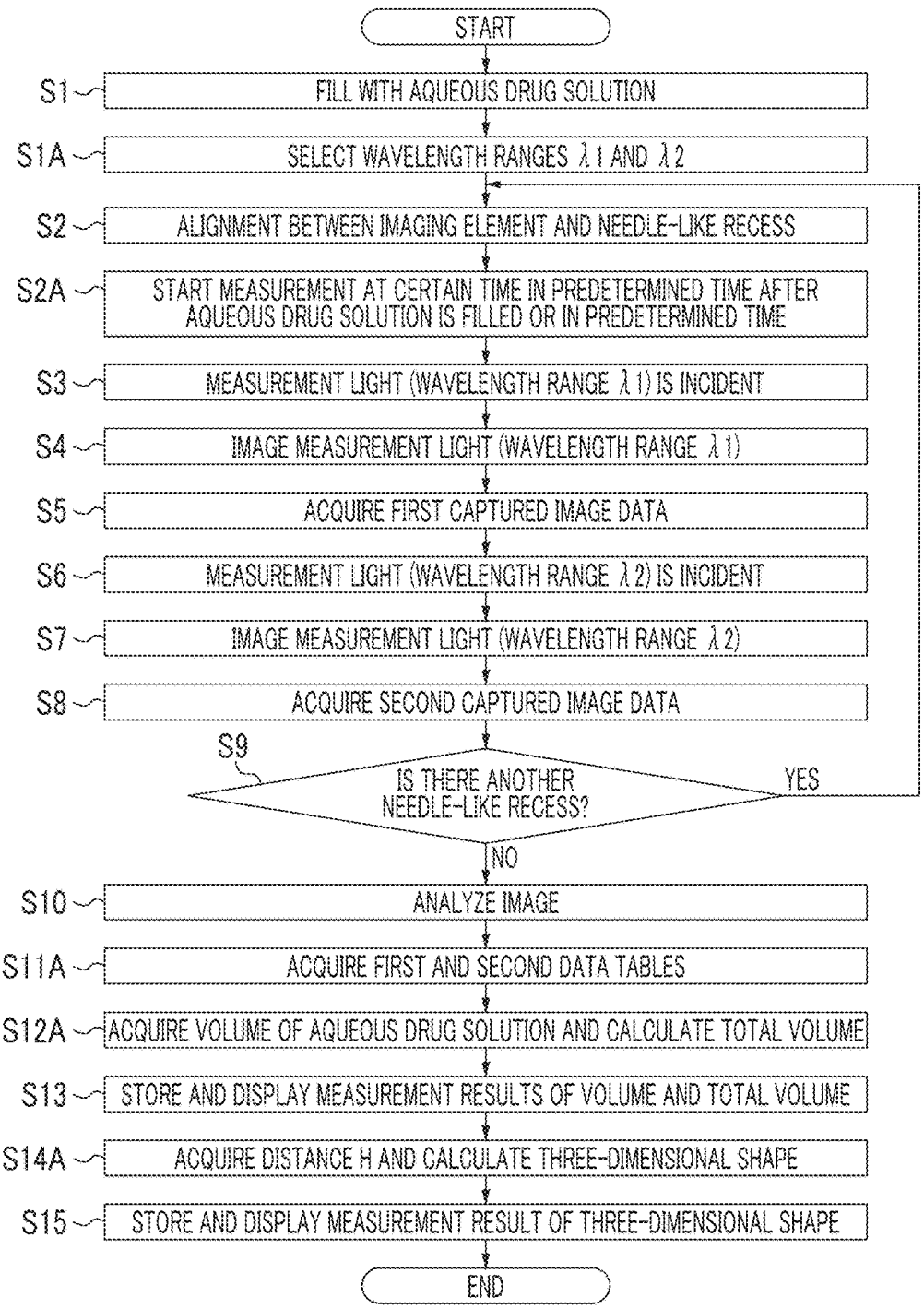
FIG. 28 is a flowchart illustrating a flow of a process of measuring a volume of an aqueous drug solution for each needle-like recess in the fifth embodiment.

Next, an operation of the measurement device 10 of the fifth embodiment having the above configuration will be described with reference to FIG. 28. FIG. 28 is a flowchart illustrating a flow of a process of measuring a volume of the aqueous drug solution 18 in each needle-like recess 14 in the fifth embodiment. The process from step S1 to step S10 is basically the same as the process of the first embodiment illustrated in FIG. 17 described above, specific description thereof is omitted.

Through the process of step S10, the detection result of the transmitted light intensities $I_{\lambda 1}$ and $I_{\lambda 2}$ of each needle-like recess 14 is output from the image analysis unit 58 to the distance detection unit 59 and the volume acquisition unit 60. After this output, the volume acquisition unit 60 acquires the first data table 90 from the storage unit 47, and the distance detection unit 59 acquires the second data table 91 from the storage unit 47 (step S11A).

Then, the volume acquisition unit 60 acquires the volume of the aqueous drug solution 18 in each needle-like recess 14 by referring to the first data table 90 on the basis of the detection result of the transmitted light intensities $I_{\lambda 1}$ and $I_{\lambda 2}$ of each needle-like recess 14 input from the image analysis unit 58, and calculates the total volume of the entire aqueous drug solution 18 in the mold 12 (step S12A, which corresponds to a volume acquisition step of the present invention). The volume acquisition unit 60 outputs the acquisition result of the volume of the aqueous drug solution 18 and the calculation result of the total volume as the measurement result of the volume and the total volume of the aqueous drug solution 18 to the storage unit 47 and the display unit 49. Thus, the measurement results of the volume and the total volume of the aqueous drug solution 18 are stored in the storage unit 47 and are displayed on the display unit 49 (step S13).

The distance detection unit 59 detects the distance H at each position of the drug surface 18a of each needle-like recess 14 by referring to the second data table 91 acquired from the storage unit 47 on the basis of the detection result of the transmitted light intensities $I_{\lambda 1}$ and $I_{\lambda 2}$ of each needle-like recess 14 input from the image analysis unit 58, and outputs the detection result to the three-dimensional shape calculation unit 61. Thus, as in the first embodiment, the three-dimensional shape of the drug surface 18a within each needle-like recess 14 is calculated in the three-dimensional shape calculation unit 61 (step S14A, which corresponds to the shape detection step of the present invention). Since a subsequent process is the same as the first embodiment, description thereof is omitted.

Thus, in the measurement device 10 of the fifth embodiment, since the volume or the distance H for each needle-like recess 14 is directly obtained from the detection result of the transmitted light intensities $I_{\lambda 1}$ and $I_{\lambda 2}$ of each needle-like recess 14 on the basis of the first data table 90 and the second data table 91 that have been acquired in advance, it is possible to reduce a calculation process in comparison with the first embodiment, in addition to the same effects as in the first embodiment being obtained.

In a case where the distance H is detected using the measurement light PL in the three wavelength ranges $\lambda 1$, $\lambda 2$, and $\lambda 3$ as in the fourth embodiment, the volume or the distance H for each needle-like recess 14 may be directly obtained by referring to the first table and the second data table (not illustrated) that have been acquired in advance, as in the fifth embodiment. In this case, the second data table indicating a correspondence relationship between the transmitted light intensity and the distance H of the measurement light PL in the three wavelength ranges may be generated using [General Formula 26] or the like. Further, the data table has been described by way of example of a correspondence relationship of the present invention, but a form thereof is not particularly limited as long as the data table shows the correspondence relationship.

Sixth Embodiment

Figure 29:
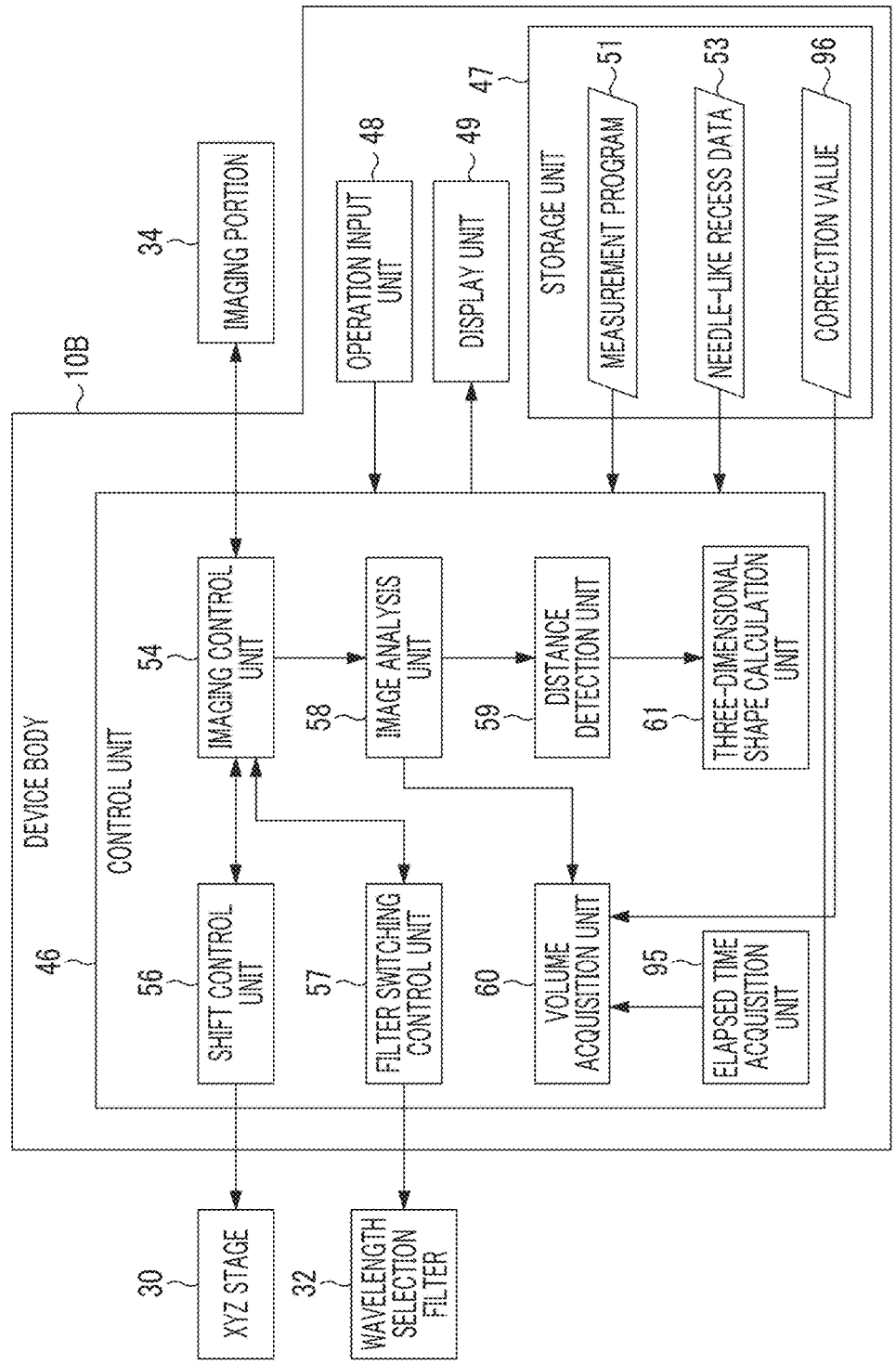
FIG. 29 is a block diagram illustrating a configuration of a measurement device according to a sixth embodiment.

FIG. 29 is a block diagram illustrating a configuration of the measurement device 10 of a sixth embodiment. In each of the above embodiments, the volume of the aqueous drug solution 18 in each needle-like recess 14 is measured, but since the water 19 contained in the aqueous drug solution 18 in each needle-like recess 14 evaporates over time as described above, the volume of the aqueous drug solution 18 in each needle-like recess 14 is reduced over time from the time of filling (see FIG. 3). Therefore, in the measurement device 10 of the sixth embodiment, the amount of filling of the aqueous drug solution 18 filled in the needle-like recess 14 (volume immediately after filling of the aqueous drug solution 18) is calculated. The measurement device 10 of the sixth embodiment has basically the same configuration of the measurement device 10 of each of the above embodiments except that the amount of filling of the aqueous drug solution 18 filled in the needle-like recess 14 is measured. The same components on a function or a configuration as in each of the above embodiments are denoted with the same reference signs and description thereof will be omitted.

As illustrated in FIG. 29, the elapsed time acquisition unit 95 is provided in the device body 10B of the sixth embodiment, and the correction value 96 is stored in the storage unit 47.

The elapsed time acquisition unit 95 acquires the elapsed time until step S3 [an incidence step (measurement wave intensity acquisition step) of the present invention] illustrated in FIG. 17 described above after the aqueous drug solution 18 is filled in each needle-like recess 14. For example, the elapsed time acquisition unit 95 compares the filling time of the aqueous drug solution 18 into each needle-like recess 14 input in advance with the start time of step S3 described above to acquire the elapsed time described above. Then, the elapsed time acquisition unit 95 outputs the acquired elapsed time to the volume acquisition unit 60.

The correction value 96 is a correction value for correcting the decrease over time the volume of the aqueous drug solution 18 filled in the needle-like recess 14 and is obtained, for example, from a graph indicating a temporal change of the volume of the aqueous drug solution 18 in the needle-like recess 14 as illustrated in FIG. 21 described above.

Specifically, since the amount of decrease in the aqueous drug solution 18 in each elapsed time can be discriminated from the graph illustrated in FIG. 21 or the like, a reduced amount of the aqueous drug solution 18 in each elapsed time can be used as the correction value 96. Since a proportional relationship is established between the volume of the aqueous drug solution 18 in the needle-like recesses 14 and the above-described distance H (see FIGS. 11A to 11C), "correcting a decrease over time in the distance H" is included in the above-described "correcting the decrease over time of the volume of the aqueous drug solution 18". Accordingly, a correction value for indirectly correcting the volume of the aqueous drug solution 18 in the needle-like recess 14 by correcting the distance H at each position of the drug surface 18a in the needle-like recess 14 using the distance H at the time of filling is included in the correction value 96, in addition to the correction value for directly correcting the volume of the aqueous drug solution 18 in the needle-like recess 14.

The volume acquisition unit 60 of the measurement device 10 of the sixth embodiment acquires the amount of filling of the drug 16 filled in each needle-like recess 14 on the basis of the elapsed time input from the elapsed time acquisition unit 95 and the correction value 96 read from the storage unit 47, in addition to acquisition of the volume of the aqueous drug solution 18 in each needle-like recess 14 as in the first embodiment.

Figure 30:
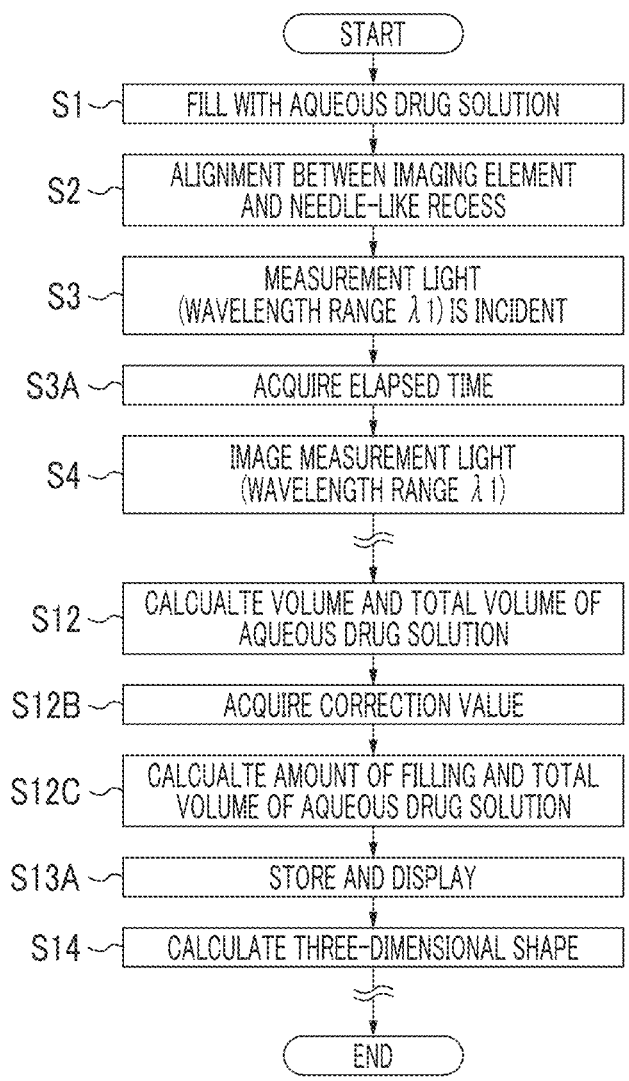
FIG. 30 is a flowchart illustrating a flow of a process of measuring a filling amount of an aqueous drug solution filled in each needle-like recess in the measurement device of the sixth embodiment.

FIG. 30 is a flowchart illustrating a flow of a process of measuring the amount of filling of the aqueous drug solution 18 filled in the needle-like recess 14 in the measurement device 10 of the sixth embodiment. As illustrated in FIG. 30, a flow of the process up to step S12 is basically the same as in the first embodiment illustrated in FIG. 17 described above. However, in the sixth embodiment, after the process in step S3, the elapsed time acquisition unit 95 acquires the elapsed time described above and outputs the elapsed time to the volume acquisition unit 60 (step S3A, which corresponds to an elapsed time acquisition step of the present invention).

The volume acquisition unit 60 of the sixth embodiment obtains the volume or the like of the aqueous drug solution 18 of each needle-like recess 14 as in the first embodiment in step S12, and then, acquires the correction value 96 from the storage unit 47 (step S12B, which corresponds to a correction value acquisition step of the present invention). As a method of acquiring the volume or the like of the aqueous drug solution 18 in each needle-like recess 14, a method described in the fifth embodiment described above may be executed.

Next, the volume acquisition unit 60 corrects the volume of the aqueous drug solution 18 in each needle-like recess 14 with the correction value 96 corresponding to the elapsed time on the basis of the elapsed time acquired by the elapsed time acquisition unit 95. For example, a decrease amount (the correction value 96) of the aqueous drug solution 18 according to the elapsed time is added to the volume of the aqueous drug solution 18 in each needle-like recess 14. Thus, the amount of filling of the aqueous drug solution 18 filled in each needle-like recess 14 is calculated, and a total volume of the amount of filling of the entire aqueous drug solution 18 in the mold 12 is calculated from the amount of filling of the aqueous drug solution 18 for each needle-like recess 14 (step S12C). Thus, the volume acquisition unit 60 can acquire the amount of filling of the aqueous drug solution 18 into the needle-like recess 14 and a total volume thereof.

In a case where the correction value 96 is a correction value of the distance H descried above, the volume acquisition unit 60 corrects the result of the detection of the distance H of each needle-like recess 14 input from the distance detection unit 59 using the correction value 96, and acquires the distance H after filling of the aqueous drug solution 18 into each needle-like recess 14 on the basis of the distance H after correction. Accordingly, it is possible to indirectly correct the volume of the aqueous drug solution 18 in each needle-like recess 14. The volume acquisition unit 60 calculates the amount of filling of the aqueous drug solution 18 filled in the needle-like recesses 14 on the basis of the distance H at each position of the drug surface 18a of each needle-like recess 14, and the needle-like recess data 53 read from the storage unit 47.

The volume acquisition unit 60 outputs the calculation result of the volume and the amount of filling of the aqueous drug solution 18 in each needle-like recess 14, and the calculation result of the total volume of each of the volume and the amount of filling of the aqueous drug solution 18 to the storage unit 47 and the display unit 49. Thus, the calculation result of the volume and the amount of filling of the aqueous drug solution 18 in each needle-like recess 14 is stored in the storage unit 47 as a measurement result of the volume and the amount of filling of the aqueous drug solution 18 in each needle-like recess 14, and is displayed on the display unit 49 (step S13A, which corresponds to an acquisition result processing step of the present invention). Further, the calculation result of the total volume of each of the volume and the amount of filling of the aqueous drug solution 18 is stored in the storage unit 47 as a measurement result of the total volume of each of the volume and the amount of filling of the aqueous drug solution 18 and is displayed on the display unit 49.

Further, on the display unit 49, an allowable criterion of the volume of the drug 16, an allowable criterion of the amount of filling, and an allowable criterion of a total volume of each of the volume and the amount of filling are displayed, and a determination result obtained by determining whether or not each satisfies the allowable criterion is displayed. Since subsequent processes are basically the same as in the first embodiment, description thereof will be omitted.

Although the volume acquisition unit 60 corrects the volume of the aqueous drug solution 18 in each needle-like recess 14 using the correction value 96 in this embodiment, the volume of the aqueous drug solution 18 in each needle-like recess 14 may be corrected using a method in which the correction value 96 is not used, such as addition of a volume determined for each elapsed time in advance to the volume of the aqueous drug solution 18 in each needle-like recess 14.

[Effects of Sixth Embodiment]

Thus, in the sixth embodiment, since the amount of filling of the aqueous drug solution 18 filled in each needle-like recess 14 can be measured, a result of the measurement can be fed back to a filling device (not illustrated) that fills the aqueous drug solution 18 into each needle-like recess 14 of the mold 12. As a result, it is possible to appropriately adjust the amount of filling of the aqueous drug solution 18 into each needle-like recess 14 in the filling device.

Seventh Embodiment

Next, a measurement device 10 of the seventh embodiment of the present invention will be described. In the first embodiment, the volume of the aqueous drug solution 18 in each needle-like recess 14 is measured on the basis of the transmitted light intensities $I_{\lambda 1}$ and $I_{\lambda 2}$ of the two types of measurement light PL in different wavelength ranges transmitted through the aqueous drug solution 18 in each needle-like recess 14.

Figure 31:
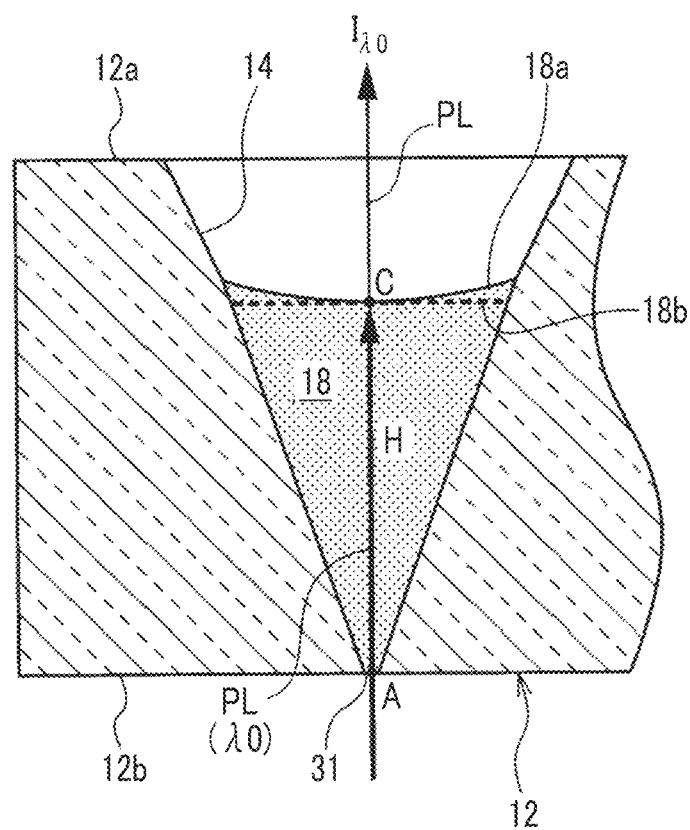
FIG. 31 is an illustrative diagram illustrating a process of measuring a volume of an aqueous drug solution in a needle-like recess in a measurement device of a seventh embodiment.

On the other hand, as illustrated in FIG. 31, in the measurement device 10 of the seventh embodiment, the volume of the aqueous drug solution 18 in each needle-like recess 14 is measured using the measurement light PL in one type of wavelength range $\lambda 0$. Here, FIG. 31 is an illustrative diagram illustrating a process of measuring the volume of the aqueous drug solution 18 in the needle-like recess 14 in the measurement device 10 of the seventh embodiment.

In the measurement device 10 of the seventh embodiment, in order to avoid an influence of refraction or the like at an interface between an inner surface of the needle-like recess 14 and the aqueous drug solution 18, the measurement light PL in the wavelength range $\lambda 0$ is incident on the aqueous drug solution 18 in the needle-like recess 14 from the communication hole 31, and the transmitted light intensity $I_{\lambda 0}$ (corresponding to the intensity of the measurement wave of the present invention) of the measurement light PL in the wavelength range $\lambda 0$ transmitted through the aqueous drug solution 18 is detected. The wavelength range $\lambda 0$ is not particularly limited as long as the wavelength range $\lambda 0$ is a wavelength range in which optical absorption by the water 19 occurs (see FIGS. 5 and 6), and an appropriate wavelength range may be determined according to a thickness of the mold 12 or the amount of filling of the aqueous drug solution 18, as described in the first embodiment.

Then, in the measurement device 10 of the seventh embodiment, the distance H from the communication hole 31 to the drug surface 18a, that is, the distance H between the position A passing through the center of the needle-like recess 14 and the position C of the drug surface 18a is detected using [General Formula 1] on the basis of the detection result of the transmitted light intensity $I_{\lambda 0}$ of each needle-like recess 14. In the measurement device 10 of the seventh embodiment, the distance H at the position C is regarded as a height of a liquid surface of the entire drug surface 18a (a distance from the second surface 12b to the virtual drug surface 18b), and the volume of the aqueous drug solution 18 in each needle-like recess 14 is calculated on the basis of the distance H (liquid surface height) and the needle-like recess data 53.

As illustrated in FIG. 20B described above, the drug surface 18a can be caused to have a planar shape by performing hydrophilic treatment on the first surface 12a of the mold 12, and an error between the actual drug surface 18a and the virtual drug surface 18b is reduced. As a result, it is possible to improve the measurement accuracy.

Figure 32:
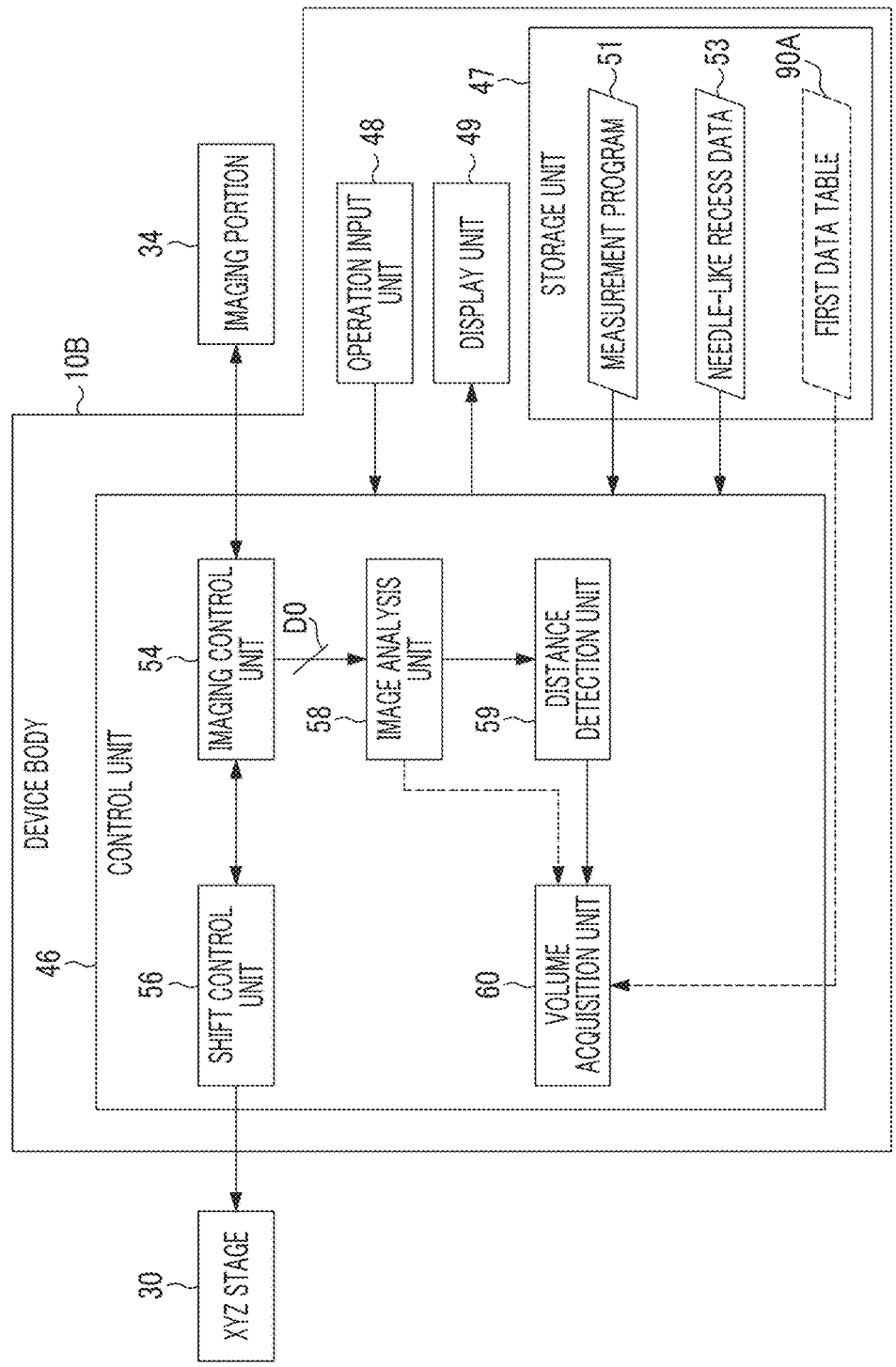
FIG. 32 is a block diagram illustrating a configuration of a measurement device of the seventh embodiment.

FIG. 32 is a block diagram illustrating a configuration of the measurement device 10 of the seventh embodiment. Further, FIG. 33 is a flowchart illustrating a flow of a process of measuring the volume of the aqueous drug solution 18 in each needle-like recess 14 in the measurement device 10 of the seventh embodiment. The measurement device 10 of the seventh embodiment has basically the same configuration of the measurement device 10 of each of the above embodiments except that the measurement is performed using one type of measurement light PL in the wavelength range $\lambda 0$. The same components on a function or a configuration as in each of the above embodiments are denoted with the same reference signs and description thereof will be omitted.

As illustrated in FIGS. 32 and 33, in the seventh embodiment, after the aqueous drug solution 18 is filled in each needle-like recess 14 (step S1), registration of a center of the imaging element of the imaging portion 34 and a center (communication hole 31) of the needle-like recesses 14 that is a measurement target is performed (step S2D).

Next, similar to the first embodiment (step S2A of FIG. 17), the measurement light PL in the wavelength range $\lambda 0$ is incident on the communication hole 31 of the second surface 12b from the light source 27 through an interference filter (not illustrated) or the like in a predetermined time after the aqueous drug solution 18 is filled (for example, in 5 minutes) or in a certain time in a predetermined time (step S3D). The measurement light PL in the wavelength range $\lambda 0$ is transmitted through the aqueous drug solution 18 of the needle-like recess 14 that is a measurement target through the communication hole 31. Thus, the measurement light PL in the wavelength range $\lambda 0$ is emitted from the drug surface 18a of the aqueous drug solution 18, and the measurement light PL in this wavelength range λ0 is incident on the imaging portion 34 through the imaging optical system 33.

The imaging portion 34 performs imaging of the measurement light PL in the wavelength range λ0 and outputs the captured image data D0 obtained by the imaging to the imaging control unit 54 (step S4D). Accordingly, the imaging control unit 54 acquires the captured image data D0 corresponding to the needle-like recess 14 that is a measurement target from the imaging portion 34, and outputs the captured image data D0 to the image analysis unit 58 (step S5D). Hereinafter, similarly, the captured image data D0 corresponding to all of the needle-like recesses 14 in the mold 12 is output to the image analysis unit 58 (step S9D).

The image analysis unit 58 analyzes the captured image data D for each needle-like recess 14 input from the imaging control unit 54, and detects the transmitted light intensity $I_{\lambda,0}$ of the measurement light PL in the wavelength range λ0 emitted from the drug surface 18a of the aqueous drug solution 18 from the communication hole 31 through the center position of the needle-like recess 14 (see FIG. 31), for each needle-like recess 14 (step S10D). Thus, the transmitted light intensity $I_{\lambda,0}$ of each needle-like recess 14 can be acquired. That is, steps S2D to S10D correspond to a measurement wave intensity acquisition step of the present invention. Then, the image analysis unit 58 outputs a result of the acquisition of the transmitted light intensity $I_{\lambda,0}$ of each needle-like recess 14 to the distance detection unit 59.

The distance detection unit 59 detects the distance H (see FIG. 31) at the center position of each needle-like recess 14 using [General Formula 1] on the basis of the transmitted light intensity $I_{\lambda,0}$ of each needle-like recess 14, a known incident light intensity of the measurement light PL, and the optical absorption coefficient of the water corresponding to the wavelength range λ0 input from the image analysis unit 58, and outputs the result of the detection of the distance H of each needle-like recess 14 to the volume acquisition unit 60 (step S11D).

The volume acquisition unit 60 calculates (acquires) the volume of the aqueous drug solution 18 in the needle-like recesses 14 on the basis of the distance H of the center position of each needle-like recess 14 input from the distance detection unit 59, and the needle-like recess data 53 acquired from the storage unit 47 (step S12D, which corresponds to a volume acquisition step of the present invention). Further, the volume acquisition unit 60 calculates (acquires) the total volume of the aqueous drug solution 18 in the entire mold 12 from the volume of the aqueous drug solution 18 in each needle-like recess 14.

As described in the fifth embodiment described above, the volume acquisition unit 60 may acquire the volume of the aqueous drug solution 18 in each needle-like recess 14 by referring to the first data table 90A indicating a correspondence relationship between the transmitted light intensity $I_{\lambda,0}$ acquired from the storage unit 47 in advance and the volume of the aqueous drug solution 18 on the basis of the transmitted light intensity $I_{\lambda,0}$ of each needle-like recess 14 detected by the image analysis unit 58. Further, the volume acquisition unit 60 may calculate the amount of filling of the aqueous drug solution 18 in each needle-like recess 14, as described in the eighth embodiment described above. Subsequent processes are basically the same as in the first embodiment.

Thus, in the seventh embodiment, since the volume of the aqueous drug solution 18 in each needle-like recess 14 is measured using the measurement light PL in one type of wavelength range λ0, measurement accuracy is lower than in the first embodiment, but the measurement can be performed simply and in short time in comparison with the first embodiment.

Eighth Embodiment

Next, a measurement device 10 of an eighth embodiment of the present invention will be described. In the seventh embodiment, the transmitted light intensity $I_{\lambda,0}$ of the measurement light PL in the wavelength range λ0 is detected for each needle-like recess 14, but a variation in the detection result of the transmitted light intensity $I_{\lambda,0}$ may occur due to the respective units (the light source 27, the imaging optical system 33, the filter, the imaging portion 34, and the like) of the imaging unit 10A illustrated in FIG. 1 or the like described above. Therefore, in the measurement device 10 of the eighth embodiment, the transmitted light intensity $I_{\lambda,0}$ of each needle-like recess 14 in which an influence of the variation due to the respective units of the imaging unit 10A has been reduced is detected.

The measurement device 10 of the eighth embodiment has basically the same configuration as the measurement device 10 of the seventh embodiment, and components having the same function or configuration as in each of the above embodiments are denoted with the same reference signs and description thereof will be omitted.

Figure 34B:
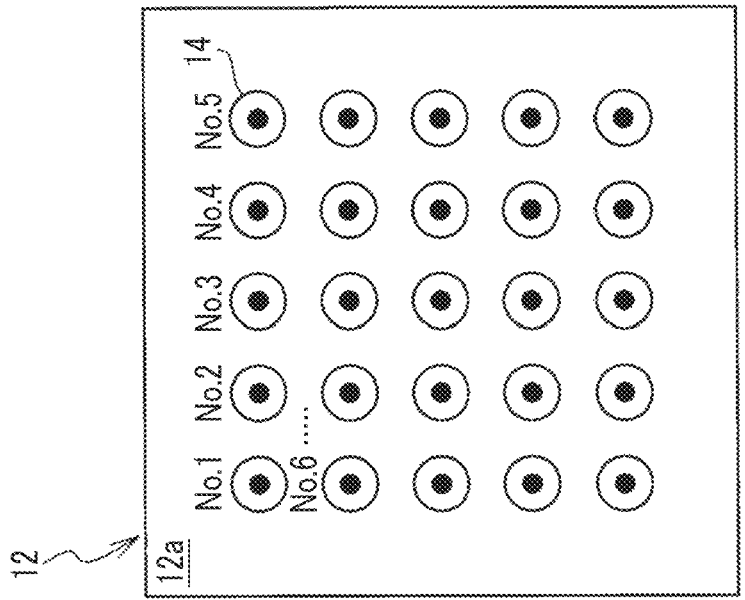
FIGS. 34A and 34B are illustrative diagrams of a normalization process for reducing an influence of fluctuation caused by each unit of an imaging unit from a detection result of a transmitted light intensity for each needle-like recess.
Figure 34A:
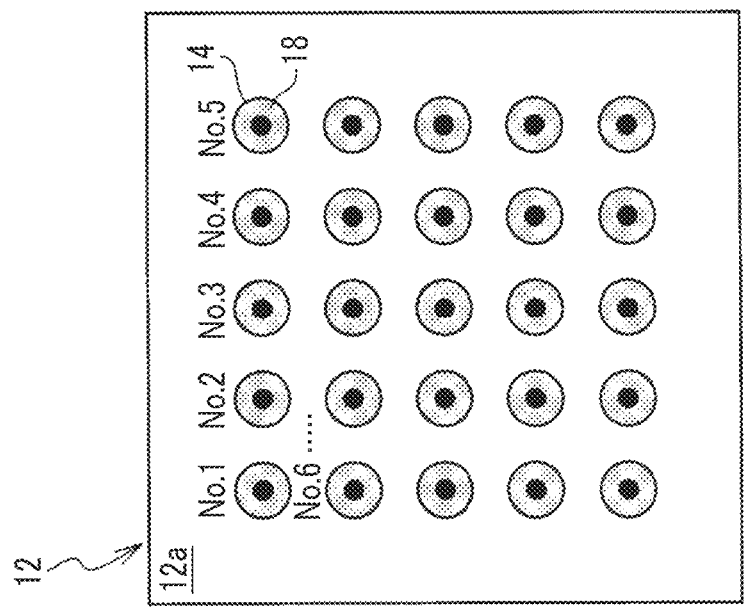

FIGS. 34A and 34B are illustrative diagrams of a normalization process for reducing an influence of variation caused by each unit of the imaging unit 10A from the detection result of the transmitted light intensity $I_{\lambda,0}$ of each needle-like recess 14. As illustrated in FIG. 34A, the measurement device 10 of the eighth embodiment performs a first acquisition process of detecting the transmitted light intensity $I_{\lambda,0}$ of the measurement light PL in the wavelength range λ0 for the respective needle-like recesses 14 (No1, No2, . . . ) in a state in which the aqueous drug solution 18 is filled in each needle-like recess 14, similar to the seventh embodiment.

Further, in the measurement device 10 of the eighth embodiment, a second acquisition process in which the measurement light PL in the wavelength range λ0 is incident on the needle-like recess 14 from the communication hole 31 in an empty state in which the aqueous drug solution 18 is not filled in the needle-like recess 14, and the transmitted light intensity $I_{\lambda,0}$ of the measurement light PL transmitted through the air in the needle-like recesses 14 is detected for each needle-like recess 14 (No1, No2, . . . ). Here, the air in the needle-like recess 14 corresponds to a region different from the drug of the present invention. A processing order of the first acquisition process and the second acquisition process is unordered.

Then, the measurement device 10 of the eighth embodiment performs a normalization process of dividing the transmitted light intensity $I_{\lambda,0}$ of each needle-like recess 14 acquired in the first acquisition process by the transmitted light intensity $I_{\lambda,0}$ of each needle-like recess 14 acquired in the second acquisition process for each needle-like recess 14. Specifically, the measurement device 10 divides the transmitted light intensity I corresponding to the needle-like recess 14 of "No1" acquired in the first acquisition process by the transmitted light intensity $I_{\lambda,0}$ corresponding to the needle-like recess 14 of "No1" acquired in the second acquisition process. Hereinafter, similarly, for the needle-like recess 14 of No2 and the subsequent needle-like recesses, the measurement device 10 divides the transmitted light intensity $I_{\lambda,0}$ acquired in the first acquisition process by the transmitted light intensity $I_{\lambda,0}$ acquired in the second acquisition process. In the measurement device 10 of the eighth embodiment, the above-described distance H is detected for each needle-like recess 14 on the basis of the transmitted light intensity $I_{\lambda 0}$ of each needle-like recess 14 subjected to the normalization process.

FIG. 35 is a flowchart illustrating a flow of measurement of the volume of the aqueous drug solution 18 in each needle-like recess 14 in the measurement device 10 of the eighth embodiment. First, before the aqueous drug solution 18 is filled in the needle-like recesses 14 of the mold 12 (step S1E), registration between the center of the imaging element of the imaging portion 34 and the center (the communication hole 31) of the needle-like recess 14 that is a measurement target is performed (step S2E).

Then, the measurement light PL in the wavelength range $\lambda 0$ is incident on the second surface 12*b* of the mold 12 from the light source 27 through an interference filter (not illustrated) or the like (step S3E). The measurement light PL in the wavelength range $\lambda 0$ is transmitted through the empty needle-like recess 14 that is a measurement target through the communication hole 31. Thus, the measurement light PL in the wavelength range $\lambda 0$ transmitted through the air in the needle-like recess 14 is incident on the imaging portion 34 through the imaging optical system 33.

The imaging portion 34 performs imaging of the measurement light PL in the wavelength range $\lambda 0$ and outputs the captured image data D0 obtained by the imaging to the imaging control unit 54 (step S4E). Accordingly, the imaging control unit 54 acquires the captured image data D0 corresponding to the empty needle-like recess 14 from the imaging portion 34, and outputs the captured image data D0 to the image analysis unit 58 (step S5E). Hereinafter, similarly, the captured image data D0 corresponding to all of the empty needle-like recesses 14 in the mold 12 is output to the image analysis unit 58 (step S9E).

Next, the aqueous drug solution 18 is filled in each needle-like recess 14 of the mold 12 (NO in step S9F, and step S9G). In a state in which the aqueous drug solution 18 is filled in each needle-like recess 14, the process from step S2E to step S9E described above is repeatedly executed. Thus, the captured image data D0 corresponding to all of the needle-like recesses 14 in the mold 12 is output from the imaging control unit 54 to the image analysis unit 58, as in the process from step S2D to step S9D of the seventh embodiment illustrated in FIG. 33 described above.

The image analysis unit 58 analyzes the captured image data D0 corresponding to the empty needle-like recess 14, and detects the transmitted light intensity $I_{\lambda 0}$ of the measurement light PL in the wavelength range $\lambda 0$ transmitted through air in the needle-like recess 14 and emitted from the communication hole 31, for each needle-like recess 14 (step S10E). Thus, the second acquisition process of the present invention is completed.

Further, the image analysis unit 58 analyzes the captured image data D0 corresponding to each needle-like recess 14 after the aqueous drug solution 18 is filled, and detects the transmitted light intensity $I_{\lambda 0}$ of the measurement light PL in the wavelength range $\lambda 0$ emitted from the drug surface 18*a* from the communication hole 31 through the center position of the needle-like recess 14, for each needle-like recess 14 (step S10E). Accordingly, a first acquisition process of the present invention is completed. Then, the image analysis unit 58 outputs the transmitted light intensity $I_{\lambda 0}$ of each needle-like recess 14 acquired in the first acquisition process and the transmitted light intensity $I_{\lambda 0}$ of each needle-like recess 14 acquired in the second acquisition process to the distance detection unit 59.

The distance detection unit 59 performs a normalization process of dividing the transmitted light intensity $I_{\lambda 0}$ of each needle-like recess 14 acquired in the first acquisition process by the transmitted light intensity $I_{\lambda 0}$ of each needle-like recess 14 acquired in the second acquisition process for each needle-like recess 14 (step S10F). The distance detection unit 59 detects the distance H (see FIG. 31) at the center position of each needle-like recess 14 using [General Formula 1] on the basis of the transmitted light intensity $I_{\lambda 0}$ of each needle-like recess 14 subjected to the normalization process, the incident light intensity of known measurement light PL, and an optical absorption coefficient of the water 19, and outputs a result of the detection of the distance H of each needle-like recess 14 to the volume acquisition unit 60 (step S11E). Since subsequent processes are basically the same as in the seventh embodiment, description thereof will be omitted.

Thus, in the eighth embodiment, it is possible to reduce an influence of fluctuation caused by each unit of the imaging unit 10A by performing the process of normalizing the transmitted light intensity $I_{\lambda 0}$ of the measurement light PL in the wavelength range $\lambda 0$ acquired for each needle-like recess 14 in a state in which the aqueous drug solution 18 is filled, using the transmitted light intensity $I_{\lambda 0}$ of the measurement light PL in the wavelength range $\lambda 0$ acquired for each needle-like recess 14 in an empty state in which the aqueous drug solution 18 is not filled. As a result, it is possible to measure the volume of the aqueous drug solution 18 in each needle-like recess 14 more accurately.

Although the normalization process in a case where the measurement is performed using the measurement light PL in one wavelength range $\lambda 0$ has been described in the eighth embodiment, the transmitted light intensity of the measurement light PL acquired in each wavelength range may be subjected to the normalization process even in a case where the measurement is performed using the measurement light PL in a plurality of wavelength ranges as in the first to sixth embodiments.

Further, in the eighth embodiment, the normalization process is performed using the transmitted light intensity $I_{\lambda 0}$ of the measurement light PL transmitted through air in the empty needle-like recesses 14, but the present invention is not limited thereto. For example, the normalization process may be performed using a transmitted light intensity of the measurement light transmitted through various regions different from the aqueous drug solution 18, such as the transmitted light intensity of the measurement light PL transmitted through a region in which the needle-like recesses 14 of the mold 12 is not formed, or the transmitted light intensity of the measurement light PL measured in a state in which the mold 12 is not set (arranged) on the imaging unit 10A.

[Others]

Although one communication hole 31 is formed in each needle-like recess 14 in the second surface 12*b* of the mold 12 in each of the above embodiments, a plurality of communication holes 31 may be formed in each needle-like recess 14. Further, a size of a diameter of the communication hole 31 may be appropriately changed.

Although the measurement device including the imaging unit and the device body has been described by way of example in each of the above embodiments, the measurement device of the present invention may include only the device body. That is, the present invention can be applied to a measurement device that acquires the detection result of the transmitted light intensity described above that has been obtained separately (or the above-described captured image data) via a memory card, a communication network, or the like and calculates the volume of the aqueous drug solution 18 on the basis of the acquired detection result or the captured image data.

Although the measurement light PL in one or a plurality of wavelength ranges are incident on the mold 12 using the interference filter in each of the above embodiments, a method of limiting the wavelength range of the measurement light PL is not limited to a method using the interference filter, and a known method may be used. Further, a light source capable of emitting the measurement light PL in one or a plurality of wavelength ranges may be used instead of limiting the wavelength range of the measurement light PL using the interference filter or the like.

Although the measurement light PL is incident from the second surface 12b of the mold 12 and the measurement light PL transmitted through the aqueous drug solution 18 in the needle-like recess 14 and emitted from the drug surface 18a to the first surface 12a is imaged by the imaging portion 34 in each of the above embodiments, the measurement light PL may be incident from the first surface 12a of the mold 12.

Figure 36:
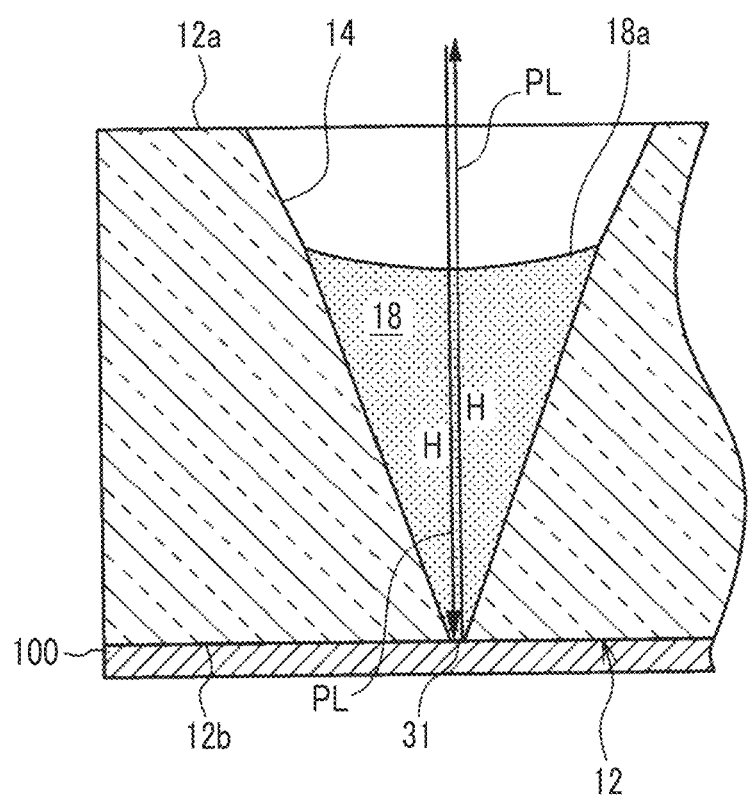
FIG. 36 is an illustrative diagram illustrating a case where incidence of measurement light on the mold from a first surface thereof is performed.

FIG. 36 is an illustrative diagram illustrating a case where incidence of the measurement light PL on the mold 12 from the first surface 12a is performed. As illustrated in FIG. 36, in a case where incidence of the measurement light PL from the first surface 12a is performed, a reflection plate 100 (or a diffusion plate) capable of reflecting the measurement light PL is provided on the second surface 12b. Accordingly, the measurement light PL incident on each position of the drug surface 18a of the aqueous drug solution 18 in each needle-like recess 14 from the first surface 12a (the measurement light PL incident on positions other than a center position is not illustrated) is transmitted through the aqueous drug solution 18 or the like and reflected by the reflection plate 100, and then, is transmitted through the aqueous drug solution 18 in the same optical path again and emitted from each position of the drug surface 18a. That is, the measurement light PL is transmitted through the aqueous drug solution 18 by a twice distance in comparison with the above embodiment.

Therefore, in a case where incidence of the measurement light PL is performed from the first surface 12a, a value (that is, H×2=2H) of twice of the distance H at each position of the drug surface 18a is obtained from, for example, the transmitted light intensities $I_{\lambda_1}$ and $I_{\lambda_2}$ of the measurement light PL in the wavelength ranges $\lambda 1$ and $\lambda 2$ emitted from each position of the drug surface 18a. Thus, it is possible to detect the distance H at each position of the drug surface 18a for each needle-like recess 14.

Since the measurement light PL incident on the mold 12 from the first surface 12a is refracted at the drug surface 18a as described in FIG. 12A and FIG. 12B of the first embodiment described above, it is preferable for the drug surface 18a to have a planar shape by performing hydrophilic treatment on the first surface 12a, as illustrated in FIG. 20B described above. Thus, it is possible to improve measurement accuracy of the distance H.

Further, in a case where the incidence of the measurement light PL is performed from the first surface 12a of the mold 12, the measurement may be performed using, for example, an integrating sphere.

Although the measurement light PL is vertically incident on the second surface 12b of the mold 12 in each of the above embodiments, the measurement light PL may be caused to be obliquely incident on the second surface 12b.

Figure 37:
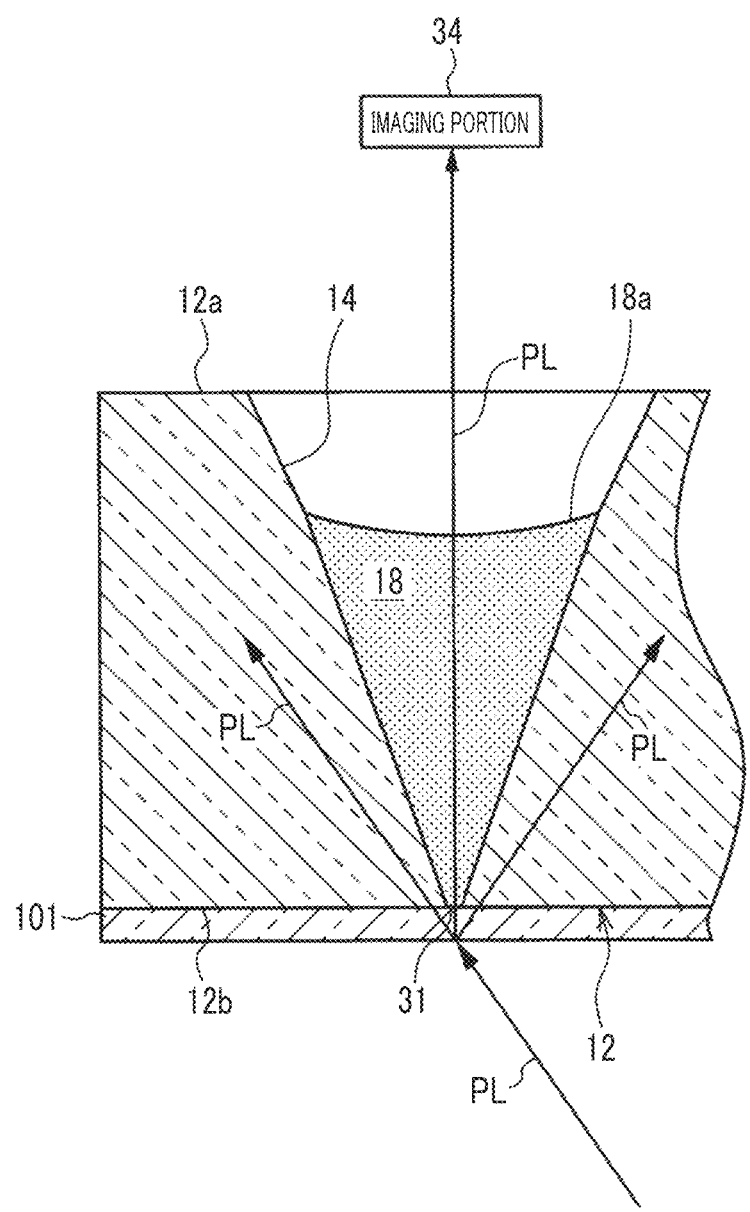
FIG. 37 is an illustrative diagram illustrating a case where measurement light is obliquely incident on a second surface of the mold.

FIG. 37 is an illustrative diagram illustrating a case where the measurement light PL is obliquely incident on the second surface 12b of the mold 12. As illustrated in FIG. 37, in a case where the measurement light PL is obliquely incident on the second surface 12b, a diffusion plate 101 (or a diffusion plate) capable of diffusing the measurement light PL is provided on the second surface 12b. Accordingly, the measurement light PL obliquely incident on the second surface 12b of the mold 12 is diffused by the diffusion plate 101. In this case, if there is a distance between the mold 12 and the imaging portion 34, the amount by which the measurement light PL other than the measurement light PL vertically incident on the second surface 12b is incident on the imaging portion 34 in the measurement light PL (diffused light) diffused by the diffusion plate 101 is small. Therefore, even in a case where the measurement light PL is obliquely incident on the second surface 12b, it is possible to selectively image the measurement light PL vertically incident on the second surface 12b using the imaging portion 34.

Although the case in which the volume of the aqueous drug solution 18 in each needle-like recess 14 of the mold 12 is measured has described in each of the above embodiments, the present invention can also be applied to a case where a volume of a solid or gel drug 16 in each needle-like recess 14 of the mold 12 is measured. In this case, light in the wavelength range light-absorbed by the drug 16 is used as the measurement light PL.

Although the measurement light PL has been described as an example of the measurement wave of the present invention in each of the above embodiments, various physical waves such as heat, radio waves, and sound waves other than light may be used as the measurement wave of the present invention.

[Program Causing Computer to Function as Means for Measuring Volume of Aqueous Drug Solution]

A program (the above-described measurement program 51 or the like) for causing a computer to function as a measurement device described in the above embodiment can be recorded on an optical disk, a magnetic disk, or another computer-readable medium (a tangible non-transitory information storage medium), and the program can be provided through the information storage medium. A program signal can be provided as a download service using a communication network such as the Internet, instead of an aspect in which the program is stored in the information storage medium and provided.

EXPLANATION OF REFERENCES

10: measurement device
10A: imaging unit
10B: device body
12: mold
12a: first surface
12b: second surface
14: needle-like recess
16: drug
18: aqueous drug solution
18a: liquid surface
27: light source
32: wavelength selection filter
54: imaging control unit
58: image analysis unit
59: distance detection unit
60: volume acquisition unit
61: three-dimensional shape calculation unit

What is claimed is:

1. A measurement method of non-destructively measuring a volume of a drug filled in a needle-shaped recess of a mold in which a plurality of needle-shaped recesses that are inverted shapes of a micro-needle are formed, the measurement method comprising:
a measurement wave emission step of emitting a measurement wave toward the drug filled in the needle-shaped recess;
a measurement wave intensity measurement step of measuring, for each needle-shaped recess, an intensity of the measurement wave transmitted through the drug in the needle-shaped recess, absorbed by the drug by an amount according to a distance by which the measurement wave is transmitted through the drug, and emitted from the drug; and
a volume calculation step of calculating, by a calendar, the volume for each needle-shaped recess on the basis of the intensity of the measurement wave for each needle-shaped recess and absorbed by and transmitted through the drug measured in the measurement wave intensity measurement step.

2. The measurement method according to claim 1, wherein the measurement wave intensity measurement step includes acquiring the intensity of the measurement wave in a wavelength range absorbed by the water, for each of the needle-shaped recesses, in a case where the drug contains water.

3. The measurement method according to claim 1, wherein the volume calculation step includes acquiring a total volume of the volume of the drug filled in the mold from the volume of the drug of each needle-shaped recess.

4. The measurement method according to claim 1, further comprising:
an acquisition result processing step of executing at least one of a display of the acquisition result acquired in the volume calculation step and storage of the acquisition result in a storage unit.

5. The measurement method according to claim 1, wherein the measurement wave intensity measurement step includes:
a first acquisition process of acquiring, for each needle-shaped recess, an intensity of the measurement wave transmitted through the drug in the needle-shaped recess and emitted from the drug;
a second acquisition process of acquiring an intensity of the measurement wave transmitted through a region different from the drug; and
a normalization process of normalizing the intensity of the measurement wave for each needle-shaped recess acquired in the first acquisition process, using the intensity of the measurement wave acquired in the second acquisition process, and
the volume calculation step includes calculating the volume for each needle-shaped recess on the basis of the intensity of the measurement wave for each needle-shaped recess subjected to the normalization process.

6. The measurement method according to claim 1, wherein the volume calculation step includes calculating, for each needle-shaped recess, a distance by which the measurement wave is transmitted through the drug in the needle-shaped recess on the basis of the intensity of the measurement wave of each needle-shaped recess acquired in the measurement wave intensity measurement step, and acquiring the volume of the drug for each of the needle-shaped recesses on the basis of the acquired distance of each needle-shaped recess and a known shape of the needle-shaped recesses.

7. The measurement method according to claim 1, wherein the volume calculating step includes calculating the volume of the drug of each needle-shaped recess by referring to a correspondence relationship between an intensity of the measurement wave that is acquired in advance and the volume on the basis of the intensity of the measurement wave of each needle-shaped recess acquired in the measurement wave intensity measurement step.

8. The measurement method according to claim 1, wherein the measurement wave intensity measurement step includes repeatedly performing a process of acquiring, for each needle-shaped recess, the intensity of the measurement wave incident on the mold from a second surface opposite to a first surface on which the drug of the mold is filled, and emitted from the drug surface of the drug, while changing the wavelength range of the measurement wave, and
the volume calculating step includes:
a distance detection step of detecting, for each needle-shaped recess, a distance by which the measurement wave in the plurality of wavelength ranges emitted from each position of the drug surface is transmitted through the drug from the acquisition result acquired for each wavelength range in the measurement wave intensity measurement step; and
a volume calculation step of calculating the volume for each needle-shaped recess on the basis of the result of the detection of the distance detection step.

9. The measurement method according to claim 8, wherein the measurement wave intensity measurement step includes:
an incidence step of causing the measurement wave to be incident on the second surface in a case where the measurement wave is light;
an arrangement step of alternately inserting and arranging a plurality of filters that limit a wavelength range of the measurement wave into and in an optical path of the measurement wave, the wavelength range limited by the plurality of filters being different;
a captured image acquisition step of acquiring, for every plurality of filters, a captured image obtained by imaging the measurement wave transmitted through any one of the plurality of filters and the drug; and
an image analysis step of analyzing the captured image for every plurality of filters acquired in the captured image acquisition step and detecting an intensity of the measurement wave for each needle-shaped recess for every plurality of wavelength ranges corresponding to the plurality of filters.

10. The measurement method according to claim 8, wherein in a case where the measurement wave is a first measurement wave and a second measurement wave in different wavelength ranges, and
in a case where the intensity of the first measurement wave at each position is $I_{\lambda 1}$, the intensity of the second measurement wave at each position is $I_{\lambda 2}$, and a parameter affecting the intensity of the first measurement wave and the intensity of the second measurement wave is P, the distance detection step includes calculating the distance H at each position
from $I_{\lambda 1}$, $I_{\lambda 2}$, and P.

11. The measurement method according to claim 10, wherein in a case where the drug contains water and the first measurement wave and the second measurement wave are light, the parameter P includes an optical absorption coefficient $\alpha_{\lambda,1}$ of the water corresponding to the first measurement wave and an optical absorption coefficient $\alpha_{\lambda,2}$ of the water corresponding to the second measurement wave, and the distance detection step includes calculating the distance H at each position from $I_{\lambda,1}$, $I_{\lambda,2}$, $\alpha_{\lambda,1}$, $\alpha_{\lambda,2}$ and P.

12. The measurement method according to claim 8, wherein the volume calculation step includes acquiring the volume of the drug of each needle-shaped recess by referring to a correspondence relationship between at least one of intensities of the measurement wave in the respective wavelength ranges acquired in advance and the volume on the basis of the intensity of the measurement wave of each needle-shaped recess acquired for each wavelength range in the measurement wave intensity measurement step.

13. The measurement method according to claim 8, further comprising:

a shape detection step of detecting a shape of the drug surface of each needle-shaped recess on the basis of a detection result in the distance detection step and a known shape of the needle-shaped recess.

14. The measurement method according to claim 1, wherein the measurement wave is light, and the drug absorbs light in a plurality of specific wavelength ranges and includes water having a different optical absorbance for each specific wavelength range, and the measurement wave intensity measurement step includes determining the wavelength range of the measurement wave from among the plurality of specific wavelength ranges according to a thickness of the mold.

15. The measurement method according to claim 1, wherein the measurement wave is light, and the drug absorbs light in a plurality of specific wavelength ranges and includes water having a different optical absorbance for each specific wavelength range, and the measurement wave intensity measurement step includes determining the wavelength range of the measurement wave from among the plurality of specific wavelength ranges according to the amount of filling of the drug filled in the needle-shaped recess.

16. A measurement method of measuring a volume of a drug filled in a needle-shaped recess of a mold in which a plurality of needle-shaped recesses that are inverted shapes of a micro-needle are formed, the measurement method comprising:

a measurement wave emission step of emitting a measurement wave toward the drug filled in the needle-shaped recess;

a measurement wave intensity measurement step of measuring, for each needle-shaped recess, an intensity of the measurement wave transmitted through the drug in the needle-shaped recess, absorbed by the drug by an amount according to a distance by which the measurement wave is transmitted through the drug, and emitted from the drug; and a volume calculation step of calculating, by a calculator, the volume for each needle-shaped recess on the basis of the intensity of the measurement wave for each needle-shaped recess measured in the measurement wave intensity measurement step, wherein the volume of the drug decreases over time due to evaporation of the water contained in the drug, the measurement method further comprises an elapsed time acquisition step of acquiring an elapsed time until the measurement wave intensity measurement step starts after the drug is filled in the needle-shaped recess, and the volume calculation step includes correcting a decrease over time of the volume of the drug of each needle-shaped recess on the basis of the elapsed time acquired in the elapsed time acquisition step, and acquiring the amount of filling of the drug filled in the needle-shaped recess for each needle-shaped recess.

17. The measurement method according to claim 16, further comprising:

a correction value acquisition step of acquiring a correction value for correcting a decrease over time of the volume of the drug in the needle-shaped recess, wherein the volume calculation step includes correcting the volume of the drug of each needle-shaped recess using the correction value acquired in the correction value acquisition step on the basis of the elapsed time acquired in the elapsed time acquisition step, and acquiring the amount of filling of the drug of each needle-shaped recess.

18. A measurement method of measuring a volume of a drug filled in a needle-shaped recess of a mold in which a plurality of needle-shaped recesses that are inverted shapes of a micro-needle are formed, the measurement method comprising:

a measurement wave emission step of emitting a measurement wave toward the drug filled in the needle-shaped recess;

a measurement wave intensity measurement step of measuring, for each needle-shaped recess, an intensity of the measurement wave transmitted through the drug in the needle-shaped recess, absorbed by the drug by an amount according to a distance by which the measurement wave is transmitted through the drug, and emitted from the drug; and a volume calculation step of calculating, by a calculator, the volume for each needle-shaped recess on the basis of the intensity of the measurement wave for each needle-shaped recess measured in the measurement wave intensity measurement step, wherein the measurement wave intensity measurement step includes repeatedly performing a process of acquitting, for each needle-shaped recess, the intensity of the measurement wave incident on the mold from a second surface opposite to a first surface on which the drug of the mold is filled, and emitted from the drug surface of the drug, while changing the wavelength range of the measurement wave, and the volume calculation step includes:

a distance detection step of detecting, for each needle-shaped recess, a distance by which the measurement wave in the plurality of wavelength ranges emitted from each position of the drug surface is transmitted through the drug from the acquisition result acquired for each wavelength range in the measurement wave intensity measurement step; and a volume calculation step of calculating the volume for each needle-shaped recess on the basis of the result of the detection of the distance detection step, wherein in a case where the measurement wave is a first measurement wave and a second measurement wave in different wavelength ranges, and the distance detection step includes detecting the distance at each position on the basis of a difference between the intensity of the first measurement wave at each position and the intensity of the second measurement wave at each position.

19. The measurement method according to claim 18, wherein in a case where the drug contains water and the first measurement wave and the second measurement wave are light, the parameter P includes an optical absorption coefficient $\alpha_{\lambda_1}$ of the water corresponding to the first measurement wave and an optical absorption coefficient $\alpha_{\lambda_2}$ of the water corresponding to the second measurement wave, and wherein the distance detection step includes calculating the distance H at each position using the following formula:

$$H = \frac{\log_{10} I_{\lambda_1} - \log_{10} I_{\lambda_2}}{\alpha_{\lambda_2} - \alpha_{\lambda_1}}.$$

20. The measurement method according to claim 18, wherein in a case where the measurement wave is a first measurement wave and a second measurement wave in different wavelength ranges, the measurement wave intensity measurement step includes acquiring an incidence intensity of each of the first measurement wave and the second measurement wave incident on the second surface, and an emission intensity of each of the first measurement wave and the second measurement wave emitted from each position of the drug surface for each needle-shaped recess, and the distance detection step includes obtaining the distance H at each position using the following formula on the basis of the acquisition result of the measurement wave intensity measurement step, an optical absorption coefficient $\alpha_{\lambda_1}$ of the water corresponding to the first measurement wave, and an optical absorption coefficient $\alpha_{\lambda_2}$ of the water corresponding to the second measurement wave, $$H = -\frac{\log_{10} I_{\lambda_2}^{out} - \log_{10} I_{\lambda_1}^{out} - (\log_{10} I_{\lambda_2}^{in} - \log_{10} I_{\lambda_1}^{in})}{\alpha_{\lambda_2} - \alpha_{\lambda_1}}$$

$I_{\lambda_1}^{in}$: Incidence intensity of first measurement wave
$I_{\lambda_1}^{out}$: Emission intensity of first measurement wave
$I_{\lambda_2}^{in}$: Incidence intensity of second measurement wave
$I_{\lambda_2}^{out}$: Emission intensity of second measurement wave
$\alpha_{\lambda_1}$: Optical absorption coefficient of water corresponding to first measurement wave
$\alpha_{\lambda_2}$: Optical absorption coefficient of water corresponding to second measurement wave.

21. The measurement method according to claim 18, wherein in a case where the measurement wave is a first measurement wave, a second measurement wave, and a third measurement wave in different wavelength ranges, the measurement wave intensity measurement step includes acquiring an incidence intensity of each of the first measurement wave, the second measurement wave, and the third measurement wave incident on the second surface, and an emission intensity of each of the first measurement wave, the second measurement wave, and the third measurement wave emitted from each position of the drug surface for each needle-shaped recess, and the distance detection step includes obtaining the distance H at each position using the following formula on the basis of the acquisition result of the measurement wave intensity measurement step, an optical absorption coefficient $\alpha_{\lambda_1}$ of the water corresponding to the first measurement wave, an optical absorption coefficient $\alpha_{\lambda_2}$ of the water corresponding to the second measurement wave, and an optical absorption coefficient $\alpha_{\lambda_3}$ of the water corresponding to the third measurement wave, $$H = \operatorname*{argmin}_{H=0 \sim H_{max}} \{\Delta D = |(I_{\lambda_1}^{out} - I_{\lambda_2}^{out}) \cdot (I_{\lambda_3}^{in} \cdot 10^{-\alpha_{\lambda_3} \cdot H} - I_{\lambda_2}^{in} \cdot 10^{-\alpha_{\lambda_2} \cdot H}) - (I_{\lambda_3}^{out} - I_{\lambda_2}^{out}) \cdot (I_{\lambda_1}^{in} \cdot 10^{-\alpha_{\lambda_1} \cdot H} - I_{\lambda_2}^{in} \cdot 10^{-\alpha_{\lambda_2} \cdot H})|\}$$

$I_{\lambda_1}^{in}$: Incidence intensity of first measurement wave
$I_{\lambda_1}^{out}$: Emission intensity of first measurement wave
$I_{\lambda_2}^{in}$: Incidence intensity of second measurement wave
$I_{\lambda_2}^{out}$: Emission intensity of second measurement wave
$I_{\lambda_3}^{in}$: Incidence intensity of third measurement wave
$I_{\lambda_3}^{out}$: Emission intensity of third measurement wave
$\alpha_{\lambda_1}$: Optical absorption coefficient of water corresponding to first measurement wave
$\alpha_{\lambda_2}$: Optical absorption coefficient of water corresponding to second measurement wave
$\alpha_{\lambda_3}$: Optical absorption coefficient of water corresponding to third measurement wave.

22. A measurement device that non-destructively measures a volume of a drug filled in a needle-shaped recess of a mold in which a plurality of needle-shaped recesses that are inverted shapes of a micro-needle are formed, the measurement device comprising:

An imager configured to image the needle-shaped recess containing the drug and irradiated with a measurement wave;

an image analyzer configured to measure, for each needle-shaped recess, an intensity of the measurement wave transmitted through the drug in the needle-shaped recess, absorbed by the drug by an amount according to a distance by which the measurement wave is transmitted through the drug, and emitted from the drug, based on an image of the needle-shaped recess imaged by the imager; and a calculator configured to calculate the volume for each needle-shaped recess on the basis of the intensity of the measurement wave for each needle-shaped recess and absorbed by and transmitted through the drug measured by the image analyzer.

23. A non-transitory computer-readable tangible medium recording a program that causes a computer to function as means for non-destructively measuring a volume of a drug filled in a needle-shaped recess of a mold in which a plurality of needle-shaped recesses that are inverted shapes of a micro-needle are formed, the program causing the computer to function as:

An imager configured to image the needle-shaped recess containing the drug and irradiated with a measurement wave;

an image analyzer configured to measure an intensity of a measurement wave for each needle-shaped recess transmitted through the drug in the needle-shaped recess, absorbed by the drug by an amount according to a distance by which the measurement wave is transmitted through the drug, and emitted from the drug; based on an image of the needle-shaped recess imaged by the imager; and a calculator configured to calculate the volume for each needle-shaped recess on the basis of the intensity of the measurement wave for each needle-shaped recess measured by the image analyzer.

24. A measurement method of non-destructive measuring a volume of a drug filled in a needle-shaped recess of a mold in which a plurality of needle-shaped recesses that are inverted shapes of a micro-needle are formed, the measurement method comprising:

a measurement wave intensity measurement step of measuring, for each needle-shaped recess, an intensity of a measurement wave transmitted through the drug in the needle-shaped recess, absorbed by the drug by an amount according to a distance by which the measurement wave is transmitted through the drug, and emitted from the drug; and a volume calculation step of calculating, by a calculator, the volume for each needle-shaped recess on the basis of the intensity of the measurement wave for each needle-shaped recess and absorbed by and transmitted through the drug measured in the measurement wave intensity measurement step, wherein the measurement wave is a light, the drug absorbs light in a plurality of specific wavelength ranges and includes water having a different optical absorbance for each specific wavelength range, the measurement wave intensity measurement step includes allowing the measurement wave having been diffused via a diffusion plate arranged on a side of a second surface of the mold opposite to a first surface of the mold on which the drug is filled, to be incident on the second surface, and the intensity of the measurement wave emitted from the first surface is measured, for each needle-shaped recess, with an imager arranged on a side of the first surface.

25. A measurement device that non-destructively which a plurality of needle-shaped recesses that are inverted shapes of a micro-needle are formed, the measurement device comprising:

a wave intensity processor configured to measure, for each needle-shaped recess, an intensity of a measurement wave transmitted through the drug in the needle-shaped recess, absorbed by the drug by an amount according to a distance by which the measurement wave is transmitted through the drug, and emitted from the drug; and a calculator configured to calculate the volume for each needle-shaped recess on the basis of the intensity of the measurement wave for each needle-shaped recess and absorbed by and transmitted through the drug measured by the wave intensity processor, wherein the measurement wave is a light, the drug absorbs light in a plurality of specific wavelength ranges and includes water having a different optical absorbance for each specific wavelength range, the wave intensity processor is further configure to allow the measurement wave having been diffused via a diffusion plate arranged on a side of a second surface of the mold opposite to a first surface of the mold on which the drug is filled, to be incident on the second surface, and the intensity of the measurement wave emitted from the first surface is measured, for each needle-shaped recess, with an imager arranged on a side of the first surface.

26. A non-transitory computer readable medium including a program controlling a processor for performing non-destructive measuring a volume of a drug filled in a needle-shaped recess of a mold in which a plurality of needle-shaped recesses that are inverted shapes of a micro-needle are formed, the computer readable medium causing the processor to perform:

a measurement wave intensity measurement step of measuring, for each needle-shaped recess, an intensity of a measurement wave transmitted through the drug in the needle-shaped recess, absorbed by the drug by an amount according to a distance by which the measurement wave is transmitted through the drug, and emitted from the drug; and a volume calculation step of calculating, by a calculator, the volume for each needle-shaped recess on the basis of the intensity of the measurement wave for each needle-shaped recess and absorbed by and transmitted through the drug measured in the measurement wave intensity measurement step, wherein the measurement wave is a light, the drug absorbs light in a plurality of specific wavelength ranges and includes water having a different optical absorbance for each specific wavelength range, the measurement wave intensity measurement step includes allowing the measurement wave having been diffused via a diffusion plate arranged on a side of a second surface of the mold opposite to a first surface of the mold on which the drug is filled, to be incident on the second surface, and the intensity of the measurement wave emitted from the first surface is measured, for each needle-shaped recess, with an imager arranged on a side of the first surface.

* * * * *